(12) United States Patent
Church et al.

(10) Patent No.: US 12,741,042 B2
(45) Date of Patent: Sep. 22, 2026

(54) MODULAR LIGHT DEVICE FOR A BIOLOGICAL FLUID TREATMENT SYSTEM

(71) Applicant: Cerus Corporation, Concord, CA (US)

(72) Inventors: Daniel Church, Danville, CA (US); Lloyd Ison, Livermore, CA (US)

(73) Assignee: Cerus Corporation, Concord, CA (US)

( * ) Notice: Subject to any disclaimer, the term of this patent is extended or adjusted under 35 U.S.C. 154(b) by 1064 days.

(21) Appl. No.: 17/451,311

(22) Filed: Oct. 18, 2021

(65) Prior Publication Data

US 2022/0118136 A1 Apr. 21, 2022

Related U.S. Application Data

(60) Provisional application No. 63/093,722, filed on Oct. 19, 2020.

(51) Int. Cl.
*A61L 2/10* (2026.01)
*A61L 2/02* (2006.01)
*A61L 2/16* (2006.01)
*A61L 103/05* (2026.01)

(52) U.S. Cl.
CPC .................. *A61L 2/10* (2013.01); *A61L 2/02* (2013.01); *A61L 2/16* (2013.01); *A61L 2103/05* (2026.01)

(58) Field of Classification Search
CPC ................................ A61L 2/10; A61L 2/0047
See application file for complete search history.

(56) References Cited

U.S. PATENT DOCUMENTS 3,261,594 A 7/1966 Michel
3,480,015 A 11/1969 Gonzalez
4,227,902 A 10/1980 Olson
4,952,812 A 8/1990 Miripol et al.
5,167,656 A 12/1992 Lynn
5,221,608 A 6/1993 Cimino et al.
5,288,605 A 2/1994 Lin et al.
5,399,719 A 3/1995 Wollowitz et al.
5,405,343 A 4/1995 Mohr
5,418,130 A 5/1995 Platz et al.
(Continued)

FOREIGN PATENT DOCUMENTS

CN 1284886 A 2/2001
CN 1450916 A 10/2003
(Continued)

OTHER PUBLICATIONS

Anonymous (2018). "DS9900 Series Corded Hybrid Imager for Labs," Zebra, 4 pages.
(Continued)

*Primary Examiner* — Timothy C Cleveland
(74) *Attorney, Agent, or Firm* — MORRISON & FOERSTER LLP

(57) ABSTRACT

Provided herein are systems and methods for implementing a modular light device for use in an electronic treatment device according to examples of the disclosure. In one or more examples, the modular light device can be implemented as a stand-alone component that can be swapped in and out of the treatment device. In one or more examples, the light device can include a light source array chamber configured to transmit UV light of a selected wavelength, the light source array chamber including one or more light source arrays and light sensors collectively configured as part of the light device to deliver light to a biological sample.

60 Claims, 22 Drawing Sheets

(56) References Cited

U.S. PATENT DOCUMENTS

| | | | |
|---|---|---|---|
| 5,459,030 | A | 10/1995 | Lin et al. |
| 5,482,828 | A | 1/1996 | Lin et al. |
| 5,556,958 | A | 9/1996 | Carroll |
| 5,556,993 | A | 9/1996 | Wollowitz |
| 5,559,250 | A | 9/1996 | Cook |
| 5,571,082 | A | 11/1996 | Bashikirov |
| 5,578,736 | A | 11/1996 | Wollowitz |
| 5,585,503 | A | 12/1996 | Wollowitz |
| 5,589,462 | A | 12/1996 | Patat |
| 5,593,823 | A | 1/1997 | Wollowitz et al. |
| 5,618,662 | A | 4/1997 | Lin et al. |
| 5,625,079 | A | 4/1997 | Wollowitz et al. |
| 5,654,443 | A | 8/1997 | Wollowitz |
| 5,691,132 | A | 11/1997 | Wollowitz et al. |
| 5,709,991 | A | 1/1998 | Lin et al. |
| 5,712,085 | A | 1/1998 | Wollowitz |
| 5,871,900 | A | 2/1999 | Wollowitz |
| 5,908,742 | A | 6/1999 | Lin et al. |
| 5,965,349 | A | 10/1999 | Lin |
| 5,972,593 | A | 10/1999 | Wollowitz |
| 6,004,741 | A | 12/1999 | Wollowitz |
| 6,004,742 | A | 12/1999 | Wollowitz |
| 6,017,691 | A | 1/2000 | Wollowitz et al. |
| 6,093,725 | A | 7/2000 | Cook et al. |
| 6,133,460 | A | 10/2000 | Wollowitz et al. |
| 6,143,490 | A | 11/2000 | Cook et al. |
| 6,171,777 | B1 | 1/2001 | Cook |
| 6,177,441 | B1 | 1/2001 | Cook et al. |
| 6,194,139 | B1 | 2/2001 | Wollowitz |
| 6,218,100 | B1 | 4/2001 | Wollowitz |
| 6,251,580 | B1 | 6/2001 | Lin |
| 6,270,952 | B1 | 8/2001 | Cook et al. |
| 6,277,337 | B1 | 8/2001 | Goodrich, Jr. et al. |
| 6,281,225 | B1 | 8/2001 | Hearst et al. |
| 6,410,219 | B1 | 6/2002 | Cook et al. |
| 6,420,570 | B1 | 7/2002 | Wollowitz |
| 6,433,343 | B1 | 8/2002 | Cimino et al. |
| 6,455,286 | B1 | 9/2002 | Wollowitz |
| 6,469,052 | B2 | 10/2002 | Wollowitz |
| 6,494,753 | B1 | 12/2002 | Tomasino et al. |
| 6,503,699 | B1 | 1/2003 | Wollowitz et al. |
| 6,514,987 | B1 | 2/2003 | Cook et al. |
| 6,544,727 | B1 | 4/2003 | Hei |
| 6,548,242 | B2 | 4/2003 | Horowitz et al. |
| 6,565,802 | B1 | 5/2003 | Hanley |
| 6,586,749 | B2 | 7/2003 | Cimino |
| 6,686,480 | B2 | 2/2004 | Wollowitz |
| 6,709,810 | B2 | 3/2004 | Cook |
| 6,843,961 | B2 | 1/2005 | Hlavinka et al. |
| 6,949,753 | B2 | 9/2005 | Cimino |
| 6,951,713 | B2 | 10/2005 | Hei et al. |
| 6,986,867 | B2 | 1/2006 | Hanley et al. |
| 7,025,877 | B1 | 4/2006 | De |
| 7,037,642 | B2 | 5/2006 | Hei et al. |
| 7,105,093 | B2 | 9/2006 | De |
| 7,293,985 | B2 | 11/2007 | Cook |
| 7,425,304 | B2 | 9/2008 | De |
| 7,433,030 | B2 | 10/2008 | Waldo et al. |
| 7,459,695 | B2 | 12/2008 | Hanley et al. |
| 7,601,298 | B2 | 10/2009 | Waldo et al. |
| 7,611,831 | B2 | 11/2009 | Hei |
| 7,655,392 | B2 | 2/2010 | Stassinopoulos |
| 7,788,038 | B2 | 8/2010 | Oshita |
| 7,829,867 | B2 | 11/2010 | Hlavinka et al. |
| 7,852,490 | B2 | 12/2010 | Kiesel et al. |
| 8,296,071 | B2 | 10/2012 | Edrich et al. |
| 8,492,162 | B2 | 7/2013 | Kippenhan |
| 8,778,263 | B2 | 7/2014 | Walker et al. |
| 8,830,449 | B1 | 9/2014 | Lamego et al. |
| 8,900,805 | B2 | 12/2014 | Mufti et al. |
| 9,259,525 | B2 | 2/2016 | Hei |
| 9,320,817 | B2 | 4/2016 | Walker et al. |
| 9,713,627 | B2 | 7/2017 | Mufti |
| 10,004,821 | B2 | 6/2018 | Dobrinsky |
| 10,357,516 | B2 | 7/2019 | Mufti |
| 10,506,915 | B2 | 12/2019 | Iwasaki |
| 10,758,868 | B2 | 9/2020 | Fulkerson |
| 10,799,533 | B2 | 10/2020 | Corash |
| 10,842,818 | B2 | 11/2020 | Vermeij |
| 11,096,963 | B2 | 8/2021 | Corash et al. |
| 11,660,365 | B2 | 5/2023 | Thompson |
| 11,883,544 | B2 | 1/2024 | Church |
| 12,011,510 | B2 | 6/2024 | Church et al. |
| 12,214,092 | B2 | 2/2025 | Church et al. |
| 12,343,436 | B2 | 7/2025 | Church et al. |
| 12,514,944 | B2 | 1/2026 | Church et al. |
| 12,558,442 | B2 | 2/2026 | Church et al. |
| 2001/0009756 | A1 | 7/2001 | Hei |
| 2001/0018179 | A1 | 8/2001 | Hei |
| 2002/0006393 | A1 | 1/2002 | Wollowitz |
| 2002/0028432 | A1 | 3/2002 | Cook |
| 2002/0042043 | A1 | 4/2002 | Stassinopoulos |
| 2002/0115585 | A1 | 8/2002 | Hei |
| 2002/0192632 | A1 | 12/2002 | Hei |
| 2003/0035751 | A1 | 2/2003 | Hanley et al. |
| 2003/0062483 | A1 | 4/2003 | Cimino |
| 2003/0105339 | A1 | 6/2003 | Wollowitz |
| 2003/0113704 | A1 | 6/2003 | Stassinopoulos |
| 2003/0146162 | A1 | 8/2003 | Metzel et al. |
| 2003/0185804 | A1 | 10/2003 | Wollowitz et al. |
| 2003/0207247 | A1 | 11/2003 | Stassinopoulos et al. |
| 2003/0219354 | A1 | 11/2003 | Hlavinka et al. |
| 2004/0021809 | A1 | 2/2004 | Sumiyoshi et al. |
| 2004/0029897 | A1 | 2/2004 | Cook |
| 2004/0088189 | A1 | 5/2004 | Veome et al. |
| 2004/0172007 | A1 | 9/2004 | Grimm et al. |
| 2004/0180321 | A1 | 9/2004 | Cook |
| 2004/0185544 | A9 | 9/2004 | Hei |
| 2004/0185553 | A9 | 9/2004 | Hei |
| 2004/0197343 | A1 | 10/2004 | Dubensky et al. |
| 2004/0228877 | A1 | 11/2004 | Dubensky et al. |
| 2005/0142542 | A1 | 6/2005 | Hei |
| 2005/0175625 | A1 | 8/2005 | Jaffee et al. |
| 2005/0202395 | A1 | 9/2005 | Edrich et al. |
| 2005/0249748 | A1 | 11/2005 | Dubensky et al. |
| 2005/0281783 | A1 | 12/2005 | Kinch et al. |
| 2006/0093999 | A1 | 5/2006 | Hei |
| 2006/0115466 | A1 | 6/2006 | Stassinopoulos |
| 2006/0197031 | A1 | 9/2006 | De et al. |
| 2006/0221329 | A1 | 10/2006 | Waldo et al. |
| 2007/0031457 | A1 | 2/2007 | Dubensky et al. |
| 2007/0190029 | A1 | 8/2007 | Pardoll et al. |
| 2007/0190063 | A1 | 8/2007 | Bahjat et al. |
| 2007/0207170 | A1 | 9/2007 | Dubensky et al. |
| 2007/0207171 | A1 | 9/2007 | Dubensky et al. |
| 2007/0235376 | A1 | 10/2007 | Daniel |
| 2009/0250626 | A1 | 10/2009 | Schlesser et al. |
| 2010/0133160 | A1 | 6/2010 | Hei |
| 2011/0209212 | A1 | 8/2011 | Newlin et al. |
| 2011/0286987 | A1 | 11/2011 | Mufti |
| 2012/0070339 | A1 | 3/2012 | Lawal |
| 2012/0073614 | A1 | 3/2012 | Otani |
| 2012/0153783 | A1 | 6/2012 | Shoenfeld |
| 2012/0313014 | A1 | 12/2012 | Stibich et al. |
| 2013/0320299 | A1 | 12/2013 | Li |
| 2013/0323128 | A1 | 12/2013 | Owen et al. |
| 2014/0303547 | A1 | 10/2014 | Loupis et al. |
| 2014/0346370 | A1 | 11/2014 | Dobrinsky et al. |
| 2014/0353519 | A1 | 12/2014 | Wang |
| 2015/0157665 | A1 | 6/2015 | Mufti |
| 2015/0299000 | A1 | 10/2015 | Smith et al. |
| 2016/0324997 | A1 | 11/2016 | Dayton |
| 2016/0354533 | A1 | 12/2016 | Hei |
| 2017/0014538 | A1 | 1/2017 | Rantala |
| 2017/0027986 | A1 | 2/2017 | Corash et al. |
| 2017/0028121 | A1 | 2/2017 | Manzella et al. |
| 2017/0050046 | A1 | 2/2017 | Walder et al. |
| 2017/0054687 | A1 | 2/2017 | Ishigaki |
| 2017/0202882 | A1 | 7/2017 | Vermeij |
| 2017/0252474 | A1 | 9/2017 | Thompson et al. |
| 2017/0304363 | A1 | 10/2017 | Corash |
| 2018/0008639 | A1 | 1/2018 | Mufti |
| 2018/0113066 | A1 | 4/2018 | Freitag et al. |
| 2018/0147306 | A1 | 5/2018 | Crawley et al. |

(56) References Cited

U.S. PATENT DOCUMENTS

2018/0184985 A1 7/2018 Håkansson et al.
2018/0185484 A1 7/2018 Greenman et al.
2018/0193500 A1 7/2018 Safavi et al.
2018/0289873 A1 10/2018 David
2018/0318348 A1 11/2018 Corash et al.
2018/0369437 A1 12/2018 Grossman et al.
2019/0041308 A1 2/2019 Schryver et al.
2019/0085289 A1 3/2019 Greenman
2019/0099543 A1 4/2019 Sasaki
2019/0100718 A1 4/2019 Estes et al.
2019/0209718 A1 7/2019 Church
2019/0321407 A1 10/2019 Erickson et al.
2019/0369087 A1 12/2019 North et al.
2020/0063179 A1 2/2020 Eghbal
2020/0078406 A1 3/2020 Weiner et al.
2020/0397931 A1 12/2020 Church et al.
2020/0397935 A1 12/2020 Church et al.
2020/0405891 A1 12/2020 Church et al.
2021/0038802 A1 2/2021 Madsen
2021/0052804 A1 2/2021 Madsen
2021/0187020 A1 6/2021 Corash et al.
2021/0260114 A1 8/2021 Corash et al.
2021/0322479 A1 10/2021 Vermeij
2022/0031917 A1 2/2022 Cahyadi et al.
2023/0226232 A1 7/2023 Church et al.
2024/0108767 A1 4/2024 Church
2024/0350687 A1 10/2024 Church
2025/0345471 A1 11/2025 Church et al.
2026/0048161 A1 2/2026 Church et al.

FOREIGN PATENT DOCUMENTS

CN 203017432 U 6/2013
CN 105412960 A 3/2016
CN 106421864 A 2/2017
CN 107075478 A 8/2017
CN 107852359 A 3/2018
EP 1181061 B1 8/2006
EP 3009946 A1 4/2016
JP 2006501978 A 1/2006
JP 2006505349 A 2/2006
JP 2011036683 A 2/2011
JP 5344735 B2 11/2013
JP 2015042266 A 3/2015
JP 2015171440 A 10/2015
JP 2017029717 A 2/2017
JP 2017077247 A 4/2017
JP 2017153966 A 9/2017
JP 2017184725 A 10/2017
JP 2019037450 A 3/2019
WO 199300005 A1 1/1993
WO 199317553 A1 9/1993
WO 199403054 A1 2/1994
WO 199420090 A1 9/1994
WO 199427433 A1 12/1994
WO 199428120 A1 12/1994
WO 199500141 A1 1/1995
WO 199512973 A1 5/1995
WO 199519705 A1 7/1995
WO 199608965 A1 3/1996
WO 199614737 A1 5/1996
WO 199614739 A1 5/1996
WO 199614740 A1 5/1996
WO 199639815 A1 12/1996
WO 199639818 A1 12/1996
WO 199639820 A1 12/1996
WO 199640857 A1 12/1996
WO 199721346 A1 6/1997
WO 199737536 A1 10/1997
WO 199818908 A1 5/1998
WO 199830327 A1 7/1998
WO 199830545 A1 7/1998
WO 199903976 A2 1/1999
WO 199903976 A3 5/1999
WO 199926476 A1 6/1999
WO 199934839 A1 7/1999
WO 199934914 A1 7/1999
WO 199934915 A1 7/1999
WO 199959645 A1 11/1999
WO 199963981 A2 12/1999
WO 199963981 A3 4/2000
WO 200074731 A1 12/2000
WO 200191775 A2 12/2001
WO 200191775 A3 6/2002
WO 02053209 A1 7/2002
WO 2003047650 A2 6/2003
WO 2003049784 A2 6/2003
WO 2003049784 A3 6/2003
WO 2003061379 A2 7/2003
WO 2003065787 A2 8/2003
WO 2003078023 A1 9/2003
WO 2003061379 A3 10/2003
WO 2003090794 A1 11/2003
WO 2003065787 A3 12/2003
WO 2003047650 A3 2/2004
WO 2004018471 A1 3/2004
WO 2004033081 A2 4/2004
WO 2004044810 A1 5/2004
WO 2004033081 A3 6/2004
WO 2004049914 A2 6/2004
WO 2004050029 A2 6/2004
WO 2004050848 A2 6/2004
WO 2004050897 A2 6/2004
WO 2004050897 A3 8/2004
WO 2004050029 A3 10/2004
WO 2004084936 A2 10/2004
WO 2004050848 A3 12/2004
WO 2004110481 A2 12/2004
WO 2004049914 A3 2/2005
WO 2005009463 A2 2/2005
WO 2004110481 A3 3/2005
WO 2005037233 A2 4/2005
WO 2004084936 A3 6/2005
WO 2005009463 A3 6/2005
WO 2005067460 A2 7/2005
WO 2005071088 A2 8/2005
WO 2005092372 A2 10/2005
WO 2005071088 A3 11/2005
WO 2005037233 A3 1/2006
WO 2006021314 A2 3/2006
WO 2006050328 A1 5/2006
WO 2005092372 A3 6/2006
WO 2005067460 A3 10/2006
WO 2007022511 A2 2/2007
WO 2007022520 A2 2/2007
WO 2007022520 A3 5/2007
WO 2007022511 A3 9/2007
WO 2007103225 A2 9/2007
WO 2007103261 A2 9/2007
WO 2007117371 A2 10/2007
WO 2007103225 A3 5/2008
WO 2007103261 A3 12/2008
WO 2007117371 A3 12/2008
WO 2008156813 A1 12/2008
WO 2009126786 A2 10/2009
WO 2009126786 A3 7/2010
WO 2011120172 A1 10/2011
WO 2012018484 A2 2/2012
WO 2012018484 A3 2/2012
WO 2012071135 A2 5/2012
WO 2012071135 A3 5/2012
WO 2014022717 A1 2/2014
WO 2014051882 A1 4/2014
WO 2014051906 A1 4/2014
WO 2015168783 A1 11/2015
WO 2016014854 A1 1/2016
WO 2016057965 A1 4/2016
WO 2016115535 A1 7/2016
WO 2016149055 A2 9/2016
WO 2016149055 A3 12/2016
WO 2016210374 A1 12/2016
WO 2017009534 A1 1/2017
WO 2017047119 A1 3/2017
WO 2017062260 A2 4/2017

(56) References Cited

FOREIGN PATENT DOCUMENTS

| | | | |
|---|---|---|---|
| WO | 2017062260 | A3 | 4/2017 |
| WO | 2017070619 | A1 | 4/2017 |
| WO | 2017120545 | A2 | 7/2017 |
| WO | 2017120545 | A3 | 8/2017 |
| WO | 2018119462 | A1 | 6/2018 |
| WO | 2018125994 | A1 | 7/2018 |
| WO | 2018161020 | A1 | 9/2018 |
| WO | 2019060610 | A1 | 3/2019 |
| WO | 2019133929 | A1 | 7/2019 |
| WO | 2020061537 | A1 | 3/2020 |
| WO | 2020263745 | A1 | 12/2020 |
| WO | 2020263759 | A2 | 12/2020 |
| WO | 2020264421 | A1 | 12/2020 |
| WO | 2020263759 | A3 | 1/2021 |

OTHER PUBLICATIONS

International Preliminary Report on Patentability, issued Apr. 13, 2023 for PCT Application No. PCT/US2021/071920, filed Oct. 18, 2021, 7 pages.

Oxford English Dictionary (Date Unknown). "System," located at https://www.oed.com/search/dictionary/?scope=Entries&q=system&tl=true, last visited on Sep. 26, 2023, one page.

Alhumaidan, H. et al. (2012). "Current Status of Additive Solution for Platelets," J. Clin Apheresis 27:93-98.

International Preliminary Report on Patentability, issued Dec. 28, 2021, for PCT Application No. PCT/US2020/039011, filed Jun. 22, 2020, 13 pages.

International Preliminary Report on Patentability, issued Dec. 28, 2021, for PCT Application No. PCT/US2020/039984, filed Jun. 26, 2020, 8 pages.

International Preliminary Report on Patentability, issued Jun. 30, 2020, for PCT Application No. PCT/US2018/068048, 11 pages.

International Preliminary Report on Patentability, issued mailed Dec. 28, 2021, for PCT Application No. PCT/US2020/038950, filed Jun. 22, 2020, 9 pages.

International Search Report and Written Opinion, mailed Aug. 19, 2002, for PCT Application No. PCT/US2020/038950, filed Jun. 22, 2020, 16 pages.

International Search Report and Written Opinion, mailed Dec. 23, 2020, for PCT Application No. PCT/US2020/039011, filed Jun. 22, 2020, 18 pages.

International Search Report and Written Opinion, mailed Jan. 17, 2022, for PCT Application No. PCT/US2021/0071920, filed Oct. 18, 2021, 14 pages.

International Search Report and Written Opinion, mailed May 3, 2019, for PCT Application No. PCT/US2018/068048, filed on Dec. 28, 2018 18 pages.

International Search Report and Written Opinion, mailed Sep. 29, 2020, for PCT Application No. PCT/US2020/039984, filed Jun. 26, 2020, 14 pages.

Irsch, J et al. (2011, e-pub. Jan. 27, 2011). "Pathogen Inactivation of Platelet and Plasma Blood Components for Transfusion Using the Inercept Blood System™," Transfus. Med. Hemother. 38:19-31.

Prodouz, K.N. et al. (1992). "Effects of Two Viral Inactivation Methods on Platelets: Laser-UV Radiation and Merocyanie 540-Mediated Photoinactivation," Blood Cells 18(1): 101-116.

Prowse, C.V. (Apr. 2013, e-pub. Nov. 8, 2012). "Component Pathogen Inactivation: A Critical Review," Vox Sanguinis, 104(3):183-199.

Reikvam, H. et al. (2010). "The Mirasol® Pathogen Reduction Technology System and Quality of Platelets Stored in Platelet Additive Solution," Blood Transfus. 8:186-192.

Ringwald, J. et al. (Apr. 2006). "The New Generation of Platelet Additivie Solution for Storage at 22: Development and Current Experience," Transfusion Medicine Reviews, 20(2):158-164.

Schlenke, P. (2014, e-pub. Jul. 21, 2014). "Pathogen Inactivation Technologies for Cellular Blood Components: an Update," Transfus. Med. Hemother. 41:309-325.

Schlenke, P. et al. (2008). "Photochemical Treatment Of Plasma With Amotosalen and UVA Light: Process Validation In Three European Blood Centers," Transfusion 48:697-705, 9 pages.

Seltsam, A. et al. (2011, e-pub. Jan. 22, 2011). "UVC Irraditation For Pathogen Reduction of Platelet Concentrates and Plasma," Transfusion Medicine and Hemotherapy 38:43-54.

Sofer, G. (Aug. 2002). "Virus Inactivation In The 1990s—and Into the 21st Century: Part 2, Red Blood Cells and Platelets," BioPharm pp. 42-49.

U.S. Appl. No. 09/238,355, Greenman, W. et al., filed on Jan. 27, 1999. (Copy not submitted herewith pursuant to the waiver of 37 C.F.R. § 1.98(a)(2)(iii) issued by the Office on Sep. 21, 2004.).

U.S. Appl. No. 17/451,311, Church, D. et al., filed on Oct. 18, 2021. (Copy not submitted herewith pursuant to the waiver of 37 C.F.R. § 1.98(a)(2)(iii) issued by the Office on Sep. 21, 2004.).

1524

1526

1526

MODULAR LIGHT DEVICE FOR A BIOLOGICAL FLUID TREATMENT SYSTEM

CROSS REFERENCE TO RELATED APPLICATIONS

This application claims the priority of U.S. Provisional Application No. 63/093,722 filed on Oct. 19, 2020, the entire contents of which is incorporated herein by reference.

FIELD OF THE DISCLOSURE

This disclosure relates generally to systems, methods, and devices for treating biological fluids, including mixtures of biological fluids and photochemical agents, with light, and more specifically to a modular light device architecture for use in a biological fluid treatment system.

BACKGROUND OF THE DISCLOSURE

Systems and methods for treating biological fluids with light are well known. For example, U.S. Pat. Nos. 7,459,695, 6,986,867, and 5,593,823 describe a system for treating a biological fluid with light to inactivate pathogens in the biological fluid. Light is emitted within a selected range of wavelengths that are effective to inactivate pathogens in the biological fluid, particularly by photochemical inactivation of pathogens. Other systems and methods for treating biological fluids with light may include, for example, systems and methods described in U.S. Pat. Nos. 6,843,961, 7,829,867, 9,320,817 and 8,778,263, WO2019133929A1, and Schlenke, 2014, Transfus. Med. Hemother. 41:309-325.

For blood products including for example, platelets and plasma components and their derivatives, it is important to ensure that the blood products are free of pathogens to minimize the risk of infecting an individual receiving a blood product. Testing for the presence of a pathogen in blood is limited by the pathogens for which tests are available and assay sensitivity. As an alternative or supplement to testing for pathogens, methods are known in the art for inactivating pathogens using various compound (e.g., chemical, photochemical)-based inactivation methods to reduce the risk of transfusion-transmitted infection (e.g., as disclosed in Schlenke et al., Transfus Med Hemother, 2014, 41, 309-325 and Prowse, Vox Sanguinis, 2013, 104, 183-199). Photochemical pathogen inactivation systems based on psoralens and ultraviolet light for treating blood products include the commercially available INTERCEPT® Blood System (Cerus Corporation), which utilizes disposable processing sets and an ultraviolet illumination device (INT-100). Blood products such as plasma or platelets are mixed with a psoralen, amotosalen, in the processing sets and then illuminated with ultraviolet A light. Multiple different disposable processing sets may be used, depending on the type of blood product to be treated and particular properties of those blood products, such as for example volume and platelet number.

Treating biological fluids with light to inactivate pathogens in the biological fluid can require delivering a precise amount (e.g., dose) of a desired type of light (e.g., ultraviolet light), uniformly, to the entire biological fluid. Thus, in one or more examples, an electronic device configured to treat biological fluids can often include a dedicated light source component located internally within the electronic device that can be configured to deliver a specific amount of light to the biological sample being treated. The dedicated light source component should be configured to deliver a precise amount of light while the electronic device maintains a number of critical operating requirements such as temperature, power consumption, and footprint. The architecture and layout of the dedicated light source component can therefore be critical to ensuring that the light source component is able to meet the requirements necessary to effectively inactivate pathogens in a biological fluid. For instance, a specific amount of ultraviolet light (e.g., in conjunction with a pathogen inactivation compound) may be required to be delivered to a biological fluid for a certain duration of time and intensity to ensure that the UV light can effectively cross-link nucleic acids of the pathogen irreversibly, thereby rendering the pathogens inactive. The light source component therefore must be designed to meet the necessary requirements for pathogen inactivation, while at the same time meeting other necessary design requirements to ensure that the electronic device overall is commercially viable.

In view of the precise specification to which a light source components must operate, and the need for the light source components to be replaced (perhaps multiple times during the lifetime of a treatment device), there is an unmet need for implementing light source components so that it can operate to precise electrical and mechanical requirements while at the same time providing a modular design that can make the light device easily replaceable should the need arise.

SUMMARY OF THE DISCLOSURE

Designing the light source components of an electronic treatment device to meet specific requirements can present many challenges. For instance, the requirements imposed on a light source component can require that the light source component include not only the light sources used to illuminate a sample, such as for example a biologic fluid, but also can include various sensors, electrical controls, and other safety features that are necessary to keep the light source component operating in a safe manner and according to its specifications. During the lifetime of an electronic device, the light source components' performance may degrade due to light source decay and/or burnt out light sources (e.g., light emitting diodes (LEDs)), life expectancy of light sources, or other unintended operating circumstances that render the light source component unsatisfactory for its intended purpose. However, while the light source component may not be operating according to its requirements, the rest of the electronic device may be operating normally. It would therefore be cost-ineffective to simply replace the entire electronic device, but instead be more pragmatic to simply replace the one or more malfunctioning components of the light source. However, accessing single components of the light source may be complex and an inefficient use of resources. Instead of replacing single components of the light source, one option is to simply replace the entire light device. However, if the light device is integrated into the electronic device in such a way that makes its removal difficult or require significant time and resources, then any time a single component of the light device fails, the customer or user of the device may experience significant delays in returning the device to working condition or may expend significant resources to make the repair. Furthermore, replacing the light source components may require complex mechanical and electrical procedures to ensure that the replacement light source components when installed operates in conjunction with the other components of the device. However, if the light source components require complicated procedures to be replaced, then it may not be cost-effective to simply replace the light source components should it malfunction or otherwise be unsatisfactory for use in a treatment device.

In some embodiments, the present disclosure provides a modular light device for use in conjunction with an electronic device (e.g. electronic treatment device) for treating a biological fluid, wherein the modular light device includes a plurality of components collectively configured to transmit light to one or more biological fluids for treatment, the modular light device comprising: a housing configured to house one or more components of the modular light device; a light source array chamber configured to transmit light (e.g., ultraviolet (UV) light, of a selected wavelength (e.g., peak wavelength)), wherein the light source array chamber comprises: one or more light source arrays, each comprising a plurality of light sources configured to generate UV light; and one or more light sensors configured to detect (e.g., measure) light; a window portion (e.g., window opening, transparent window, transmissive window) located on the modular light device (i.e., on or in) configured to pass UV light generated by the plurality of light sources to the one or more biological fluids for treatment; a driver (e.g., light source driver) communicatively coupled to one or more components of the modular light device (e.g., light source array chamber of the modular light device) and configured to operate the one or more components; and a controller communicatively coupled to the driver (e.g., light source driver) and configured operate the driver (e.g., light source driver).

In some embodiments, the modular light device light source array chamber comprises one or more temperature sensors configured to measure a temperature (e.g., of the light device).

In some embodiments, each light source of the plurality of light sources emits light having a full-width half-maximum (FWHM) spectral bandwidth of less than 20 nanometers.

In some embodiments, each light source of the plurality of light sources is a light-emitting diode (LED).

In some embodiments, the one or more light source arrays each comprises a respective first light source channel configured to emit ultraviolet light with a first peak wavelength of the array.

In some embodiments, the electronic device comprises a treatment chamber configured to receive (e.g., hold, carry) at least one of the one or more biological fluids (e.g., for treatment).

In some embodiments, the modular light device is configured to be positioned within the electronic device to transmit light to one or more biological fluids in a treatment chamber of the electronic device.

In some embodiments, the housing is configured to mechanically interface with the electronic device so as to mechanically secure the modular light device when placed into the electronic device. In some embodiments, the housing comprises one or more tracks configured to mechanically interface with one or more rails of the electronic device so as to mechanically secure the modular light device when placed into the electronic device.

In some embodiments, the one or more tracks are configured to allow the modular light device to be slideably moveable so to remove and insert the modular light device into the electronic device.

In some embodiments, the modular light device comprises one or more heat exchangers configured to transfer heat away from the light source array and/or the modular light device.

In some embodiments, the one or more heat exchangers are fin shaped.

In some embodiments, the one or more heat exchangers are configured to exchange heat with air that is passed across (e.g., blown across, moved across) the one or more heat exchanges to transfer heat away from the light source array and/or the modular light device.

In some embodiments, the one or more heat exchangers are configured to exchange heat with air that is pulled across the one or more heat exchangers by one or more fans positioned in the electronic device.

In some embodiments, the light device comprises one or more fans configured to pass (e.g., blow, pull, move) air across the one or more heat exchangers so as to remove the heat transferred by the one or more heat exchangers.

In some embodiments, the window portion is an opening in modular light device (e.g., opening in the housing of a modular light device, opening to the light source array chamber of a modular light device).

In some embodiments, the window portion comprises a window material covering or enclosing an opening in the modular light device (e.g., opening in the housing of a modular light device, opening to the light source array chamber of a modular light device).

In some embodiments, the window portion (e.g., window material) is made of glass.

In some embodiments, wherein the window portion (e.g., window material) is made of a polymeric material (e.g., a plastic).

In some embodiments, the window portion is at least 80% transmissive for UV light of a selected wavelength.

In some embodiments, the window portion is at least 90% transmissive for UV light of a selected wavelength.

In some embodiments, the modular light device comprises one or more light sensors disposed on the window portion and configured to detect (e.g., measure) light generated by the modular light device (e.g., by one or more light source arrays of the modular light device, by one or more light sources of the modular light device).

In some embodiments, the modular light device comprises one or more circuits (e.g., flexible circuits) disposed at (e.g., on or across (at least partially)) the window portion, and wherein the one or more circuits (e.g., flexible circuits) comprises one or more light sensors disposed on the circuits (e.g., flexible circuits) and configured to detect (e.g., measure) light generated by the modular light device (e.g., by one or more light source arrays of the modular light device, by one or more light sources of the modular light device).

In some embodiments, the light source array chamber includes a plurality of reflector panels disposed along one or more edges of the light source array chamber.

In some embodiments, the plurality of reflector panels are disposed in the light source array chamber so as to minimize a loss of light energy at a perimeter of the light source array chamber.

In some embodiments, one or more light sensors of the light source array chamber are oriented so as to detect (e.g., measure) light generated by a separate modular light device (e.g., positioned on a light source array so as to detect (e.g., measure) light generated by a separate modular light device).

In some embodiments, the one or more light sensors are implemented using photodiodes.

In some embodiments, the one or more temperature sensors are implemented using thermistors.

In some embodiments, one or more of the one or more temperature sensors are configured to measure a temperature at a junction between a light source of the one or more light sources and a printed circuit board (PCB) (of the light source array) on which the light source is disposed upon.

In some embodiments, the plurality of light sources are configured to generate UV-A light.

In some embodiments, the plurality of light sources are configured to generate light with a first peak wavelength from about 315 nm to about 350 nm. In some embodiments, the plurality of light sources are configured to generate light with a first peak wavelength from about 315 nm to about 335 nm. In some embodiments, the plurality of light sources are configured to generate light with a first peak wavelength from about 320 nm to about 330 nm. In some embodiments, the plurality of light sources are configured to generate light with a first peak wavelength from about 330 nm to about 350 nm. In some embodiments, the plurality of light sources are configured to generate light with a first peak wavelength from about 340 nm to about 350 nm. In some embodiments, the plurality of light sources are configured to generate light with a first peak wavelength within a range of 345±5 nm.

In some embodiments, the plurality of light sources are configured to generate UV-B or UV-C light.

In some embodiments, the one or more arrays of light sources each comprises a respective second light source channel configured to emit ultraviolet light with a second peak wavelength of the array, wherein the second peak wavelength differs from the first peak wavelength by at least 5 nanometers.

In some embodiments, the one or more arrays of light sources each comprises a respective first light source channel configured to emit ultraviolet light with a first peak wavelength of the array in the UV-A spectrum, and a respective second light source channel configured to emit ultraviolet light with a second peak wavelength of the array in the UV-B or UV-C spectrum.

In some embodiments, the housing comprises one or more electronic interfaces configured to communicatively couple the modular light device to the electronic device.

In some embodiments, the one or more electronic interfaces includes an interlock connection configured to allow the electronic device to turn off the modular light device.

In some embodiments, the one or more electronic interfaces includes a communications port configured to allow the electronic device to transmit commands to the modular light device, and configured to allow for the modular light device to transmit data to the electronic device.

In some embodiments, the one or more electronic interfaces includes a power port configured to transmit power from the electronic device to the modular light device.

In some embodiments, a number of light sources of the light source array chamber is configured to provide light (e.g., transmit light) for a pre-determined illumination volume (e.g., density) to the one or more biological fluids.

In some embodiments, the one or more light sources of the light source array chamber collectively generate a substantially uniform dose (e.g., amount) of light (e.g., at the surface of the biological fluid, at a plane within a volume of the biological fluid, that is transmitted from the modular light device, within an illumination volume). In some embodiments, the one or more light sources of the light source array chamber collectively generate a substantially uniform irradiance (e.g., at or across the surface of the biological fluid (e.g., container with the biological fluid), within an illumination volume, that is transmitted from the modular light device). In some embodiments a variance in the irradiance of the light across a surface of the biological fluid is less than 25%. In some embodiments, the one or more light sources of the light source array chamber collectively illuminate any 5 $cm^2$ area on the biological fluid (e.g., container with biological fluid) with less than 25% variance from the integrated irradiance (averaged over surface area) of the entire biological fluid (e.g., container with biological fluid) intercept plane.

In some embodiments, the one or more light sources of the light source array chamber are LEDs configured to have a beam angle (e.g., beam width) of about 110 degrees to about 130 degrees. In some embodiments, the one or more light sources of the light source array chamber are LEDs configured to have a beam angle (e.g., beam width) of about 120 degrees.

In some embodiments, a dose of light delivered from the modular light device to a biological fluid during a treatment process is based on (e.g., based in part on, based at least in part on) light detected (e.g., measured) by one or more of the one or more light sensors.

In some embodiments, an amount of time that the modular light device is activated (e.g., emitting light) during a treatment process is based on (e.g., based in part on, based at least in part on) light detected (e.g., measured) by one or more of the one or more light sensors. In some embodiments, the amount of time that the modular light device is activated is an amount of time that the one or more light sources are activated (e.g., emitting light). In some embodiments, the amount of time that the modular light device is activated is an amount of time that the one or more light sources are activated in each cycle of a pulse width modulation (e.g., pulse width modulation cycle). In some embodiments, the amount of time that the modular light device is activated is a cumulative amount of time that the one or more light sources are activated by pulse width modulation during a treatment process.

In some embodiments, an intensity of light generated by the modular light device during a treatment process is based on (e.g., based in part on, based at least in part on) light detected (e.g., measured) by one or more of the one or more light sensors. In some embodiments, the intensity of light generated by the modular light device during a treatment process can be a function of pulse width modulation applied to the one or more light sources (e.g., based on light detected by one or more of the one or more light sensors).

In some embodiments, the electronic device for treating a biological fluid comprises a first modular light device (e.g., in a treatment chamber of the electronic device) oriented to face a biological fluid to be treated, and wherein the first modular light device delivers (e.g., is configured to deliver) light to the biological fluid for treatment (e.g., deliver an amount or dose of light, deliver a predetermined or specified amount or dose of light). In some embodiments, the electronic device for treating a biological fluid comprises a first modular light device and a second modular light device (e.g., in a treatment chamber of the electronic device), the first and second modular light devices oriented to face one another (e.g., each positioned to face a biological fluid to be treated), and wherein the first and second modular light devices collectively deliver light to a biological fluid for treatment. In some embodiments, the biological fluid contains (e.g., is admixed with) a photochemical compound (e.g., a pathogen inactivation compound).

In some embodiments, the first and second light devices are configured to perform a test (e.g., operational test, integrity test, health test) comprising: transmitting light from the first modular light device; detecting (e.g., measuring) the light transmitted by the first device by one or more light sensors of the second modular light device; determining the presence or absence of one or more occlusions (e.g., obstructions, impediments) to the light transmitted by the first modular light device, by comparing the detected light to a pre-determined amount of light (e.g., comparing to a baseline amount of light, comparing to determine a reduction (e.g., partial reduction, blocking) in the light compared to the pre-determined level). In some embodiments, the test further comprises determining a baseline amount of light transmitted by the first modular light device (e.g., transmitted to the second modular light device). In some embodiments, the test further comprises calibrating the first modular light device and setting a baseline amount of light transmitted by the first modular light device.

In some embodiments, the test further comprises: transmitting light from the second modular light device; detecting (e.g., measuring) the light transmitted by the second modular light device by one or more light sensors of the first modular light device; determining the presence or absence of one or more occlusions (e.g., obstructions, impediments) to the light transmitted by the second modular light device, by comparing the detected light to a pre-determined level of light (e.g., comparing to a baseline amount of light, comparing to determine a reduction (e.g., partial reduction, blocking) in the light compared to the pre-determined level). In some embodiments, the test further comprises: determining a baseline amount of light transmitted by the second modular light device (e.g., transmitted to the first modular light device). In some embodiments, the test further comprises calibrating the second modular light device and setting a baseline amount of light transmitted by the second modular light device.

In some embodiments, the test is a test to determine the presence of obstructed light path in the electronic device (e.g., scratch or foreign material (e.g., dust) on a window of the modular light engine or on a platform/tray in the electronic device).

In some embodiments, the test is a test to determine the presence of a biological sample to be treated in the electronic device.

In some embodiments, the modular light device is configured to perform a test (e.g., operational test, integrity test, health test) comprising: transmitting light from one or more light source arrays of the light source array chamber of the modular light device; detecting the light transmitted by the one or more light source arrays by one or more light sensors of the modular light device (e.g., of the light source array chamber of the modular light device); comparing the detected light to a pre-determined amount of light (e.g., to determine a reduction/change in the light compared to the pre-determined amount). In some embodiments, the one or more light sensors are light sensors disposed on the window portion (e.g., disposed on circuits disposed on the window portion) of the modular light device.

In some embodiments, the test further comprises comparing the detected light to a pre-determined amount of light.

In some embodiments, the test further comprises determining the integrity (e.g., functional integrity, health, operating condition) of one or more (e.g., each) of the one or more sensors (e.g., by comparing to each other, by comparing to a baseline or standard).

In some embodiments, the test further comprises determining the integrity (e.g., functional integrity, health, operating condition) of one or more (e.g., each) light sources of the one or more light source arrays (e.g., by comparing to each other, by comparing to a baseline or standard).

In some embodiments, the modular light devices is configured to perform a calibration process comprising: transmitting light from one or more light source arrays of the modular light device; detecting the light transmitted by the light source array(s) of the modular light device by one or more light sensors of a calibration device (e.g., radiometer) external to the modular light device, the calibration device positioned within the electronic device; comparing the detected light to a pre-determined amount of light; and adjusting (e.g., adjusting the intensity of) one or more light sources of the light source array(s). In some embodiments, adjusting (e.g., adjusting the intensity of) one or more light sources of the light source array(s) is by adjusting individual light sources. In some embodiments, adjusting (e.g., adjusting the intensity of) one or more light sources of the light source array(s) is by adjusting a light source channel. In some embodiments, adjusting (e.g., adjusting the intensity of) one or more light sources of the light source array(s) is by adjusting the light source array.

In another aspect of the present disclosure, a method for treating a biological fluid comprises: providing the biological fluid; and illuminating the biological fluid with one or more modular light devices of any one of the above embodiments, for a duration and at an intensity sufficient to inactivate a pathogen in the biological fluid.

In some embodiments, a method for treating a biological fluid comprises: providing the biological fluid in admixture with a pathogen inactivation compound; and illuminating the biological fluid with one or more modular light devices of any one of above embodiments, for a duration and at an intensity sufficient to inactivate a pathogen in the biological fluid.

BRIEF DESCRIPTIONS OF THE DRAWINGS

DETAILED DESCRIPTION

Figure 1:
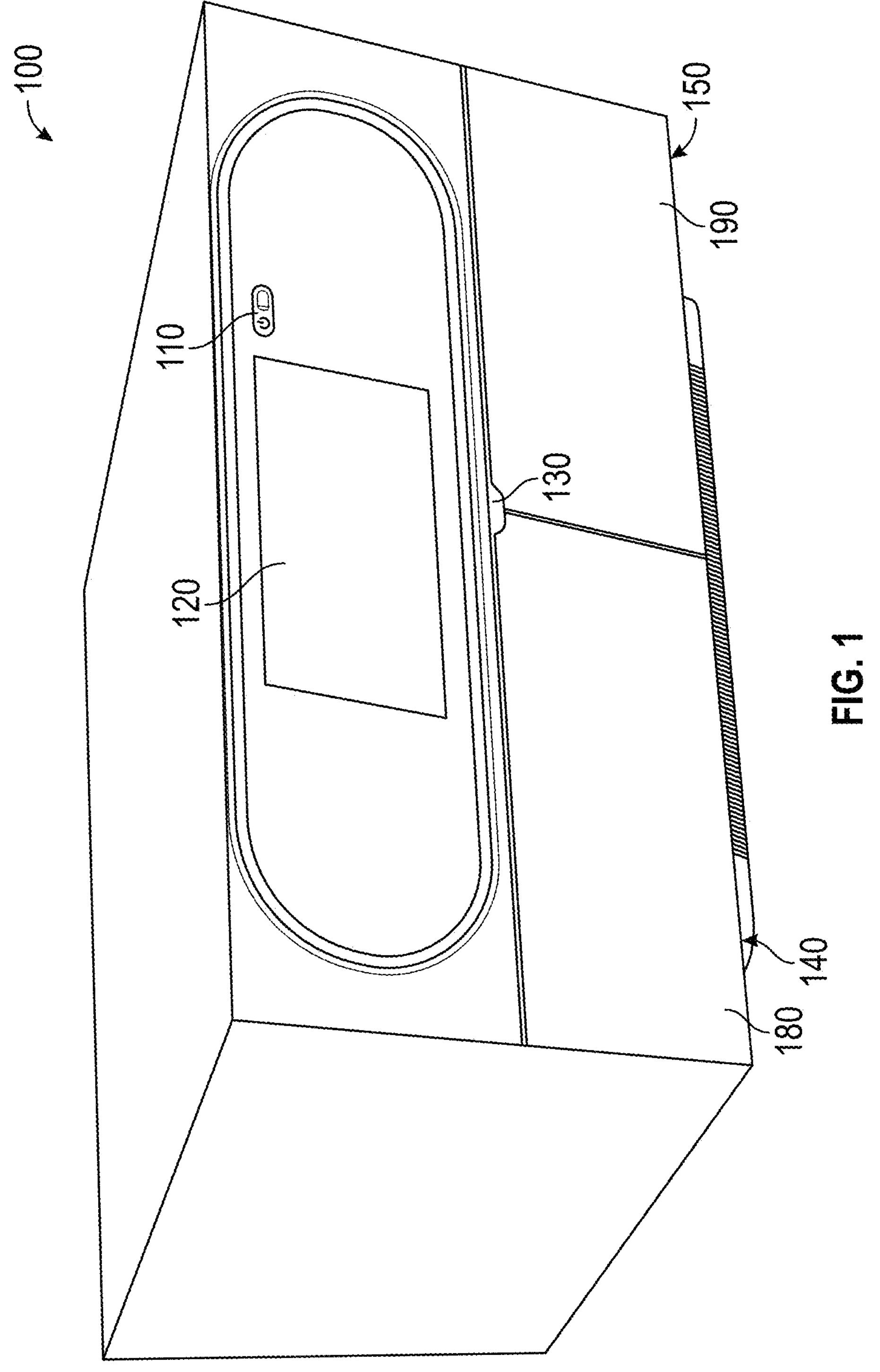
FIG. 1 illustrates an exemplary device for treating biological fluids according to examples of the disclosure.

The following description sets forth exemplary methods, parameters, and the like. It should be recognized, however, that such description is not intended as a limitation on the scope of the present disclosure but is instead provided as a description of exemplary embodiments.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a," "an," and "the" used in the following description are intended to include the plural forms as well unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices without loss of generality.

However, all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

Certain aspects of the present invention may include process steps and instructions described herein in the form of an algorithm. It should be noted that the process steps and instructions of the present invention could be embodied in software, firmware, or hardware, and, when embodied in software, they could be downloaded to reside on, and be operated from, different platforms used by a variety of operating systems.

FIG. 1 illustrates an exemplary system 100 for treating biological fluids. As used herein, a "biological fluid" refers to any fluid that is found in or derived from an organism (e.g., human, animal, plant, microorganism), or that comprises one or more components (e.g., biologics) found in, isolated from, or derived from an organism, including synthetic versions (e.g., including variants) thereof. Biological fluids may include, but are not limited to, blood and blood products, vaccines, cells (e.g., primary cells, cell lines, cell cultures), natural and recombinant peptides or proteins (e.g., therapeutics, antibodies), bacterial cultures, virus suspensions and the like. As used herein, "blood product" refers to blood (e.g., whole blood) or a component or derivative of blood such as, for example, red blood cells, white blood cells, platelets, plasma or components thereof (e.g., coagulation factors, albumin, fibrinogen), cryoprecipitate and cryo-poor (e.g., cryo-reduced) plasma, or a combination of one or more of such components that have been separated from blood. In one more examples, a biological fluid may further comprise a non-biological fluid, such as for example, a physiological solution (e.g., diluent solution), including but not limited to saline, buffered solution, nutrient solution, platelet additive solution (PAS) and/or anticoagulant solution. In one more examples, when the biological fluid is positioned (e.g., the biological fluid is in a container, such as a treatment bag positioned or carried on a platform) in a chamber (not shown) of the biological fluid treatment system, the biological fluid is illuminated by light (e.g., visible light, ultraviolet light) having a certain spectral profile at specified intensities for a determined time period.

System 100 includes a power switch 110, display 120, scanner 130, platform 140, and platform 150. Although system 100 in FIG. 1 includes the described elements, examples of system 100 can include different combinations of the described elements or additional elements without departing from the scope of the disclosure. In some examples, the system 100 can couple, via a wired or a wireless connection, to a computing device (e.g., computer, mobile device) (not shown).

In some examples, in response to an input to the power switch 110, power is provided to the system 100. For example, the power switch 110 can be mechanical button. When the system 100 is off, in response to a push of the power switch 110, power is provided to the system 100 (e.g., the system 100 turns on). When the system 100 is on, in response to a push of the power switch 110, the provided power to the system 100 ceases (e.g., the system 100 turns off). In some examples, during treatment, the system 100 stays on and does not turn off in response to a push of the power switch.

As another example, the power switch 110 can be a capacitive switch that can be activated with a touch input (e.g., by placing a user's finger on the power switch). As yet another example, the power switch can be a button having two or more states. The power switch can be at an "off" state when the power switch is at a first position (e.g., unpressed, flipped to a first side). The power switch can be at an "on" state when the power switch is at a second position (e.g., pressed, flipped to a second side).

In some examples, the display 120 is a touchscreen. For example, the display 120 can be a capacitive touchscreen or a resistive touchscreen. In some examples, the display 120 is configured to display a graphical user interface (GUI) for operating the system 100. In some embodiments, the display 120 is configured to receive input from the scanner 130. In one more examples, the display 120 is configured to receive input on the GUI. For example, a GUI object of a plurality of GUI objects displayed on the GUI can be selected by providing a user's manual input (e.g., touch or hover input) on the touchscreen. In response to receiving the input, the system 100 can perform an operation associated with the selected GUI object. For example, a GUI object may be associated with initiation of a biological fluid treatment, and in response to receiving an input selecting the GUI object, the system 100 initiates a process to treat a biological fluid. In one more examples, the display 120 is configured to display instructions to a user operator (e.g., operator instructions) on the GUI. In some embodiments, the display 120 is configured to display input from the scanner 130 to a user operator. In some embodiments, the display 120 is configured to display input from sound that is detected by an audio input (e.g., one or more microphones) and processed (e.g., speech-to-text conversion) by one or more processors into a visual form (e.g., command text, command code) on the display 120 that the user can recognize as an input command, such as for example a user's voice command that is detected by one or more microphones (e.g., located in any arrangement internal to, external to, and/or part of the exterior housing of the system 100) and converted by one or more processors into command text on the display 120 that the user can recognize as an input command. In some embodiments, the display 120 is configured to display input from a user's visual motion (e.g., hand motion or gesture, object in a swiping motion) that is detected by a motion sensor (e.g., one or more cameras) and processed (e.g., motion-to-text conversion, motion-to-graphic conversion) by one or more processors into a visual form (command text, command code, command icon, command graphic) on the display 120 that the user can recognize as an input command, such as for example a user's hand gesture (e.g., hand in a swiping motion) that is detected by one or more cameras (e.g., located in any arrangement internal to, external to, and/or part of the exterior housing of the system 100) and converted by one or more processors into visual command text or a visual graphic on the display 120 that the user can recognize as an input command. Although one display 120 is illustrated in FIG. 1, the system 100 can include more than one display in some examples.

By using a touchscreen as an input component and/or input from the scanner 130, the user interface of system 100 can be simplified. For example, the use of a touchscreen can reduce the need for physical buttons corresponding to features that can be similarly performed using the touch screen. Biological fluid treatment using system 100 can be more efficient using the simplified user interface.

Although the power switch 110 and display 120 are described as elements of the system 100 that can be configured to receive user input, other elements or means of input can be included in the system 100 without departing from the scope of the disclosure. For example, the system 100 can include directional input keys, a mouse pad, or a scroll wheel configured for navigating a GUI displayed on the display 120. In some embodiments, the system 100 is configured to receive a user's input from sound that is detected by an audio input (e.g., one or more microphones) and processed (e.g., speech-to-text conversion) by one or more processors into a language form (e.g., command text, command code) that the system 100 can recognize as an input command, such as for example a user's voice command that is detected by one or more microphones (e.g., located in any arrangement internal to, external to, and/or part of the exterior housing of the system 100) and converted into command text by one or more processors that the system 100 can recognize as an input command. In some embodiments, the system 100 is configured to receive input from a user's visual motion (e.g., hand motion or gesture, object in a swiping motion) that is detected by a motion sensor (e.g., one or more cameras) and processed (e.g., motion-to-text conversion) by one or more processors into a language form (e.g., command text, command code), such as for example a user's hand gesture (e.g., hand in a swiping motion) that is detected by one or more cameras (e.g., located in any arrangement internal to, external to, and/or part of the exterior housing of the system 100) and converted into command text by one or more processors that the system 100 can recognize as an input command. Alternatively or in addition, system 100 can be configured to receive input other than user input, such as for example, from one or more sensors implemented for system 100. Non-limiting examples of various sensors that may be implemented (e.g., in a treatment chamber, with a light source component) include one or more light sensors configured to measure the light intensity at various portions of the treatment chamber and/or the light intensity incident on various portions of one or more biological fluids, one or more air flow sensors, one or more heat sensors for measuring the temperature of treatment chamber and/or the temperature of one or more biological fluids, one or more sensors for detecting the presence and/or type of one or more biological fluids (e.g. pressure sensors, optical retro-reflective sensors, optical transmissive sensors, label readers, scanners, barcode scanners, RFID sensors, etc.), one or more sensors for detecting a property (e.g., transmissivity) of the biological fluid (e.g., optical sensors, spectroscopic sensors), one or more sensors for detecting a photochemical compound in the biological fluid (e.g., fluorescence spectrometry), and one or more sensors (e.g., ultrasonic sensors) positioned to detect the fluid depth of a portion (e.g., various portions) of one or more biological fluids.

In some embodiments, system 100 can be configured to receive input from one or more scanners implemented for system 100. In some examples, the scanner 130 is configured to obtain information relating to biological fluids. In some examples, the scanner 130 can be configured to obtain identifying information related to the biological fluids to be treated. For example, the biological fluid may be stored in a container (e.g., hemocompatible bag, treatment bag) (not shown), and the container or other containers in a multi-container assembly (e.g., disposable fluid processing set) can include a tag or label or designated area containing the identifying information in some form, such as a visible form (e.g., a barcode, a QR code, etc.) and/or transmittable form (e.g., electronic identifier, radio frequency identification (RFID)). In some examples, the identifying information can represent information about the biological fluid product, such as biological or other parameters (e.g., donation ID, product code, set code, lot number, type of biological fluid, volume of biological fluid, content of biological fluid, for example platelet number) and treatment parameters. In some examples, the biological or other parameters, optionally in combination with input from one or more sensors and/or user inputs may determine a treatment parameter. In some, multiple sets of identifying information can be obtained. For example, multiple sets of identifying information may be located on one or more respective containers associated with (e.g., containing or part of a multi-container assembly containing) the biological fluid, and the sets of identifying information can be obtained from the respective containers by scanner 130. In some examples, the scanner may be a multi-scan scanner (e.g., camera with multi-scan functionality, camera in cooperation with circuitry (e.g., hardware and/or software) having multi-scan processing functionality, handheld scanner with multi-scan functionality, handheld scanner in cooperation with circuitry (e.g., hardware and/or software) having multi-scan processing functionality, label reader with multi-scan functionality, label reader in cooperation with circuitry (e.g., hardware and/or software) having multi-scan processing functionality) configured to sequentially or substantially simultaneously capture (e.g., acquire) multiple sets of identifying information (e.g., multiple barcodes, multiple QR codes, multiple labels, optical character recognition (OCR) of different strings or arrangements of alphanumeric text and/or symbols, image recognition, etc.) located on one or more containers, such as for example capturing multiple sets of identifying information in "batch" mode (e.g., in response to a single user input or a single device input that commands, triggers, or otherwise initiates a multi-scan operation that acquires multiple sets of identifying information). A single multi-scan operation may capture, sequentially or substantially simultaneously (e.g., simultaneously), multiple sets of identifying information (e.g., in a single operation, a camera can capture one or more images of one or more labels that show the multiple parameters of a biological product, such as for example donation ID, product code, set code, lot number, type of biological fluid, volume of biological fluid, content of biological fluid; in a single operation, a multi-scanner can perform one or more scans of one or more labels that show the multiple parameters above). In some embodiments, the multi-scanner or the system 100 is configured to recognize (and/or convert into another form recognized by the multi-scanner or system 100) the captured multiple sets of identifying information (e.g., recognizing (and/or deciphering) barcodes, QR codes, alphanumeric text and/or symbols, images) captured in a multi-scan operation. After capturing multiple sets of identifying information (e.g., in captured image(s), performed scan(s)), a multi-scanner can convey or communicate them (e.g., via a wired or wireless connection) to the system 100 in recognized (and/or converted) form (e.g., in a language form that the system 100 can already recognize, for example as parameter data) or in unrecognized form (e.g., captured image(s), performed scan(s)). If in unrecognized form, the system 100 can process the captured multiple sets of identifying information into a recognized form. The system 100 can assign the multiple sets of identifying information to corresponding fields (e.g., auto-populating information fields) of the GUI of the display 120 when displaying the GUI for the treatment chamber associated with the biological fluid to be treated. Thus, a multi-scan operation may provide data entry of all or most parameter data for a biological fluid into multiple specific data fields via an auto-population technique that may be convenient, efficient, and time-saving. For example, with a multi-scan operation, a user need not perform multiple scans in any particular order to capture multiple sets of identifying information that may be presented in a certain order (e.g., no need to perform a scan for each label on a container in the visual order of specific data fields presented on the GUI to the user.

In some example, the identifying information can enter a field of view of the scanner 130, and the scanner 130 can obtain the identifying information when the information is in the field of view. For example, a user can hold a biological fluid treatment container (e.g., bag) with a barcode facing the scanner 130, and the scanner 130 can image-capture, scan, or read the barcode; based on the obtained barcode, the system 100 can determine information about the biological fluid product. In some examples, the identifying information can enter a detection range of the scanner 130, and the scanner 130 can obtain the identifying information when the information is in the detection range. For example, a user can hold a biological fluid treatment bag with an RFID tag near the scanner 130, and the scanner 130 can detect the RFID tag; based on information obtained from the detected RFID tag, the system 100 can determine information about the biological fluid product.

Although the scanner 130 is illustrated as being located on an exterior of the system 100 in FIG. 1, the scanner 130 can be located at different locations of the system 100. In one more examples, the scanner 130 is located inside the system 100. For example, the scanner 130 can be located at a top of a treatment chamber of system 100. The scanner 130 can obtain information related to the biological fluid after the biological fluid is placed on a platform and/or in the chamber.

In some examples, the scanner 130 can be included in a device coupled to system 100. For example, the scanner 130 can be included in a handheld scanner (e.g., barcode scanner, QR code scanner) coupled to system 100. In some examples, a scanner 130 couples to system 100 via a wired connection. In some examples, a scanner 130 couples to system 100 via a wireless connection.

Although one scanner 130 is illustrated in FIG. 1, system 100 can include more than one scanner 130. For example, system 100 can include a plurality of treatment chambers, and each treatment chamber may have a corresponding scanner (e.g., internal scanner). As another example, system

100 can include a plurality of platforms and each platform may have a corresponding scanner (e.g., external scanner) located near or at an opening for a respective platform. As the platform moves through the opening, a container (e.g., treatment bag) containing the biological fluid can traverse a field of view of a respective scanner, and information, associated with the biological fluid, in visible form on the container or an associated container of a multi-container assembly can be obtained by the respective scanner. As another example, system 100 can include both a first scanner integrated with the system (e.g., positioned on an exterior of system 100, positioned in a treatment chamber of system 100), and a second scanner coupled to systems 100 (e.g., a handheld scanner).

In some examples, the platform 140 (e.g., drawer, tray, well, plate, stage) is configured to carry the biological fluid (e.g., a container containing the biological fluid) during treatment. In some examples, the platform is moveable (e.g., slideably moveable, configured to translate from inside the treatment chamber to outside the treatment chamber) between the interior and exterior of the treatment chamber (e.g., partially out of the treatment chamber). In some examples, the platform further comprises a first panel 180 movable between a closed position and an open position, wherein the first panel 180 covers a first opening to the first treatment chamber in the closed position, wherein the first panel 180 uncovers the first opening to the first treatment chamber in the open position. In some embodiments, the first panel is attached to, integrated with, or formed together with the platform 140 (e.g., in a drawer configuration). In some examples, the first panel 180 is a separate structure from the platform 140 (e.g., a separate hinged door that covers and uncovers the first opening to the first treatment chamber), and the platform 140 can slide in and out of the first treatment chamber separately from the first panel 180.

In some examples, the platform and/or first panel can be locked to remain in the closed position during treatment. The system 100 can prevent a user from prematurely accessing the content of the platform 140 (e.g., accessing the treatment chamber) during treatment by locking the first panel to remain in the closed position. In one more examples, the first panel can be locked by a pin (e.g., solenoid and pin) or magnetic lock mechanism. The system 100 can permit a user to access, by unlocking the first panel, the content of the platform 140 before and after treatment (e.g., to load the biological fluid on the platform 140, to unload the biological fluid from the platform 140) or after an input (e.g., an input on the GUI, an input to open latch, an input to a button switch).

As illustrated in FIG. 1, the structure of the platform 150 symmetrically mirrors structure of the platform 140 about a vertical axis. In one more examples, the platform 150 is substantially similar to platform 140 in size, shape, or orientation. As illustrated, the platforms 140 and 150 are arranged horizontally, such that the first biological fluid and the second biological fluid, when positioned on the first platform and on the second platform, respectively, are within a same plane. As the first panel 180 may be associated with the platform 140, as discussed above, a second panel 190 may be associated with the platform 150.

Although two platforms are illustrated in FIG. 1 as being a part of system 100, the system 100 can include one platform or more than two platforms that are substantially similar to platform 140 or platform 150 without departing from the scope of the disclosure. In general, the number of illustrated platforms and treatment chambers associated with systems 100-300 are exemplary; embodiments of systems 100-300 may include different numbers and combinations of platforms, treatment chambers, and their associated elements (e.g., scanners, light arrays, compartments) without departing from the scope of the disclosure. For example, in one or more examples, a system can include only one chamber with only one platform. In one or more examples, a system can include only one chamber with two or more platforms. In some embodiments, a system can include two chambers, each with only one platform. In some embodiments, a system can include two chambers, each with two or more platforms.

In some examples, the platform comprises a first compartment and a second compartment separate from the first compartment. In some examples, the first compartment is configured to hold (e.g., carry) a container (e.g., container of a multi-container assembly) containing a biological fluid in a position for illumination. In some examples, the second compartment is configured to hold a container (e.g., container of a multi-container assembly) not containing a biological fluid in a position not for illumination. In some examples, the platform is configured to separately carry at least a first container with a first biological fluid and a second container with a second biological fluid. In some examples, the platform is transparent (e.g., made of a material selected to transmit light of a selected wavelength, substantially transparent, >95% transparent, >90% transparent, >80% transparent, >80% transparent, >70% transparent, >60% transparent, >50% transparent) to light with a wavelength within 100 nm (e.g., 75 nm, 50 nm, 40 nm, 30 nm, 20 nm) of the peak wavelength of light used for illumination. In some example, the platform is transparent (e.g., substantially transparent, >95% transparent, >90% transparent, >80% transparent, >80% transparent, >70% transparent, >60% transparent, >50% transparent) to ultraviolet light (e.g., UV-A, UV-B, and/or UV-C).

Figure 2:
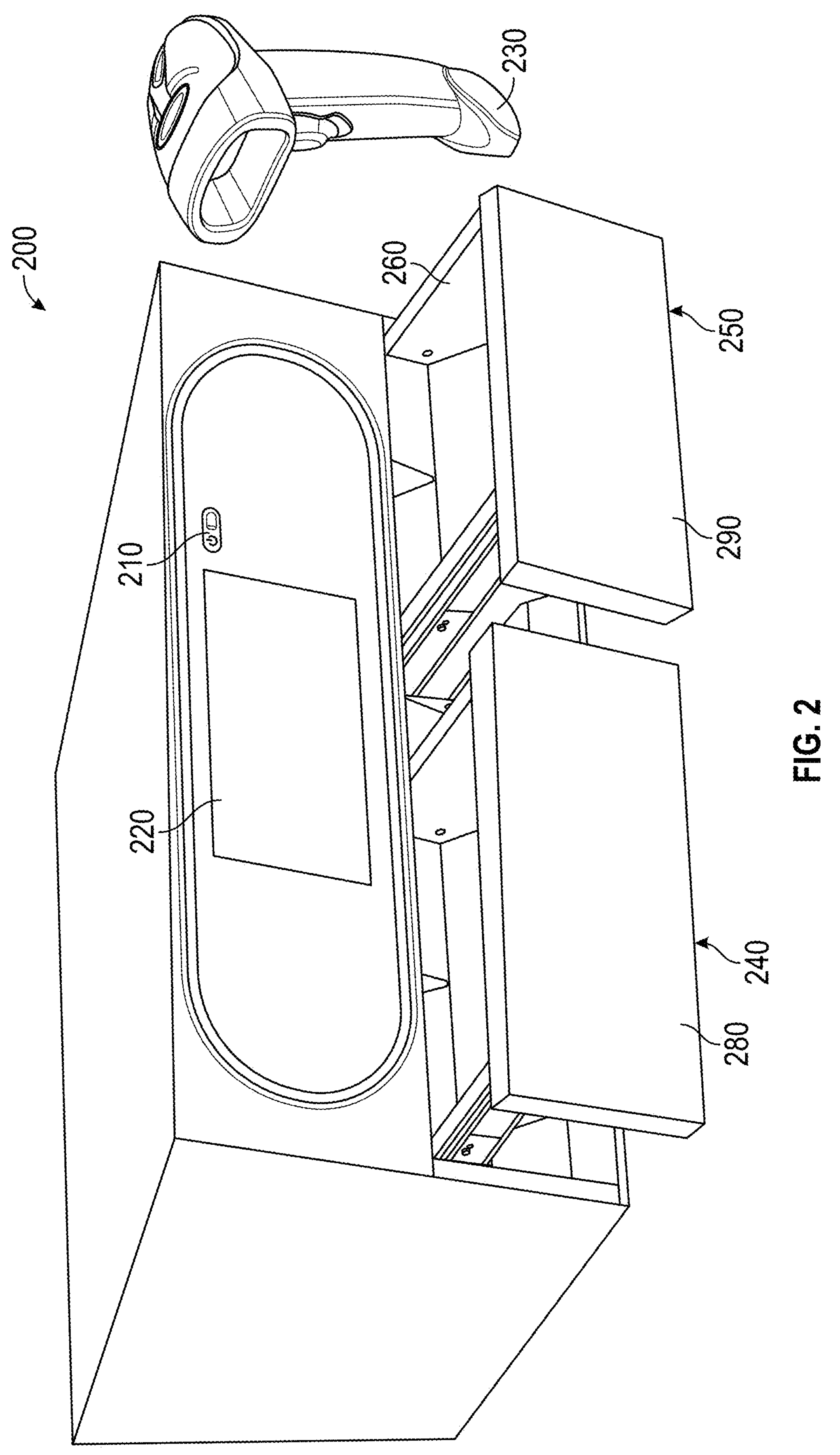
FIG. 2 illustrates another exemplary view of the device described with respect to FIG. 1 for treating biological fluids according to examples of the disclosure.

FIG. 2 illustrates an exemplary system 200 for treating biological fluids. In one more examples, the system 200 is substantially similar to system 100, as illustrated in FIG. 1. Power switch 210 can correspond to power switch 110. Display 220 can correspond to display 120. Platforms 240 and 250 can respectively correspond to platforms 140 and 150. Panels 280 and 290 can respectively correspond to panels 180 and 190.

In some examples, the system 200 includes an external scanner 230. As illustrated, the external scanner 230 is external to a housing that houses the other elements and can be operatively coupled to a processor of the system 200. In some examples, the external scanner 230 is a handheld scanner. Although the external scanner 230 is illustrated with a wireless connection in FIG. 2, the external scanner 230 can be operatively coupled using a wired connection.

As illustrated in FIG. 2, platforms 240 and 250 are in drawer configurations at an open position, in contrast with platforms 140 and 150 being at a closed position in FIG. 1. Although both platforms 240 and 250 are illustrated as in drawer configurations being open in FIG. 2, one platform in a drawer configuration can also open at a time (e.g., with the other remaining closed).

In some embodiments, a first panel 280 and a second panel 290, associated with the platforms 240 and 250, lack any handles. In some embodiments, at a closed position, a panel can be opened by applying a force opposite to the opening direction (e.g., pushing an exterior of a panel to engage a push latch that releases the panel to open). In some embodiments, at a closed position, a panel can be opened using mechanical components (e.g., motors, servos) to actuate the panel (e.g., as a hinged door, as part of the platform in a drawer configuration). In some embodiments, the system can permit a user to access the content of a platform by opening the panel (e.g., by a spring mechanism), to allow the user to further manually slide out the platform. For example, in accordance with a determination that a treatment procedure is starting or complete, the system can mechanically open one or more panels corresponding to the treatment for loading or unloading one or more biological fluid containers (e.g., treatment bags).

In some examples, the platforms include a compartment 260 substantially similar to the compartments described herein. Although FIG. 2 illustrates a platform as having one compartment visible (e.g., for a platform in a drawer configuration at an open position), each of the platforms in system 200 can include any number of compartments without departing from the scope of the application.

Figure 3:
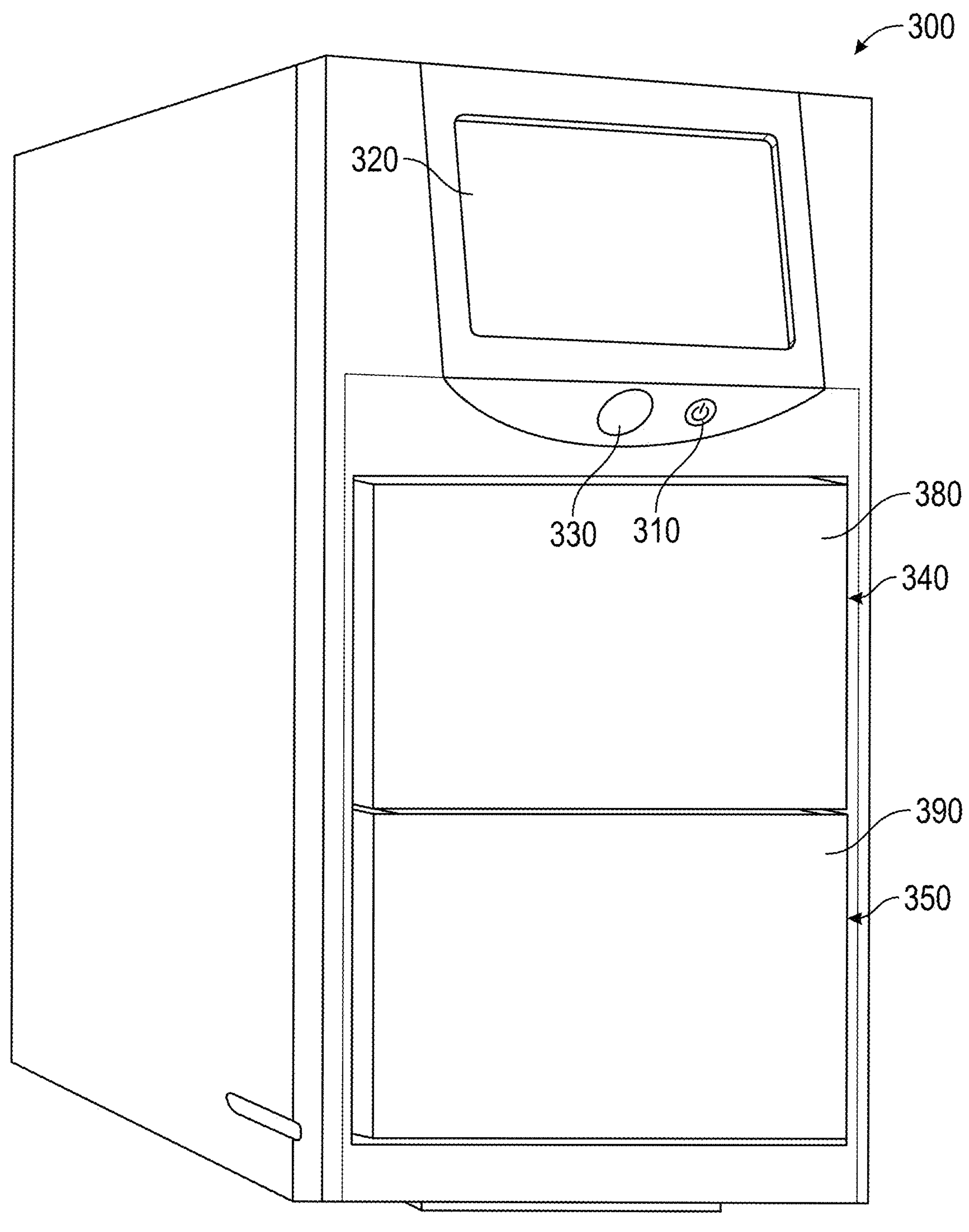
FIG. 3 illustrates another exemplary device for treating biological fluids according to examples of the disclosure.

FIG. 3 illustrates an exemplary system 300 for treating biological fluids. In some examples, the system 300 is substantially similar to system 100, with a difference that the treatment chambers and platforms are arranged vertically. Power switch 310 can correspond to power switch 110. Display 320 can correspond to display 120. Scanner 330 can correspond to scanner 130. In contrast to system 100, in which the platforms 140 and 150 are arranged horizontally, platforms 340 and 350 are arranged vertically such that the first biological fluid and the second biological fluid, when positioned on the first platform and on the second platform, respectively, are in parallel planes. Also in contrast to system 300, in which panels 180 and 190 are arranged horizontally, panels 380 and 390 are arranged vertically.

The examples of FIGS. 1-3 are meant to provide an exemplary context for the system architectures described in detail below and are not meant to be limiting to the architectures in any way. The system architectures presented herein can be utilized on a variety of biological fluid treatment devices not described above with respect to FIGS. 1-3.

Figure 4:
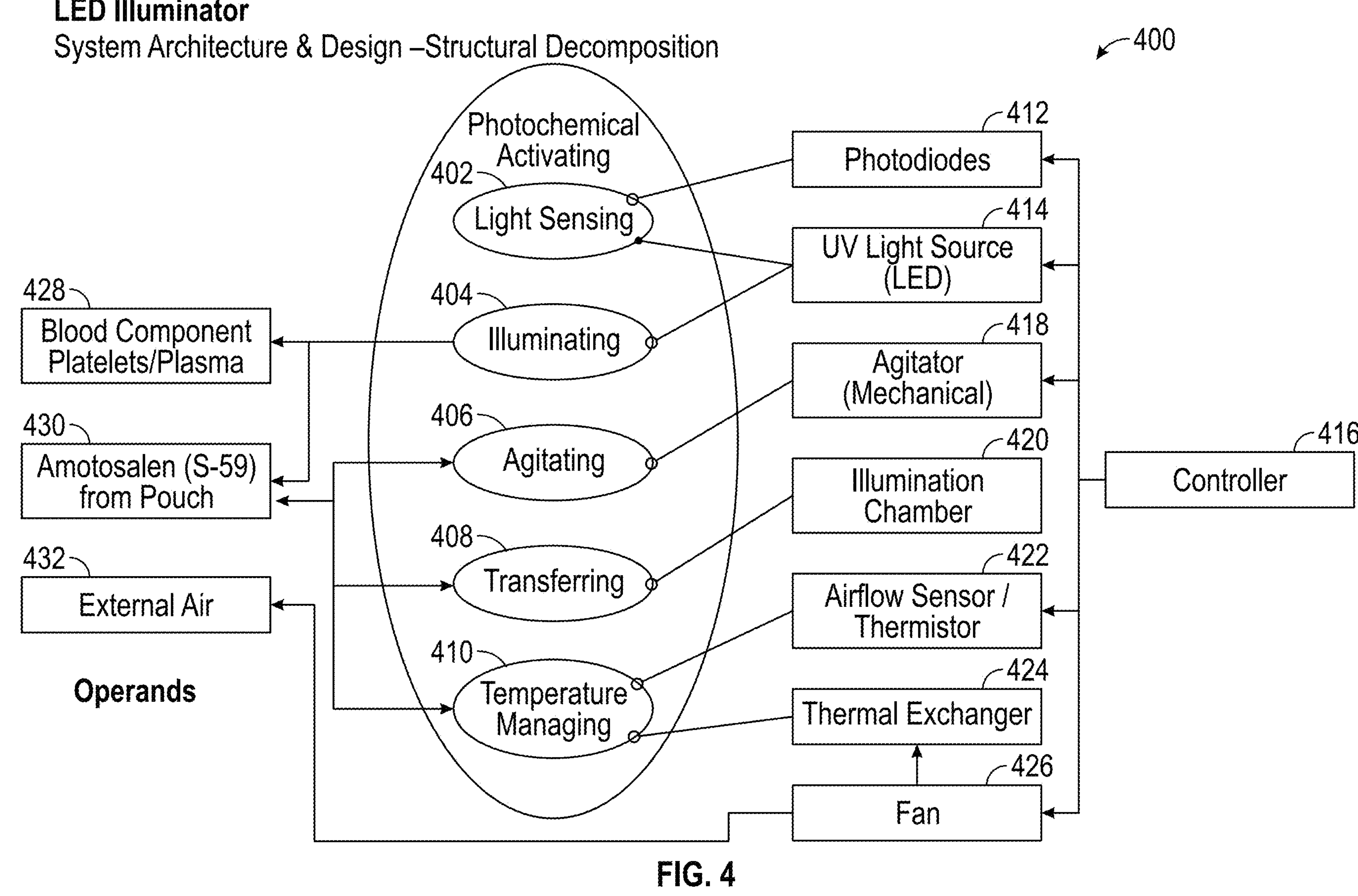
FIG. 4 illustrates an exemplary process diagram of a system for treating a biological fluid according to examples of the disclosure.

FIG. 4 illustrates an exemplary process diagram of a system for treating a biological fluid according to examples of the disclosure. The diagram 400 of FIG. 4 illustrates the various components of a system for treating a biological fluid and presents a mapping of what function each component performs with respect to the treatment process. In the example of FIG. 4, the diagram can include a plurality of processes 402, 404, 406, 408, and 410 that can collectively work with one another to treat a biological fluid. In one or more examples, the device and system for treating the biological fluid sample can include a light sensing process 402 that is configured to monitor the amount of light (e.g., UV light) being applied to a particular biological fluid. In one or more examples, the light sensing process 402 can utilize (e.g., interact with) one or more light sensors (e.g., photodiodes) 412. Light sensors 412 can be configured to convert light into electrical current. In one or more examples, the electrical current emitted from light sensor 412 can be proportional to the amount of light received by the light sensor. The light sensing process 402 can also interact with one or more light sources (e.g., UV light sources) 414. In one example, the light sensing process 402 can include using one or more light sensors 412 to sense the light being generated by the one or more light sources (e.g., UV light sources) 414. In one or more examples, the current generated by the light sensors 412 based on the light generated by the light sources (e.g., UV light sources) 414 can be transmitted to the controller 416 so as to allow the controller 416 to ensure that the biological fluid under treatment is receiving the appropriate amount of light needed to treat the biological fluid.

In one or more examples, the device and system for treating the biological fluid can include an illumination process 404 that is configured to generate the light (e.g., UV light) being applied a particular biological fluid. The illumination process 404 can include causing the one or more light sources (e.g., UV light sources) 414 to generate light (e.g., UV light) (as discussed above) so as to treat a biological fluid. As shown in diagram 400, the illumination process 404 can act upon both a biological fluid, such as for example, a blood component (e.g., platelets/plasma) 428 as well as a photoactive pathogen inactivation compound 430 such a psoralen (e.g., amotosalen) in (e.g., in admixture with) a biological fluid.

In one or more examples, the device can include an agitation process 406. The agitation process 406 can be configured to agitate the contents of the treatment container (e.g., during treatment of the biological fluid by illumination) to distribute (e.g., evenly distribute) the biological fluid and/or a pathogen inactivation compound in (e.g., in admixture with) the biological fluid. The agitation may facilitate the treatment, for example, by providing for mixing of a compound (e.g., photochemical compound, pathogen inactivation compound) in the biological fluid, or by maintaining a component (e.g., platelets, cells) of the biological fluid in suspension. In one or more examples, the agitation process 406 can include causing a mechanical agitator 418 to agitate the biological fluid (e.g., the biological fluid with photoactive pathogen inactivation compound 430). In one or more examples, the controller 416 can control the agitator 418 so as to carry out the agitation process 406. In one or more examples, one or more motors or servos (e.g., mounted to or on the platform) may be configured as the mechanical agitator 418. The one or more motors or servos may be physically coupled to the platform or a portion thereof and may move the platform or portion thereof (e.g., associated tray) forward and backward (e.g., along rails or tracks) to agitate biological fluid carried on the platform (e.g., biological fluid in a container). The one or more motors or servos may be part of any suitable agitation design (e.g., a lead screw design where one or more motors or servos move a lead screw that is attached to the platform or portion thereof, a belt-driven design where one or more motors or servos move one or more belts that rotate one or more gears (e.g., gears with teeth) that engage and move one or more tracks attached to the platform or portion thereof) and may operate based on control signals from electrical wiring that is electrically connected to control circuitry. In one or more examples, the system may be configured to control (e.g., adjustably control) one or more aspects of the agitation movement, such as offset (i.e., stroke length of the reciprocating (e.g., linear, forward-and-backward, etc.) motion during agitation), speed, acceleration, and deceleration. In some embodiments, the agitation speed may be adjustable (e.g., adjusted to have different speeds between different treatments, adjusted to have different speeds during a single treatment, adjusted based on a predetermined speed plan, adjusted dynamically in real-time based on a user's input in real-time), Such control circuitry may control the agitator (e.g., one or more motors or servos) based on a control program implemented as software and/or hardware of the control circuitry.

In one or more examples, the device can include a transferring process 408. In one or more examples, the transferring process 408 can include the operations required to transfer the biological fluid into and out of the treatment chamber. For instance, the transferring process 408 can include operating one or more doors of the illumination chamber 420 to open, close, and lock or unlock depending on which part of the treatment process the device is currently engaged in. In one or more examples, the controller 416 can control the illumination chamber 420 so as to carry out the transferring process 408.

In one or more examples, the device can include a temperature managing process 410. In one or more examples, the temperature process 410 can include the operation of one or more hardware components (e.g., airflow and/or temperature sensor 422, thermal exchanger 424, fan 426) that are collectively configured to keep the device (e.g., biological fluid being treated) within a particular temperature range. In one or more examples, the temperature managing process 410 can be configured to operate one or more fans 426 that can act on external air 432 (e.g., in conjunction with thermal exchanger 424) to cool the device in the event that the device's internal temperature exceeds a pre-determined temperature threshold (e.g., as detected by temperature sensor (e.g., thermistor) 422). In one or more examples, the controller 416 can control the one or more fans 426 so as to carry out the temperature managing process 410.

Figure 5:
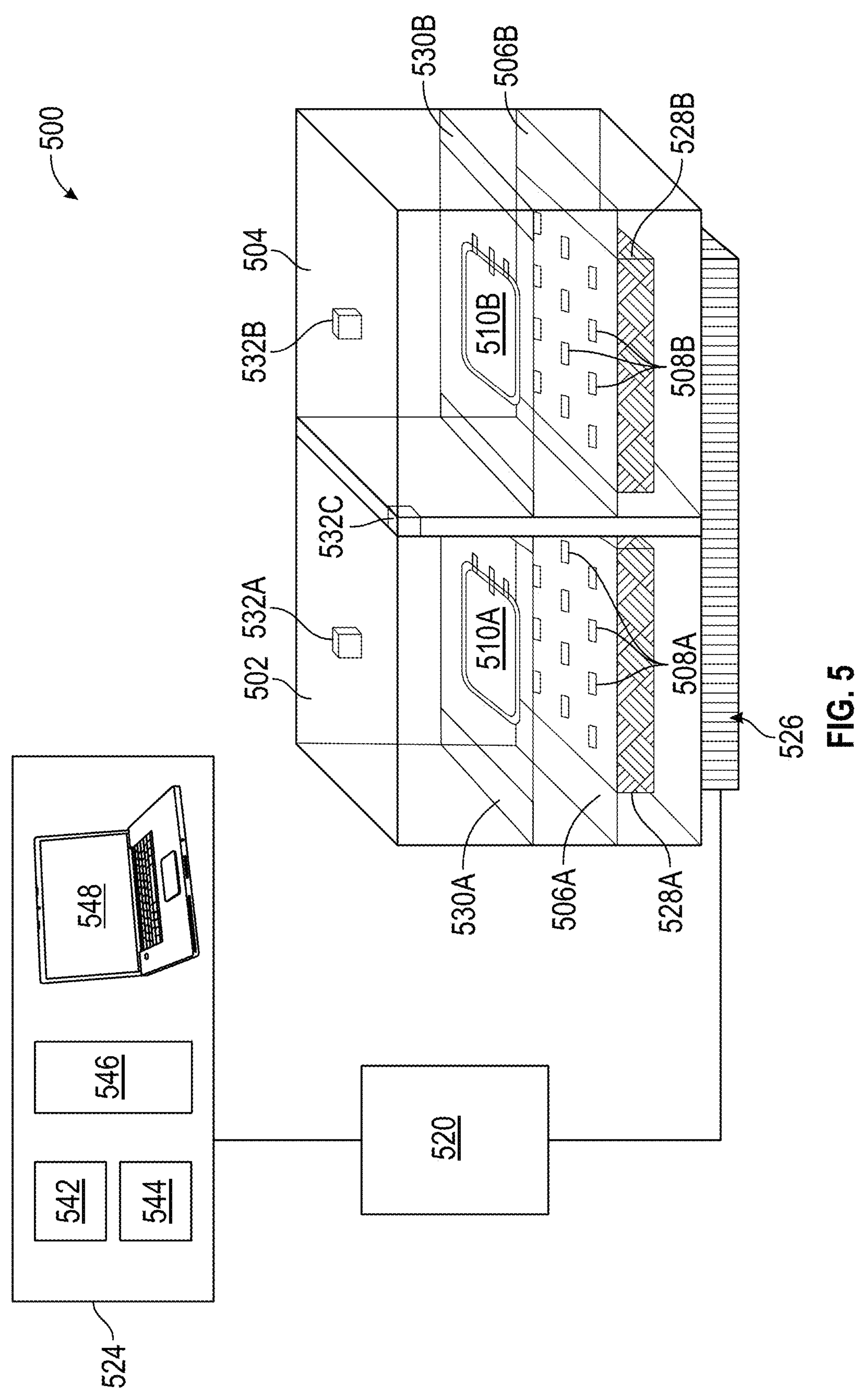
FIG. 5 is a perspective view of an exemplary system for treating a biological fluid according to examples of the disclosure.

FIG. 5 is a perspective view of an exemplary system 500 for treating a biological fluid. In some embodiments, the system 500 is substantially similar to system 100, as illustrated in FIG. 1. Exemplary system 500 for treating biological fluids includes a first treatment chamber 502 and a second treatment chamber 504 for receiving one or more biological fluids 510 and an array of light sources 506 positioned to illuminate one or more biological fluids 510. In some embodiments, the array of light sources 506 may comprise the only light sources in chamber 502 and 504 positioned to illuminate the one or more biological fluids 510. In other embodiments described below with respect to FIG. 6, multiple light source arrays may be used to illuminate one or more biological fluids positioned in various embodiments of chamber 502 and 504. As described herein, an "array of light sources" means one or more light sources disposed on any two or three dimensional surface (e.g., contiguous surface, non-contiguous surface).

One or more light source channels may be included in an array of light sources of the present disclosure. In some embodiments, one or more light source channels 508 are included in array of light sources 506. Although specific light sources are illustrated as belonging to a specific light source channel, it is understood that different combinations of the light sources can form different light source channels. Each light source channel 508 may be a set of one or more light sources having the same or substantially the same wavelength (e.g., peak wavelength, maximum peak wavelength). In an exemplary set, one light source may have a peak wavelength. In another exemplary set, two light sources may have the same peak wavelength to each other. In yet another exemplary set, each of a plurality of light sources may have different peak wavelengths from each other. In a further exemplary set, a first subset of one or more light sources may have one peak wavelength, and a second subset of one or more light sources may have a different peak wavelength. Within a light source channel having a plurality of light sources, all of the light sources may have respective peak wavelengths (e.g., maximum peak wavelengths) that all are within a wavelength range (e.g., range of 1-20 nm, 1-10 nm; e.g., 1 nm, 2 nm, 3 nm, 4 nm, 5 nm, or more, greater than and/or less than a particular wavelength) for the light source channel. For example, in some embodiments, within a light source channel having a plurality of light sources, all of the light sources may have peak wavelengths within a range set forth in the present disclosure, such as for example of about 315 nm to about 350 nm (e.g., about 315 nm to about 335 nm, about 330 nm to about 350 nm, about 340 nm to about 350 nm). In a light source channel, each light source may be any light source providing light of a desirable property (e.g., peak wavelength, maximum peak wavelength, spectral bandwidth) including, but not limited to, solid-state lighting (SSL), light-emitting diodes (LEDs), organic light-emitting diodes (OLEDs), polymer light-emitting diodes (PLEDs), and laser diodes. The light source channels of the array of light sources may be connected in a series circuit, in a parallel circuit, or in a combination of series and parallel circuits. In a light source channel having a plurality of light sources, those light sources may be controlled together or separately.

Each light source channel may be adjusted or set to emit light at different intensities (e.g., adjust the light dosage, adjust the energy dosage) at which light of the one or more peak wavelengths are applied to one or more portions of the biological fluid. For example, each light source channel may emit light at maximum intensity (e.g., 100%), or at less than maximum intensity (e.g., about 90%, about 80%, about 70%, about 60%, about 50%, about 40%, about 30%, about 20%, or less).

Each light source channel may emit various types of light. For example, each light source channel may emit ultraviolet light, ultraviolet A light, ultraviolet B light, ultraviolet C light, and/or visible light. Additionally, each light source channel may emit light of various peak wavelengths. For example, the emitted peak wavelength(s) may be in the ultraviolet A spectrum (e.g., 315-400 nm), the ultraviolet B spectrum (e.g., 280-315 nm), the ultraviolet C spectrum (e.g., 100-280 nm, 200-280 nm, 240-280 nm), or the visible light spectrum (e.g., 400-800 nm). In some embodiments, the emitted peak wavelength(s) may be between about 240 nm and about 250 nm, about 245 nm and about 255 nm, about 250 nm and about 260 nm, about 255 nm and about 265 nm, about 260 nm and about 270 nm, about 265 nm and about 275 nm, about 270 nm and about 280 nm, or about 275 nm and about 285 nm. In some embodiments, the emitted peak wavelength(s) may be between about 280 nm and about 290 nm, about 285 nm and about 295 nm, about 290 nm and about 300 nm, about 300 nm and about 310 nm, about 305 nm and about 315 nm, or about 310 nm and about 320 nm. In some embodiments, the emitted peak wavelength(s) may be between about 315 nm and about 325 nm, about 320 nm and about 330 nm, about 325 nm and about 335 nm, about 330 nm and about 340 nm, about 335 nm and about 345 nm, about 340 nm and about 350 nm, about 345 nm and about 355 nm, about 350 nm and about 360 nm, about 355 nm and about 365 nm, about 360 nm and about 370 nm, about 365 nm and about 375 nm, about 370 nm and about 380 nm, about 375 nm and about 385 nm, about 380 nm and about 390 nm, about 385 nm and about 395 nm, about 390 nm and about 400 nm. In some embodiments, the emitted peak wavelength may be about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, or about 400 nm. In some embodiments, the emitted peak wavelength may be between about 255 nm and about 275 nm (e.g., between about 260 nm and about 270 nm, about 265 nm). In some embodiments, the emitted peak wavelength may be between about 275 nm and about 295 nm (e.g., between about 280 nm and about 290 nm, about 285 nm). In some embodiments, the emitted peak wavelength may be between about 300 nm and about 320 nm (e.g., between about 305 nm and about 315 nm, about 310 nm). In some embodiments, the emitted peak wavelength may be between about 315 nm and about 335 nm (e.g., between about 320 nm and about 330 nm, about 325 nm). In some embodiments, the emitted peak wavelength may be between about 330 nm and about 350 nm (e.g., between about 335 nm and about 345 nm, between about 340 nm and about 350 nm, about 340 nm, about 345 nm). In some embodiments, the emitted peak wavelength may be between about 355 nm and about 375 nm (e.g., between about 360 nm and about 370 nm, about 365 nm). In some embodiments, the emitted peak wavelength may be between about 375 nm and about 395 nm (e.g., between about 380 nm and about 390 nm, about 385 nm). In some embodiments, the emitted peak wavelengths may be in the (1) ultraviolet A spectrum (e.g., 315-400 nm); and (2) the ultraviolet B spectrum (e.g., 280-315 nm) or the ultraviolet C spectrum (e.g., 100-280 nm, 200-280 nm, 240-280 nm). In some embodiments, the emitted peak wavelength is in the ultraviolet A spectrum, between about 315 nm and about 350 nm (e.g., between about 320 nm and about 345 nm, between about 315 nm and about 335 nm, between about 330 nm and about 350 nm, between about 340 nm and about 350 nm).

In some embodiments, all light source channels of array of light sources may emit light of about the same (e.g., within variance±1 nm, ±2 nm, ±3 nm, ±4 nm, ±5 nm, ±6 nm, ±7 nm, ±8 nm, ±9 nm, ±10 nm) peak wavelength (e.g., maximum peak wavelength). For example, in some embodiments, all light source channels of an array of light sources may emit light of a peak wavelength of 325±10 nm, 330±10 nm, 335±10 nm, 340±10 nm, 325±5 nm, 330±5 nm, 335±5 nm, 340±5 nm, 345±5 nm, 345±4 nm, 345±3 nm, or 345±2 nm. Light source channels may include a plurality of light sources with different peak wavelengths (e.g., measured peak wavelengths) within a range of variability. In some embodiments, the average peak wavelength across a plurality of light sources for a single light source channel may be the same as a particular peak wavelength for a particular light source in the single light source channel. In other embodiments, the average peak wavelength across a plurality of light sources of a single light source channel may be different (e.g., about 1 nm, 2 nm, 3 nm, 4 nm, 5 nm or more, greater than or less than) than all particular peak wavelengths of each light source in the single light source channel. In some embodiments, some light source channels may emit light of a first peak wavelength and other light source channels may emit light of a second peak wavelength. The first peak wavelength may differ from the second peak wavelength by at least (e.g., greater than) 5 nm, 10 nm, 15 nm, or 20 nm, or more. For example, in a non-limiting embodiment, a first light source channel may emit light with a peak wavelength in the ultraviolet A spectrum, such as described above (e.g., between about 315 nm and about 335 nm, between about 330 nm and about 350 nm, between about 340 nm and about 350 nm) and a second light source channel may emit light with a peak wavelength in the ultraviolet C spectrum, such as described above (e.g., between about 250 nm and about 260 nm, between about 260 nm and about 270 nm) or the ultraviolet B spectrum, such as described above (e.g., between about 305 nm and about 315 nm). In another non-limiting embodiment, a first light source channel may emit light with a peak wavelength in the ultraviolet A spectrum, such as described above (e.g., between about 330 nm and about 350 nm, between about 340 nm and about 350 nm) and a second light source channel may emit light with a peak wavelength also in the ultraviolet A spectrum, such as described above (e.g., between about 315 nm and about 335 nm, between about 355 nm and about 375 nm). In some embodiments, a first peak wavelength is the average peak wavelength of the one or more light sources of a first light source channel. In some embodiments, the array of light sources may comprise first, second, and third light source channels that each respectively emits light of a first, second, and third peak wavelength. In some embodiments, a first peak wavelength may differ from a second peak wavelength by at least (e.g., greater than) 5 nm, 10 nm, 15 nm, or 20 nm or more, and/or the second peak wavelength may differ from a third peak wavelength by at least (e.g., greater than) 5 nm, 10 nm, 15 nm, or 20 nm or more. Alternatively, each of a first, second, and third peak wavelengths may differ from each another by at least (e.g., greater than) 5 nm, 10 nm, 15 nm, or 20 nm, or more. In some embodiments, an array of light sources may comprise first, second, third, and fourth light source channels that each respectively emits light of a first, second, third, and fourth peak wavelength. In some embodiments, at least two, at least three, or at least four of the first, second, third, and fourth peak wavelengths may differ from each other by at least (e.g., greater than) 5 nm, 10 nm, 15 nm, or 20 nm or more. Alternatively, each of the first second, third, and fourth peak wavelengths may differ from each other by at least (e.g., greater than) 5 nm, 10 nm, 15 nm, or 20 nm, or more. Alternatively, the first peak wavelength may be the about same as (e.g., equal to, within variance ±1 nm, ±2 nm, ±3 nm, ±4 nm, ±5 nm) the third peak wavelength, the second peak wavelength may be the about same as (e.g., equal to) the fourth peak wavelength, and the first peak wavelength may differ from the second peak wavelength by at least (e.g., greater than) 5 nm, 10 nm, 15 nm, or 20 nm.

In some embodiments, each light source channel may emit light with a narrow spectral bandwidth. For example, the full-width half-maximum (FWHM) spectral bandwidth of light (e.g., spectral bandwidth at the maximum peak intensity) emitted by each light source channel may be less than 20 nm, less than 18 nm, less than 16 nm, less than 14 nm, less than 12 nm, less than 10 nm, less than 9 nm, less than 8 nm, less than 7 nm, less than 6 nm, or less than 5 nm. In some embodiments, the full-width half-maximum (FWHM) spectral bandwidth of light emitted by each light source channel is within 10 nm less than and/or within 10 nm greater than the peak wavelength (e.g., no more than 10 nm greater than, no more than 10 nm less than the peak wavelength). In some embodiments, the full-width half-maximum (FWHM) spectral bandwidth of light emitted by each light source channel may be greater than 1 nm, greater than 2 nm, greater than 3 nm, or greater than 4 nm, or more. In other examples, 50% of the maximum peak intensity of light emitted by each light source channel is within 10 nm, within 9 nm, within 8 nm, within 7 nm, within 6 nm, within 5 nm, within 4 nm, or within 3 nm of the peak wavelength (e.g., no more than 10 nm greater than, no more than 10 nm less than the peak wavelength; within 10 nm less than, within 10 nm more than the peak wavelength). In other examples, the light intensity at 50% of the maximum peak intensity of light emitted by each light source channel is within a spectral width less than 20 nm, less than 18 nm, less than 16 nm, less than 14 nm, less than 12 nm, less than 10 nm, less than 9 nm, less than 8 nm, less than 7 nm, less than 6 nm, or less than 5 nm (e.g., no more than 10 nm greater than, no more than 10 nm less than the peak wavelength; within 10 nm less than, within 10 nm greater than the peak wavelength). Commercially available LEDs and laser diodes are non-limiting examples of light sources that may provide such narrow spectral bandwidth illumination at the peak wavelengths discussed above.

In some embodiments, one or more of the peak wavelength of emission, the spectral bandwidth of emission, the duration of emission, and the intensity of emission of each light source channel 508 may be adjusted or set.

Adjustment of these various light source channel parameters may be performed by a control circuitry 520 operatively coupled (e.g., communicatively coupled) to treatment chambers 502 and 504, light source arrays 506, and/or to computer system 524. As used herein, “operatively coupled” refers to any wired or wireless connection between two or more components that enables the two or more components to exchange information, control instructions, and/or control signals. As will be discussed in more detail below, control circuitry 520 may receive control instructions and/or control signals from computer system 524 and send control instructions and/or control signals to various components of treatment chambers 502 and 504 to adjust or set various parameters associated with various components of chambers 502 and 504. Adjustment of various parameters of chambers 502 and 504 may be desirable to ensure that the chamber's treatment parameters are in accordance with the treatment profiles of the one or more biological fluids 510. It should be recognized that, in some examples, control circuitry 520 and/or the function of control circuitry 520 may be included within computer system 524. In some examples, control circuitry 520 may include computer system 524 and/or the function of computer system 524. In some examples, control circuitry 520 may be structurally attached to treatment chambers 502 and 504 (e.g., attached to external side, top, and/or bottom surface of treatment chambers 502 and 504). In some examples, control circuitry 520 may be integrated with treatment chambers 502 and 504 (e.g., located inside treatment chambers 502 and 504 or forming a part of the structure of treatment chambers 502 and 504).

Computer system 524 may be operatively coupled (wired or wirelessly) to control circuitry 520 and/or to any of the various sensors discussed herein. Computer system may include one or more processors 544 (544 in FIG. 5, 644 in FIG. 6), memory 542 (542 in FIG. 5, 642 in FIG. 6), an input/output (I/O) interface 546 (546 in FIG. 5, 646 in FIG. 6), and a user interface (UI) 548 (548 in FIG. 5, 648 in FIG. 6). One or more processors 544 may be one or more of any type of general purpose computer processor. Memory, or computer readable medium 542 may include one or more of readily available memory such as random access memory (RAM), read-only memory (ROM), floppy disk, hard disk, optical storage media (e.g., compact disc or digital video disc), flash drive, or any other form of digital storage, local or remote. In some examples, a non-transitory computer-readable storage medium of memory 542 may be used to store instructions for illuminating one or more biological fluids in accordance with their one or more treatment profiles, as will be discussed herein. Computer system 524 may encompass any variety of computers, such as a personal computer (PC), a desktop computer, a laptop, a computer terminal, a server computer, a tablet computer, a smartphone, a personal digital assistant (PDA), etc. In some examples, control circuitry 520 and/or the function of control circuitry 520 may be included within computer system 524.

At UI 548, a user may input one or more characteristics of a set of characteristics of one or more biological fluids (e.g., biological fluid 510). Alternatively, or additionally, the one or more characteristics of a set of characteristics of one or more biological fluids may be determined based on feedback input to computer system 524 and/or control circuitry 520 from one or more sensors for a treatment chamber (e.g., treatment chamber 502, treatment chamber 504). The characteristics of the set of characteristics of a biological fluid may include, for example, the type of the biological fluid (e.g., blood product, such as plasma, platelets, red blood cells; cells, such as eukaryotic cells; proteins, such as antibodies; vaccines), the photochemical agent in the biological fluid (e.g., type, volume, concentration), the volume of the biological fluid, the transmissivity of the biological fluid, the type and/or shape of the container carrying the biological fluid, and the temperature of the biological fluid.

At UI 548, a user may input one or more parameters that comprise the treatment profiles of one or more biological fluids (e.g., biological fluid 510). Alternatively or additionally, computer system 524 may automatically determine one or more parameters of the one or more treatment profiles of one or more biological fluids (e.g., biological fluids 510) based on the respective set of characteristics of the one or more biological fluids. In particular, memory 542 may store a computer program comprising instructions that map one or more characteristics of a biological fluid to one or more parameters of a treatment profile of the biological fluid for each biological fluid. The instructions that that map one or more characteristics of a biological fluid to one or more parameters of a treatment profile of the biological fluid for each biological fluid may be implemented as a set of user-programmable rules.

In some embodiments, array of light sources 506 may be thermally coupled to a heat exchanger 528 (e.g., heat sink, fin heat sink, heat exchanger that may be operatively coupled to and controlled by control circuitry 520). Heat exchanger 528 may draw thermal energy away from array 506 facing one or more biological fluids 510, thus minimizing the exposure of biological fluids 510 to thermal energy (e.g., thermal energy that may damage biological function). Further control of the temperature of chambers 502 and 504 and/or the temperature of the one or more biological fluids 510 may be provided by a heating/cooling unit 526 that may be operatively coupled to and controlled by control circuitry 520 and configured to adjust or set the temperature of chambers 502 and 504. Heating/cooling unit 526 may be any suitable technology known in the art, such as for example, a fan, heat pump, Peltier cooler and/or heat pipe. Heating/cooling unit 526 may be external to, inside, and/or integrated with chambers 502 and 504. For example, one or more fans may be positioned in the rear of the treatment chamber(s) to draw in air through an inlet on the exterior housing of system 500 and to expel the air through an outlet exhaust on the back of the exterior housing.

In some embodiments, heating/cooling unit 526 may be a heating unit or a cooling unit or a heating-and-cooling unit. Through the use of heating/cooling unit 526, system 500 can control the heating/cooling unit 526 to maintain the temperature of a biological fluid within a certain temperature range (e.g., a range of 1° C., a range of 2° C., a range of 3° C., etc.) during treatment of the biological fluid by illumination. For example, heat or temperature sensors can provide temperature indications or measurements to control circuitry 520 or to computer system 524 via control circuitry 520. If control circuitry 520 and/or computer system 524 processes or interpret the temperature indications or measurements as indicating the crossing of a certain threshold or condition related to a target temperature value or profile, control circuitry 520 and/or computer system 524 may instruct or command or enable or engage or actuate heating/cooling unit 526 to take action to adjust the temperature of chamber 502 or 504 and/or the temperature of the one or more biological fluids 510. For example, control circuitry 520 and/or computer system 524 may instruct or command or enable or engage or actuate one or more fans to start blowing to initiate cooling, to blow faster to provide an increased cooling rate, to blow slower to provide a decreased cooling rate, or to stop blowing to cease cooling. During treatment of the biological fluid by illumination, the one or more fans may run in operational cycles under the control of control circuitry 520 and/or computer system 524 in order to maintain the temperature of the biological fluid within a certain temperature range (e.g., a range of 1° C., a range of 2° C., a range of 3° C., etc.). Control circuitry 520 and/or computer system 524 may instruct or command or enable or engage or actuate any other suitable technology known in the art, such as for example, a fan, heat pump, Peltier cooler and/or heat pipe, or any combination of such technology to take action to adjust the temperature of chamber 502 or 504 and/or the temperature of the one or more biological fluids 510.

In some embodiments, the one or more fans may be located at the rear of the treatment chamber(s). The one or more fans may blow air in a front-to-back direction or in a back-to-front direction or both. In some embodiments, the one or more fans may draw in air to pass through the treatment chamber and expel the air through an exhaust at the rear of the system. Inlet air to the one or more fans may enter through vents located at or near the front or side(s) of the treatment chamber(s), and outlet air from the one or more fans may exit through vents located at the rear of the treatment chamber(s).

Treatment chambers 502 and 504 may further include a plurality of interior surfaces configured to absorb light (e.g., each configured to absorb light), such as for example, one or more walls made of or coated by a material (e.g., black plastic, black silicate, black paint) that substantially absorbs light of certain wavelengths. Alternatively or in addition, in some embodiments, treatment chambers 502 and 504 may further include one or more interior surfaces configured to reflect light (e.g., each configured to reflect light), such as for example, one or more walls made of or coated by a material that substantially reflects light of certain wavelengths.

Treatment chambers 502 and 504 may further comprise a platform 530 configured to hold one or more biological fluids 510 (e.g., containers of biological fluids). Platform 530 may be any support suitable for carrying biological fluids or containers of biological fluids. Platform 530 may be positioned in a "drawer configuration" so that it is slidably movable manually into and out of chambers 502 and 504. Platform 530 may be slidably movable automatically by any suitable actuator, such as an electric motor or servo. Platform 530 carrying biological fluids 510 may be positioned above the light source array 506 with light source array 506 facing platform 530. However, in other embodiments, platform 530 carrying one or more biological fluids may be positioned below light source array 506 with light source array 506 facing the platform 530.

In some embodiments, the system 500 includes one or more scanners 532 in the treatment chambers 502 and 504. The one or more scanners 532 can be located above the biological fluids 510 when the fluids are positioned for treatment (e.g., scanner 532A in the first treatment chamber, scanner 532B in the second treatment chamber). As illustrated, one or more scanners 532 (e.g., scanner 532C) can also be located between the first and second treatment chambers at the exterior (e.g., exterior housing, exterior surface) of the system 500. The one or more scanners 532 can be substantially similar to the scanners described herein. When the biological fluids are loaded into a respective treatment chamber, a respective scanner within a respective chamber can obtain identifying information about the biological fluids, as described herein. In some embodiments, the one or more scanners can be positioned at a first opening of the first treatment chamber 502, at a second opening of the second treatment chamber 504, or at openings of both chambers.

Figure 6:
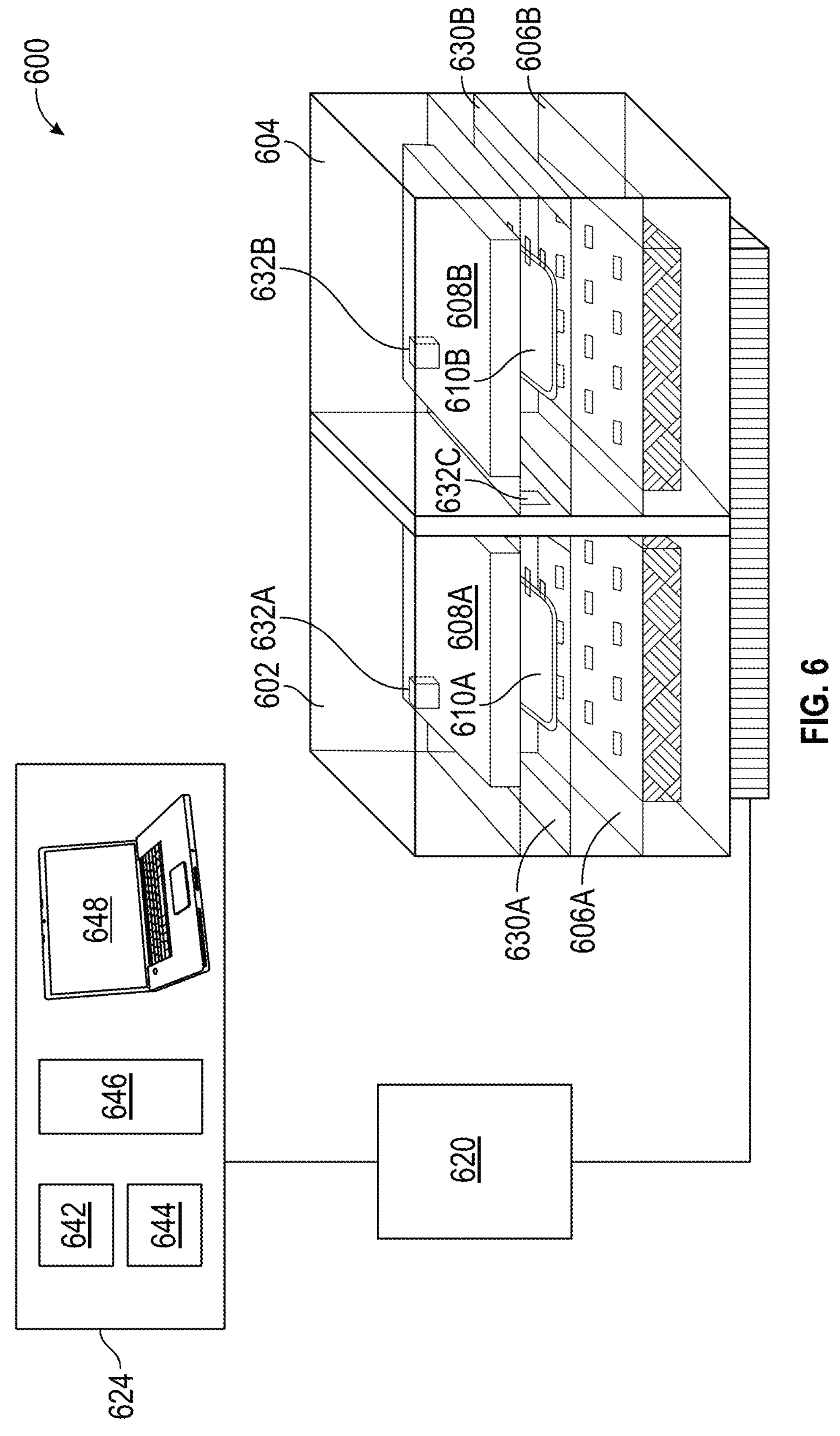
FIG. 6 is a perspective view of an exemplary system for treating a biological fluid according to examples of the disclosure.

FIG. 6 is a perspective view of an exemplary system 600 for treating a biological fluid. In some embodiments, the system 600 is substantially similar to system 500, as illustrated in FIG. 5. Exemplary system 600 for treating biological fluids includes a first treatment chamber 602 and a second treatment chamber 604 for receiving one or more biological fluids 610, a first array of light sources 606 in each chamber positioned to illuminate from below one or more biological fluids 610, a second array of light sources 608 in each chamber positioned to illuminate from above one or more biological fluids 610, a platform 630 in each chamber configured to hold one or more biological fluids 610 (e.g., containers of biological fluids), and a sensor (e.g., scanner) 632 configured to obtain identifying information of a biological fluid loaded into the treatment chamber. The first array of light sources 606 and second array of light sources 608 positioned above and below the one or more biological fluids 610 in each of treatment chambers 602 and 604 provides for illuminating the biological fluid from either one (i.e., above or below) or two (i.e., both) directions.

The system 600 can include scanner 632A positioned at the exterior (e.g., exterior housing, exterior surface) of the system 600 at a location associated with the first treatment chamber 602 (e.g., at or near an opening of first treatment chamber 602) and scanner 632B positioned at the exterior (e.g., exterior housing, exterior surface) of the system 600 at a location associated with the second treatment chamber 604 (e.g., at or near an opening of second treatment chamber 604). The system 600 can also include scanner 632C positioned inside system 600 (e.g., on an inner wall, in a ceiling, in a floor) between the first and second treatment chambers 602 and 604. In some embodiments, the scanner 632C can be configured to obtain information from containers positioned in either treatment chamber or both treatment chambers.

Figure 7:
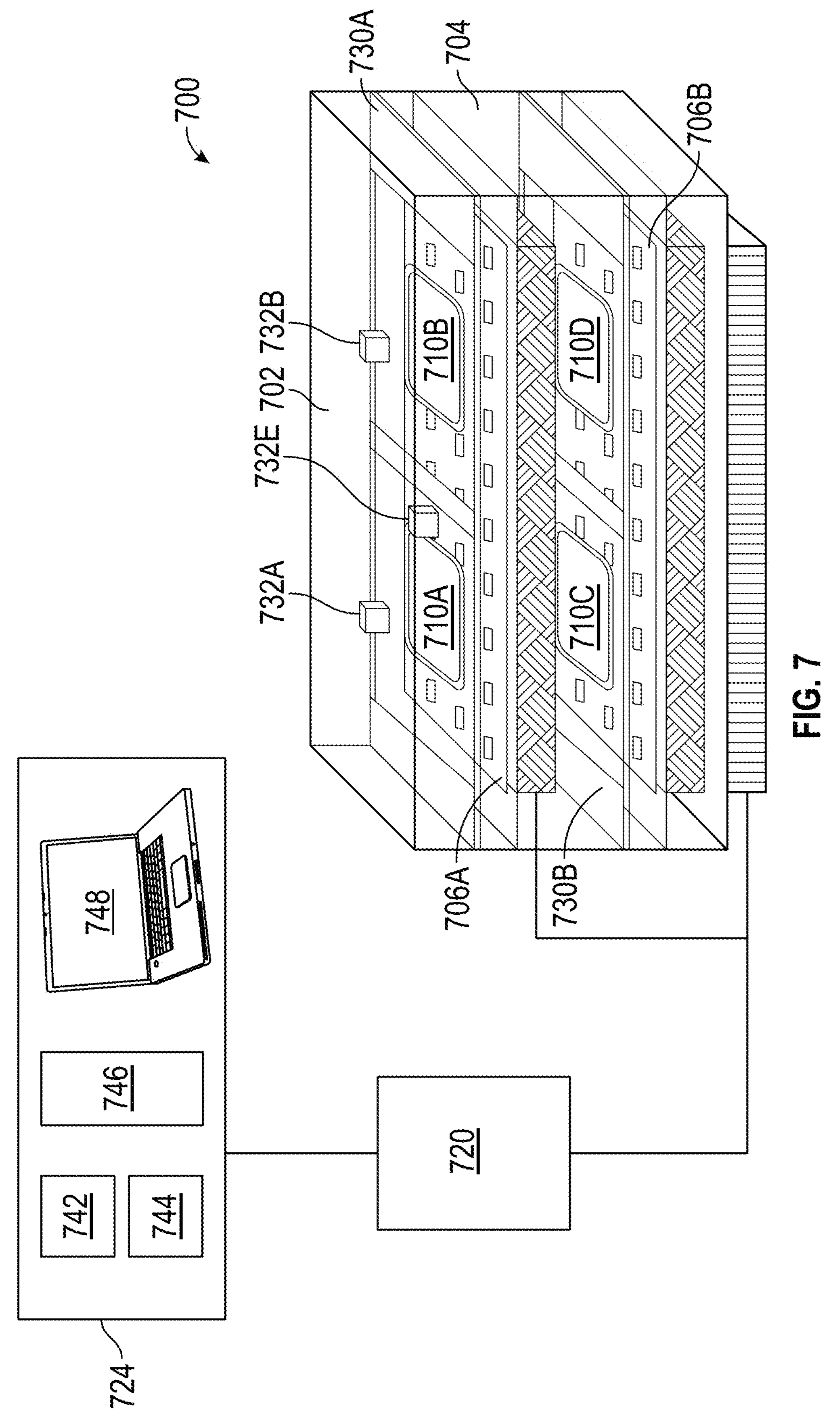
FIG. 7 illustrates a perspective view of an exemplary system for treating a biological fluid according to examples of the disclosure.

FIG. 7 is a perspective view of an exemplary system 700 for treating a biological fluid. In some embodiments, the system 700 is substantially similar to system 300, as illustrated in FIG. 3, and system 600, as illustrated in FIG. 6, differing in that the first treatment chamber 702 and the second treatment chamber 704 are positioned vertically (above and below each other) in system 700. Exemplary system 700 for treating biological fluids includes a first treatment chamber 702 and a second treatment chamber 704 for receiving one or more biological fluids 710, a first array of light sources 706 in each chamber positioned to illuminate from below one or more biological fluids 710, a platform 730 in each chamber configured to hold one or more biological fluids 710 (e.g., containers of biological fluids), and a sensor (e.g., scanner) 732 configured to obtain identifying information of a biological fluid loaded into the treatment chamber. Platform 730 carrying biological fluids 710 may be positioned above the light source array 706 with light source array 706 facing platform 730. However, in other embodiments, platform 730 carrying one or more biological fluids may be positioned below light source array 706 with light source array 706 facing the platform 730. Each of light source chambers 702 and 704 may further comprise a second array of light sources (not shown), positioned above and below the one or more biological fluids 710, such as for example similar to system 600, as illustrated in FIG. 6.

The system 700 can include scanners 732A and 732B positioned inside the first treatment chamber 702 (e.g., in the ceiling above compartments for biological fluids 710A and 710B) and two scanners similarly positioned inside the second treatment chamber 704 (e.g., in the ceiling above compartments for biological fluids 710C and 710D). The system 700 can also include scanner 732E positioned at the exterior (e.g., exterior housing, exterior surface) of the system 700 between the first and second treatment chambers 702 and 704. In some embodiments, the scanner 732E can be configured to obtain information from containers positioned in either treatment chamber or both treatment chambers (e.g., when a platform in a drawing configuration is in an open position in the field of view of scanner 732E, when RFID tags are within the detection range of scanner 732E).

Figure 8A:
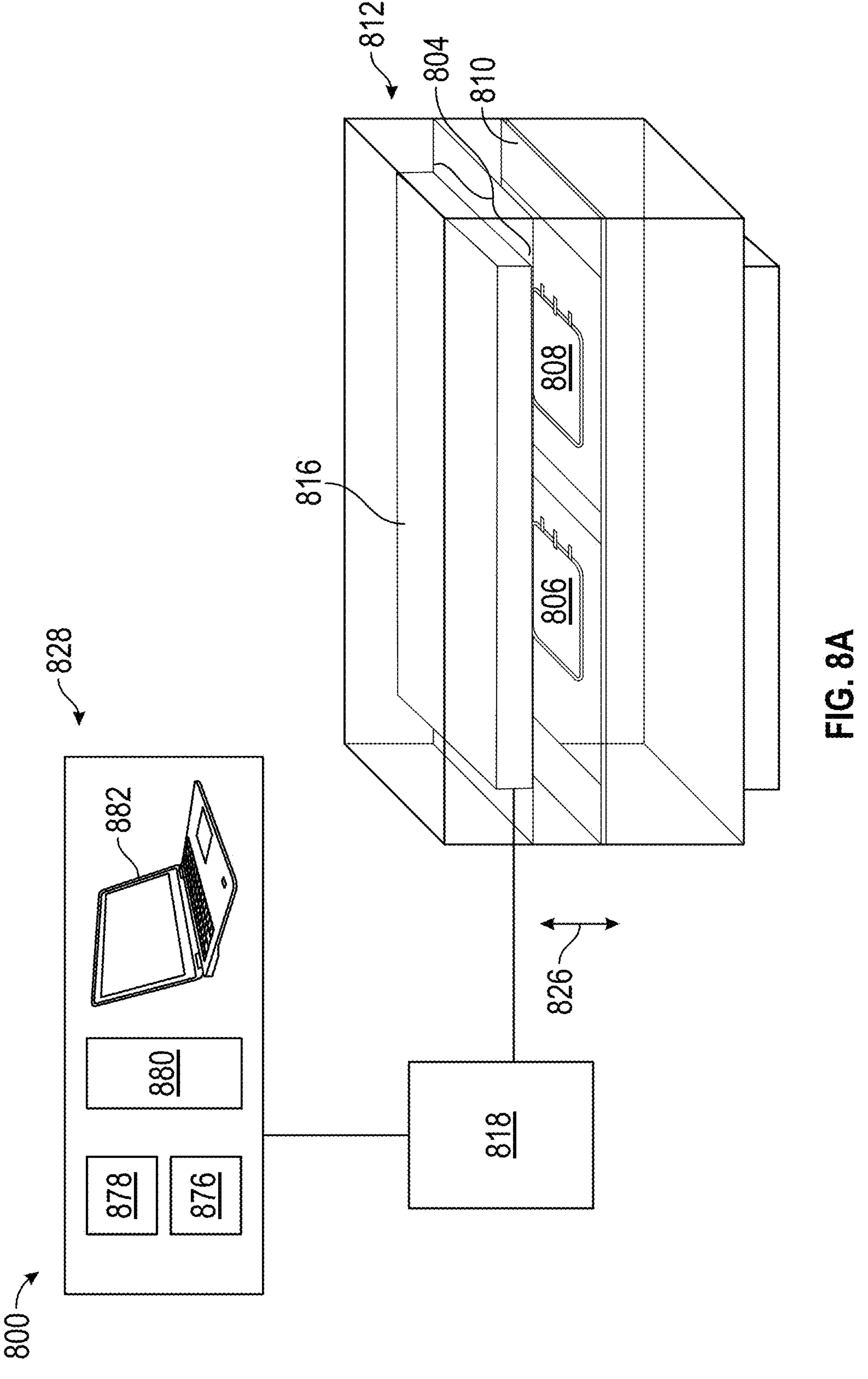
FIG. 8A-8B illustrate a perspective view of an exemplary system for treating a biological fluid according to examples of the disclosure.
Figure 8B:
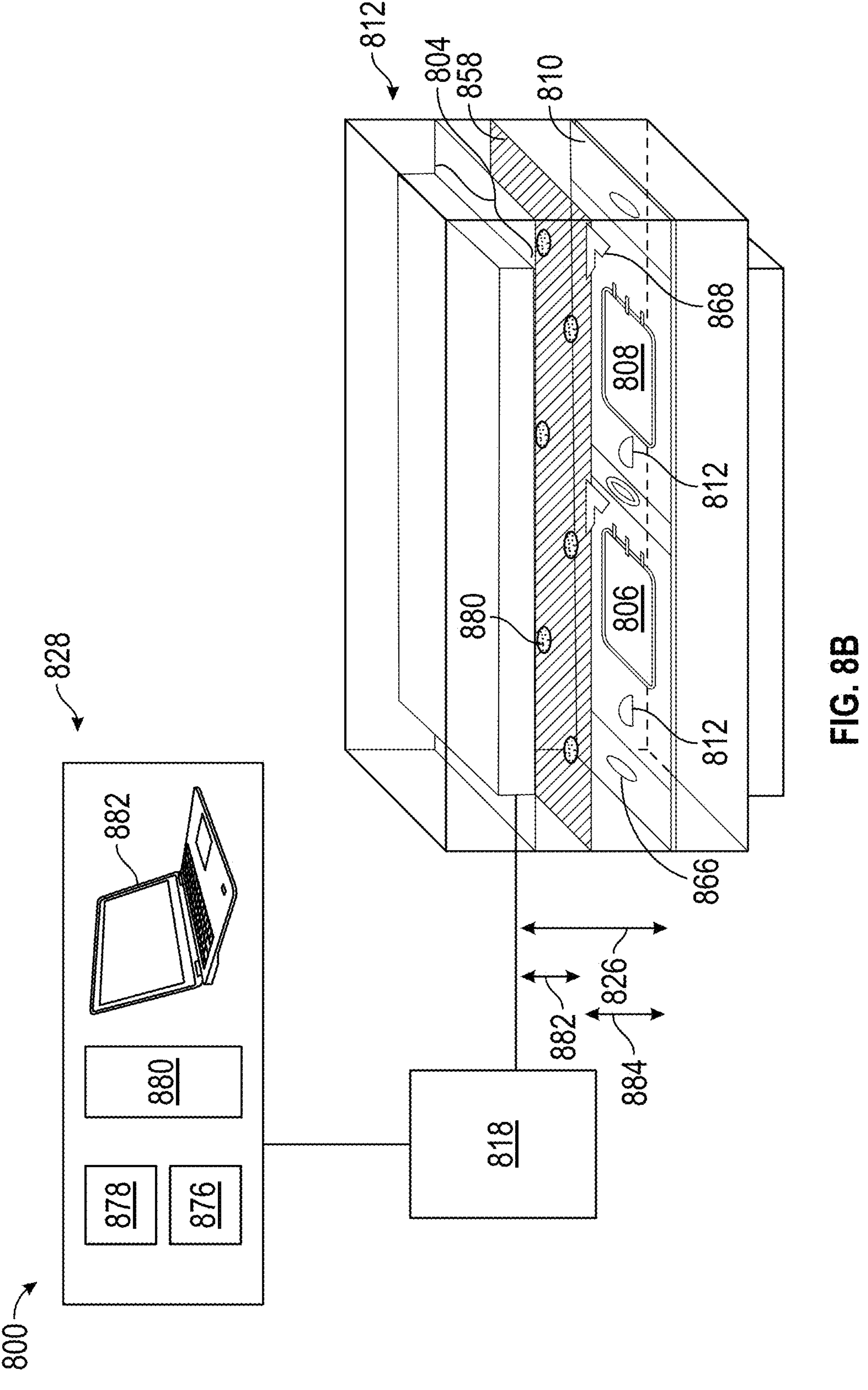

FIG. 8A shows a perspective view of an exemplary system 800 for treatment of one or more biological fluids 806 and 808 comprising a light source array 804 positioned in treatment chamber 812. Light source array 804 faces a platform 810 for biological fluids. Light source array 804 may be thermally coupled to heat exchanger 816. Treatment chamber 812 may include platform 810 positioned under light source array 804, the platform configured to hold one or more biological fluids 806 and 808. Treatment chamber 812, light source array 804, heat exchanger 816, and platform 810 may each be operatively coupled to control circuitry 818 that may adjust or set their respective parameters. FIG. 8B shows that exemplary system 800 may also include barrier (e.g., light barrier, protective barrier) 858 and various sensors 812, 866, 868, 880 in treatment chamber 812. In some embodiments, the barrier is transparent (e.g., substantially transparent, >95% transparent, >90% transparent, >80% transparent, >80% transparent) to light with a wavelength within 30 nm of the first peak wavelength (e.g., within 15 nanometers less than, within 15 nanometers greater than the first peak wavelength; no more than 15 nanometers greater than, no more than 15 nanometers less than the first peak wavelength). In some embodiments, the barrier is transparent (e.g., substantially transparent, >95% transparent, >90% transparent, >80% transparent, >80% transparent) to ultraviolet light, such as for example, light with a wavelength in the ultraviolet A spectrum. In some embodiments, the barrier is a light barrier (e.g., light filter) configured to reduce (e.g., minimize, attenuate, block) transmittance of light, such as for example light having a wavelength of less than the wavelength of light in the UVA spectrum. In some embodiments, the barrier is a light barrier configured to reduce transmittance of light having a wavelength of less than the wavelength of light in the UVB spectrum. In some embodiments, the barrier is a light barrier (e.g., light filter) configured to reduce (e.g., minimize, attenuate, block) transmittance of light having a wavelength at least 20 nm less than (e.g., at least 25 nm less than, at least 30 nm less than) the first peak wavelength and/or another peak wavelength (e.g., at least 20 nm less than the second, third, or fourth peak wavelength). In some embodiments, the barrier is a light barrier (e.g., light filter) configured to reduce transmittance of light having a wavelength at least 20 nm greater than (e.g., at least 25 nm greater than, at least 30 nm greater than) the first peak wavelength and/or another peak wavelength (e.g., at least 20 nm greater than the second, third, or fourth peak wavelength). Barrier 858 is positioned between array of light sources 804 and platform 810 (e.g., one or more biological fluids 806 and 808). Sensors 812, 866, 868 may be affixed to or positioned in platform 810. Sensors 880 may be affixed to (e.g., above or below) or positioned in barrier 858.

Light source array 804 may comprise an array of light source channels. Each light source channel of the light source array 804 may be configured to emit light of the various peak wavelengths discussed above and in the various arrangements of light sources and light source channels discussed above.

Light source array 804 and platform 810 may both be configured to translate relative to each other to increase or decrease distance 826 between them as in the translation discussed above. Platform 810 may be lowered to the bottom of treatment chamber 812, which may be raised from (e.g., by any structural base, including any components like sensors or circuitry), or flush with, an exterior bottom surface (e.g., floor, ground, desk, etc.). Lights source array 804 may be raised to the top of treatment chamber 812. In FIG. 8B, light source array 804, barrier 858, and platform 810 may all be configured to translate relative to each other to increase or decrease distances 826, 882, and 884 between any pair of: light source array 804, barrier 858, and platform 810. This translation may be effected by any number of actuators (e.g., electric motor, servo, etc.) controlled by control circuitry 818, which may separately control translation of light source array 804, barrier 858, and platform 810. In some embodiments, one or two of light source array 804, barrier 858, and platform 810 may be fixed in position in treatment chamber 812. For example, barrier 858 may be fixed in position in treatment chamber 812. As another example, barrier 858 and light source array 804 may be fixed in position relative to each other at a fixed distance 882 in treatment chamber 812 where platform 810 may be configured to translate to increase or decrease distances 826 and 884. As another example, barrier 858 and platform 810 may be fixed in position relative to each other at a fixed distance 884 in treatment chamber 812 where light source array 804 may be configured to translate to increase or decrease distances 826 and 882.

Figure 9:
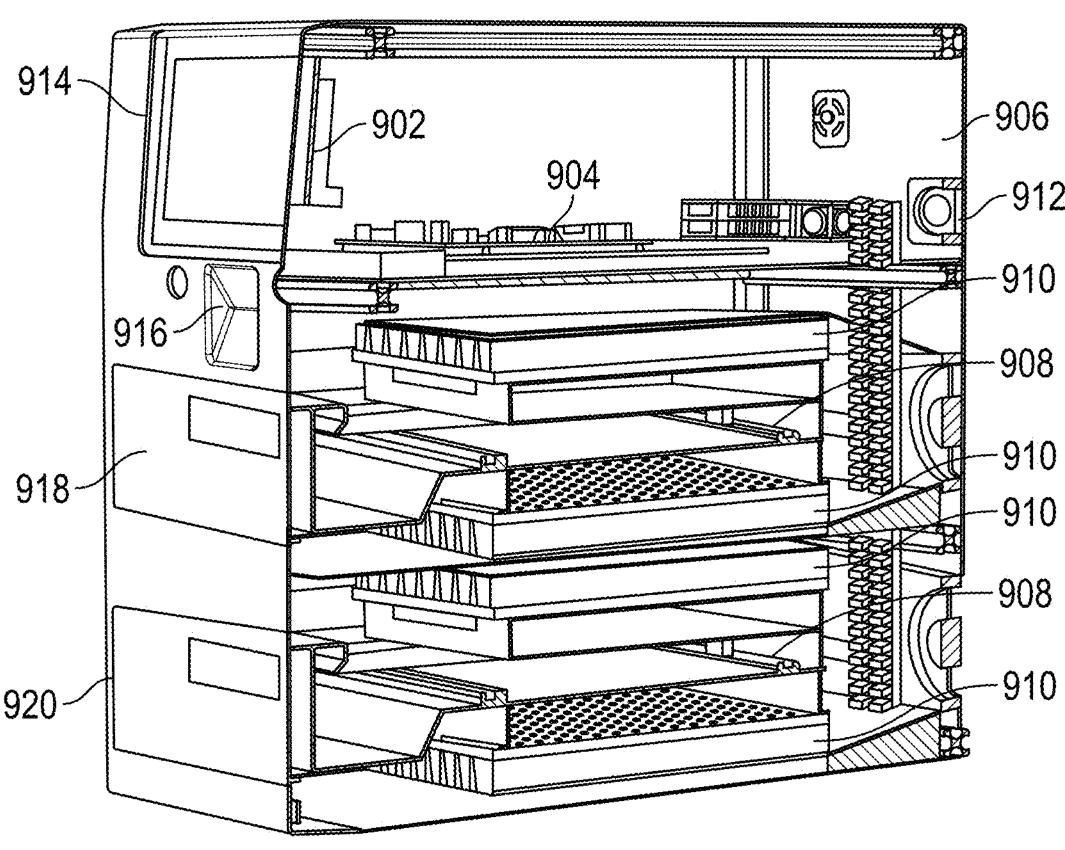
FIG. 9 illustrates an exemplary internal hardware layout for a system for treating a biological fluid according to examples of the disclosure.

As described above with respect to FIGS. 1-8 (*a* and *b*), a biological fluid treatment system (e.g., electronic treatment device) can include numerous components and systems that are required to work with another in a coordinated manner so as to safely and effectively treat biological fluids. The examples above may illustrate exemplary layouts of the components used to treat one or more biological fluids in a device in which the two treatment chambers are oriented horizontally with respect to one another, and/or in which the treatment chambers can also be oriented vertically with respect to one another. FIG. 9 illustrates another exemplary internal hardware layout for a system for treating a biological fluid according to examples of the disclosure. In the example of device 900, the treatment chambers can be oriented vertically with respect to one another such that when the device is treating two biological fluids simultaneously, the biological fluids can be disposed in the device one above the other.

The system (e.g., electronic device for treating a biological fluid) 900 can include two separate treatment chambers 918 and 920, such that in the example of system 900, the treatment chambers 918 and 920 can be oriented vertically with respect to one another. In one or more examples, each treatment chamber 918 and 920 can include one or more platforms (e.g., drawers) and associated trays 908 that are configured to carry a biological fluid (e.g., in a container) and allow for the biological fluid to be accessible by a user who can remove and/or place the biological fluid within the device. In one more examples, the system 900 can be configured with an agitator (e.g., motor, servo), such as for example an agitator configured (e.g., connected to, coupled to, integral to) a platform 908, so that any biological fluid carried on the platform (e.g., drawer, and associated tray) 908 can be agitated during treatment. In one or more examples, each platform (e.g., drawer) 908 can be configured with an agitator (e.g., motor, servo), such as for example, an integrated agitator so that any biological fluid carried on the platform (e.g., drawer, and associated tray) 908 can be agitated during treatment so as to distribute (e.g., evenly distribute) the biological fluid and/or a pathogen inactivation compound in (e.g., in admixture with) the biological fluid.

In one or more examples, each treatment chamber 918 and 920 can also include one or more modular light device (e.g. light engine) components 910. In one or more examples, the modular light device components 910 of each treatment chamber 918 and 920 can include one or more arrays of light sources (e.g., UV light sources) that are configured to deliver a desired amount of light (e.g., UV light) to a biological fluid positioned in each of the treatment chambers (e.g., on a platform in the treatment chamber).

In one or more examples, and as discussed in further detail below, the system (e.g., electronic device) 900 can include a control system board (CSB) 904 that is configured to coordinate the operation of one or more components of the device, such as for example, safety-critical components of the device. In one or more examples, a safety-critical component can refer to one or more components of the electronic device that interact with the biological fluid being treated, and whose operation if done incorrectly can jeopardize the safety and efficacy (e.g., meeting required specifications) of the treatment process on the biological fluid. In one or more examples, the CSB 904 can be configured to communicate with and issue commands to each of the safety-critical components (described in further detail below) using a domain-specific customized communications protocol configured to protect the safety-critical components from being accessed by a unauthorized (e.g., malicious) user, and configured to allow the device to be both modular and scalable with minimal disruption to the operation and/or maintaining regulatory compliance of the device. In one or more examples, the CSB 904 can be configured to communicate with and control the operation of the platform (e.g., drawer, and associated tray) 908 and the light device components 910, inter alia, as these components directly interact with the biological sample and incorrect operation of these components could jeopardize the safety and/or efficacy of the treatment process. In one or more examples, the CSB 904 can also be configured to operate one or more fans 912 so as to move air through the electronic device (e.g., pull air from the front of the electronic device to the rear of the device) in order to cool the device and biological fluid being treated, and prevent any overheating. In addition to controlling each of the components, the system CSB 904 can be configured to assess results from each of the components, which in one or more examples can be continuously communicated to it. The CSB 904 can be configured to use the results to determine subsequent operating steps of the device, for instance to stop agitation, initiate and/or terminate illumination, or complete the treatment process.

In addition to the treatment chamber specific components described above, in one or more examples, the electronic device 900 can include one or more components that are not dedicated to a particular treatment chamber but instead are configured to operate the entire device and thus are common for both treatment chambers. In one or more examples, the electronic device 900 can include a User Interface Controller (UIC) 902 that can be configured to manage the operation of one or more components of the device 900. In one or more examples, UIC 902 can be configured to coordinate the operations of one or more non-safety critical hardware and software components (described in further detail below). For instance, and in one or more examples, UIC 902 can be configured to operate one or more graphical user interfaces that are displayed on display 914. The one or more graphical user interfaces can be configured to guide a user through the treatment process and receive input from a user to determine information about the biological fluid to be treated and well as any other information the device may need to perform the treatment process. In one or more examples, the display 914 can be implemented as a "touch display" in which the user can touch the surface of the display to enter any inputs or otherwise interact with the device during the treatment process.

In one or more examples, the UIC 902 can also communicate with and control a scanner (e.g., barcode scanner) 916. The scanner 916 can be configured to scan one or more sources of identifying information (e.g., barcodes) found on a container that holds the biological fluid and includes information pertinent to the identifying the biological fluid as well as other information needed to ensure proper treatment of the material.

As illustrated in FIG. 8B, the system can include multiple components and sensors that work in conjunction with one another to deliver light to a sample for treatment. For instance, and as described above with respect to FIG. 8B, the treatment chamber 812 can include a light source array 804, and one or more sensors 812, 866, 868, and 880 that work in conjunction with one another to illuminate the sample being treated. In one or more examples of the disclosure, sensors 812, 866, 868, and 880 can include a mixture of light sensors (e.g., photodiodes) and temperature sensors (e.g., thermistors) that are configured (e.g., jointly configured) to ensure that the biological fluid being treated is being illuminated with a precise amount (e.g., dose) of light, uniformly, and the light sources and/or illumination process are operating a temperature that does not cause the overall device to overheat.

However, if one of the components that work together to deliver UV light to the biological fluid should malfunction, be upgraded, or come to the end of its life, simply replacing that component can be an arduous and complicated process. For example, if one or more of the LEDs in the light source array 804 malfunction such that the light source array overall is unable to deliver the proper amount of UV light to a biological fluid, simply replacing the light source array may not be adequate to return the electronic device to normal operating condition. For instance, since the sensors may have been placed and configured with respect to the light source array that was originally installed in the device, replacing that light source array may also require that one or more of the sensors be reconfigured. For instance, in the example of the photodiodes, the position of the one or more photodiodes may need to be reconfigured should the light source array be changed because the LEDs in the light source array may not be in the same position as they were in previous light array. If the photodiodes are not repositioned, then they may not accurately capture the light produced by the light source array to determine if adequate light is being transmitted to the sample being treated. Alternatively, or in addition, if one or more of the light source arrays 804 is to be substituted with a different light source array, simply replacing the light source array may not be adequate to return the electronic device to normal operating condition. For example, upgrading or changing light sources (e.g., LEDs) in a light source array, such as for example, to incorporate different peak wavelength(s), increase efficiency of the light sources, change beam width, etc., may require changes to light sensor photodiodes.

In addition to reconfiguring any or all of the components associated with light delivery, replacing the component(s) may also require a labor and time intensive effort to electrically reconnect all of the various components (i.e., light source array and sensors) and ensure (e.g., validate) that the components work together with one another to deliver the appropriate amount of UV light to the biological fluid being treated. For instance, if the light source array 804 is replaced, then in one or more examples, the light source array may need to be reconnected to the various sensors 812, 866, 868, and 880 to ensure that the components can communicate with one another to operate the overall device in a safe and efficient manner.

Thus, in one or more examples, it may be advantageous to house multiple or all of the components associated with light delivery (i.e. the light source array, the sensors, and other control electronics) in a single housing such that if one of the components fails or is upgraded, the entire light delivery system can be replaced together therefore obviating the need to reconfigure each of the other components and reconnect them to the replaced component. Returning to the example of FIG. 9, in one or more examples, each light device 910, can include substantially all of the components and sensors associated with delivering UV light to a biological fluid under treatment. As will be further described in detail below, by providing a light device that is stand-alone and includes the sensors and components require for light delivery, the light device can be made to be "modular" so that the entire light device can be replaced should one or multiple components of the light device malfunction, be upgraded, or come to the end of their life.

As shown in FIG. 9, the electronic device for treating a biological fluid can include four light device components 910 and two platforms (e.g., and associated trays) 908. The number of light device components 910 and platforms 908 shown in FIG. 9 are meant only as examples and should not be seen as limiting. An electronic device for treating biological fluids could include more or less of each component. In one or more examples of the disclosure, each platform 908 (which during use will hold a biological fluid (e.g., container with biological fluid) for treatment) can have two light device components 910 directed towards it, one disposed above the platform and one disposed below the platform, with the light sources of each light device components pointed (e.g., oriented) towards the platform and configured to deliver a specific amount of UV light to the biological fluid on the platform (e.g., and associated tray). Thus, in one or more examples, the light device components 910 disposed above a platform 908 can be oriented such that the light generated by the components can be directed downward toward the platform 908, while the light device components 910 disposed below a platform 908 can be directed upward toward the platform 908. In this way, the platform (e.g., and associated tray) 908, which holds the biological fluid, can be treated by UV light originating from above and below. As discussed above, should one of the components in any of the light device components 910 malfunction or otherwise need to be replaced (e.g., upgraded), it would be advantageous to be able to simply replace a single unit that houses all of the light delivery components, rather than attempting to simply replace the malfunctioning or upgraded component. Thus, in one or more examples of the disclosure, the light device components can be housed in a single device that is configured to be modular and easily replaceable should one of the components malfunction or otherwise need replacement.

In one or more examples, the light device components 910 can be substantially identical in that they all contain identical components with the same configuration. However, in one or more examples, each set of light device components 910 (which can be housed in a single light device) can be configured differently from one another. For example, one of the light device components 910 associated with a given treatment chamber can be configured to emit a particular peak wavelength of light (e.g., UV-A light), while another of the light device components 910 can be configured to emit a different peak wavelength of light (e.g., UV-B or UV-C light). In such a scenario, the biological fluid sitting on platform 908 during the treatment process can thus be treated simultaneously by two light sources emitting different wavelengths (e.g., peak wavelengths) of light. Such a need might arise, if it is found, that the process of pathogen inactivation could benefit from being treated by both UV-A and UV-B or UV-C light.

Figure 10:
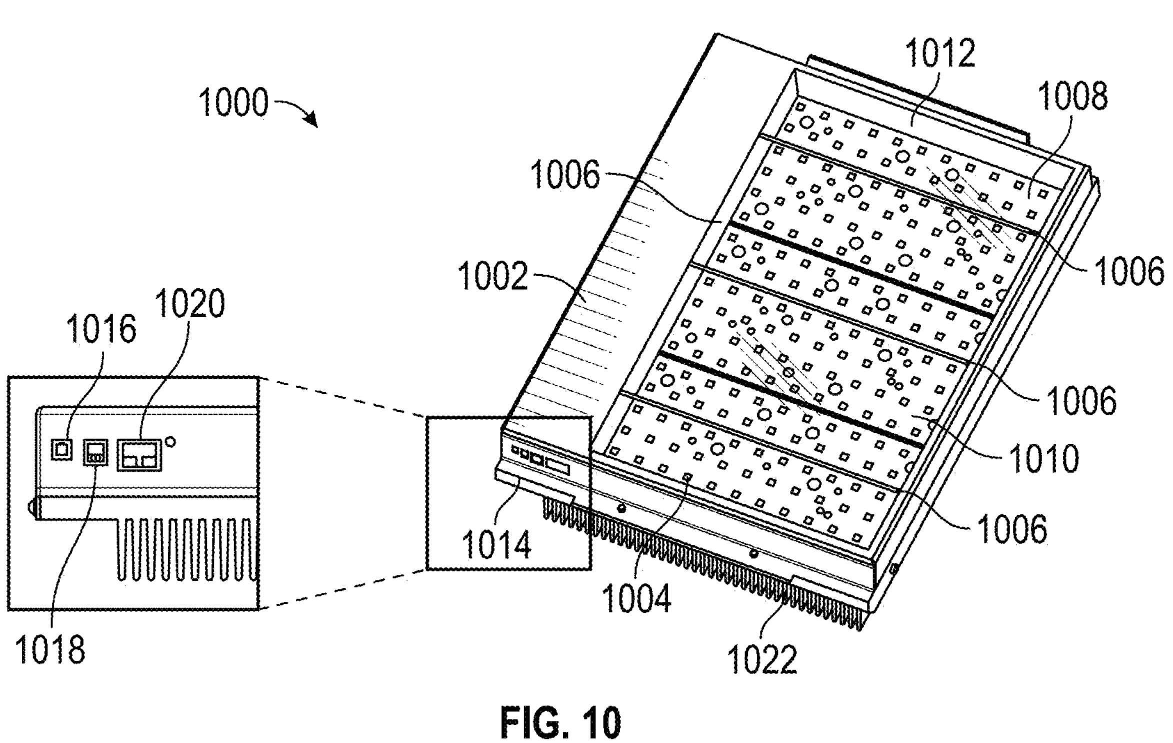
FIG. 10 illustrates an exemplary modular light device for use in a system for treating a biological fluid system according to examples of the disclosure.

FIG. 10 illustrates an exemplary modular light device for use in a system (e.g., electronic device) for treating a biological fluid according to examples of the disclosure. As illustrated in the example of FIG. 10, and as will be further described in detail below, the modular light device 1000 can be configured to house multiple, such as for example substantially all of the components (e.g., light sources) and sensors needed to generate and transmit light (e.g., a desired dose of UV light) to a biological fluid under treatment (e.g., self-contained light device). In one or more examples of the disclosure, the modular light device 1000 can include a housing 1002 that is configured to house the components within the light device. In one or more examples, the housing 1002 can include a window portion (e.g., transparent material portion, transmissive material portion) 1004 that is configured to allow the light sources housed within the modular light device 1000 to transmit light to a biological fluid under treatment (i.e., configured to pass light from the light sources). In one or more examples, the window portion may be an opening in the housing. In one or more examples, the window portion may protect the light source array(s) and light source(s) from possible contamination (e.g., from biological fluid, from dust). In one or more examples, the window portion may comprise a window material covering/enclosing an opening to the light source array chamber. In one or more examples, the window portion (e.g., transparent material portion, transmissive material portion) 1004 can be configured to be UV transparent (e.g., made of a material selected to transmit or pass light of a selected wavelength). In one or more examples, the window portion (e.g., transparent material portion, transmissive material portion) 1004 can be made from a material (e.g., transparent material, transmissive material) such as glass, quartz based, plastic or acrylic or other polymeric (e.g., thermoplastic) material, that is configured to transmit a substantial amount of the light energy generated by the device. In one or more examples, the window portion 1004 can be configured to be UV transmissive (i.e., >50% transparent, >60% transparent, >70% transparent, >80% transparent, >90% transparent, >95% transparent). In one or more examples, the transmissiveness of the window portion 1004 can be correlated to the amount of light delivered by the modular light device 1000. Thus, in one or more examples, a modular light device 1000 that has a window 1004 that is only 80% transmissive can be configured to generate light at a higher intensity than a window 1004 that is 90% transmissive, so as to deliver a precise amount of light to a biological fluid under treatment. In one or more embodiments, the window portion may be configured with a window portion (e.g., window material) that is a flat (e.g., planar). In one or more embodiments, the window portion may be configured with a material portion that is a curved (e.g., convex, concave).

In one or more examples of the disclosure, the window portion 1004 can include one or more light sensors (e.g., photodiodes) disposed on or across the window 1004 (e.g., facing the light sources, light source arrays). In one or more examples, the window portion 1004 can include one or more circuits (e.g., cables, PCB traces, flexible circuit strips) 1006 disposed on or across (e.g., facing the light sources, light source array(s)) the window 1004 and configured to support one or more light sensors (e.g., photodiodes, facing the light sources, light source array(s)). As will be discussed in further detail below, the photodiodes arranged on the circuits (e.g., flex circuits) 1006 can be configured to measure the amount of light being transmitted by light sources, such as for example, a light source array (e.g., an LED array) housed within the modular light device 1000. In one or more examples, the light sensors can be implemented using any number of light sensing technologies including for instance UV phototubes and/or photodiodes. In one or more examples, each circuit is a flex circuit and as each flex circuit may create a shadow in the light path, the flex circuits can be, for example, about 5 millimeters or less, about 4 millimeters or less, or about 3 millimeters or less wide so as to minimize the interference they may create with respect to the light being delivered to a biological fluid. While the flex circuits 1006 may create shadowing in the light path of the modular light device, the shadowing (representing a noise source) may, in one or more examples, be modulated out (i.e., averaged out) by the agitation of the biological fluid in the treatment chamber and/or the number of and/or positioning of light sources in a light source array. Thus, in some examples, the agitation process used to treat the biological fluid may also act to minimize the performance degradation associated with the shadowing. In one or more examples, each of three flex circuits can be configured to hold three light sensors (e.g., photodiodes) such that the three flex circuits 1006 can collectively hold nine light sensors (e.g., photodiodes). While adding more light sensors (e.g., photodiodes) and/or flex circuits can lead to more accurate measurements of the light being generated by the modular light device 1000, it can lead to more occlusions or impediments of the light being transmitted to a biological fluid. Likewise, including less (i.e., fewer) light sensors (e.g., photodiodes) and/or flex circuits may reduce the shadows created by the flex circuits 1006, but may lead to a loss in the accuracy of light measurement. Thus, the amount of photodiodes and flex circuits can represent a design trade-off between measurement accuracy and shadowing of the light generated by the modular light device 1000.

In one or more examples of the disclosure, the modular light device 1000 can include a light source array chamber/cavity (e.g., LED array chamber) 1008 disposed underneath (e.g., to the interior of) the window 1004 and configured to hold the multiple light sources (e.g., LEDs), sensors, and other components needed to generate the light for treatment (discussed in further detail below). In one or more examples, the light source array chamber (e.g., LED array chamber) 1008 can include a one or more light source arrays (e.g., LED arrays) 1010. The light source array (e.g., LED array) 1010 (discussed in further detail below with respect to FIG. 11) can include one or more light sources (e.g., LEDs) and light sensors (e.g., photodiodes), and optionally, one or more temperature sensors. In addition to the one or more light source arrays (e.g., LED array) 1010, the light source array chamber (e.g., LED array chamber) 1008 can include one or more reflectors 1012 disposed on the sides of the chamber 1008 and configured to surround the perimeter of the light source array(s) (e.g., LED array) 1010. The reflectors 1012 can be configured to redirect light generated by light sources (e.g., LEDs) on the perimeter of light source array (LED array) 1010 back towards the window (e.g., central portion of the window) 1004 so as to minimize the loss of light energy at the edges of the light source array chamber (e.g., LED array chamber) 1008. In this way, while the light sources (e.g., LEDs) on the perimeter of the light source array(s) (e.g., LED array) may direct light (e.g., a portion of the light) towards the wall of the light source array chamber (e.g., LED array chamber) 1008 rather than towards the biological fluid being treated, the reflectors 1012 can redirect that light back towards and through the window 1004 so that it is not wasted and can be used to treat a biological fluid, thereby improving the overall efficiency of the light source array(s) (e.g., LED array) 1010. The reflectors 1012 thus help to conserve potentially wasted light energy, while also ensuring that the modular light device 1000 generates a more uniform amount of light (e.g., across the entire device, across the surface of the biological fluid to be treated, within an illumination volume).

In one or more examples of the disclosure, the modular light device 1000 can include one or more interfaces (e.g., ports) for electrically connecting the modular light device to various components of the electronic treatment device. In one or more examples, the modular light device 1000 can include an interface panel 1014 located on a side of the housing 1002. The interface panel 1014 can include one or more interfaces for electrically connecting the modular light device 1010 to various components of the electronic treatment device. In one or more examples, the interface panel 1014 can include an interlock connector 1016. When connected to the electronic device, the interlock connector 1016 can be configured to allow the electronic device to quickly and efficiently shut down the modular light device should the device encounter a condition, fault, or state, in which continued operation of the modular light device 1010 may be undesirable. As an example, if the electronic device detects that there is a problem with the biological fluid being treated (i.e., it has not been loaded properly onto the tray or in the treatment chamber) or the agitator has malfunctioned, the device can shut down the modular light device 1000 quickly through the use of the interlock connector 1016.

In one or more examples, the interface panel 1014 can include a power port 1018 that is configured to connect the modular light device 1000 to the power source of the electronic treatment device. In this way, the modular light device 1000 may not be required to carry its own power source, but instead can be connected to the power source of the electronic device once the modular light device 1000 has been installed in the electronic device. In one or more examples of the disclosure, the power port 1018 can be configured to connect the external power source to the internal components of the electronic device that require power such as the light sources (e.g., LEDs), sensors, etc. In one or more examples, the power port 1018 can be configured to transmit power from the external power source to one or more controllers/drivers (discussed in further detail below) that can be configured to distribute the electrical power to the various components within the modular light device 1000. In one or more examples, the power port 1018 can be rated to 48V and the modular light device itself can be configured to consume approximately 225 W of power.

In one or more examples, the interface panel 1014 can include a communication port, such as for example, an Ethernet port 1020. The ethernet port 1020 can be configured, when connected to the device, to provide networking capabilities to the modular light device 1000. As described in further detail below, the ethernet port can allow for the modular light device to communicate with other safety-critical components within the electronic device using a specialized domain-specific communications protocol configured to isolate the safety-critical components of the electronic device from being interfered with by external sources.

In one or more examples of the disclosure, the modular light device 1000 can include a heat exchanger 1022 located at the bottom (e.g., base) of housing 1002. As discussed in further detail below, the heat exchanger can be shaped and configured to reduce or remove heat generated by the various components of the modular light device away from the modular light device (e.g., and away from the biological fluid) so as to maintain the modular light device, treatment chamber and/or biological fluid at a desired operating temperature (e.g., within a desired operating temperature range).

Figure 11:
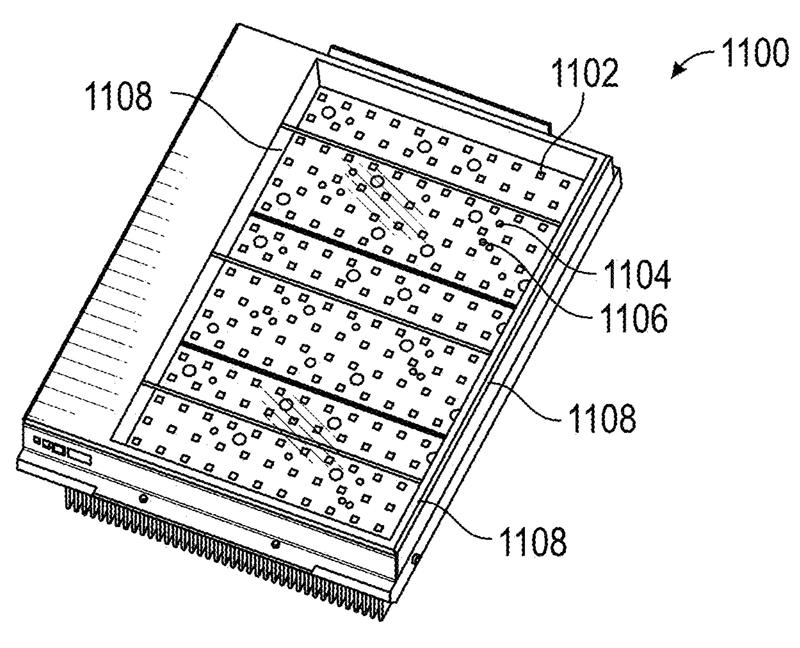
FIG. 11 illustrates an exemplary modular light device for use in a system for treating a biological fluid system according to examples of the disclosure.

FIG. 11 illustrates a top view of an exemplary modular light device 1100 for use in a system for treating a biological fluid according to examples of the disclosure. FIG. 11 further illustrates the components found within the light source array chamber (e.g., LED array chamber) 1008 of FIG. 10. As illustrated in FIG. 11, the modular light device 1100 can include a plurality of light sources such as UV LEDs 1102 configured to generate UV light during operation of the modular light device 1100. In one or more examples, the plurality of LED light sources 1102 of the light source array(s) can be distributed on one or more panels 1108. For instance, in the example of FIG. 11, the light source array chamber (e.g., LED array chamber) 1008 can include three panels 1108 disposed at the interior base of the chamber, and the LED light sources 1102 can be distributed across the three panels such that a portion of the LED light sources are disposed upon each panel 1108. The number of light sources (e.g., LEDs) 1102 in a light source array chamber 1008 can be dependent on a number of factors. In one or more examples, each modular light device 1100 of the electronic treatment device can be configured to generate light across the surface of a treatment bag or other treatment container (e.g., containing a biological fluid), at particular depths of biological fluid in a treatment bag, and/or around a pre-defined illumination volume that surrounds the treatment bag (e.g., fluid contained within a pre-defined illumination volume). In one or more examples, the pre-defined illumination volume can represent a three dimensional space around the platform (e.g., and associated tray) towards which a substantially uniform amount of light is delivered by the light devices. Thus, in the pre-defined illumination volume, the modular light devices can be configured to provide a substantially uniform amount of light according to a pre-defined specification. The size of the illumination volume and the intensity of light required to be delivered to the illumination volume can serve as factors in determining the number of light sources (e.g., LED light sources) included in each modular light device 1100.

In or more examples, the uniformity of the light within the illumination volume can be quantified as a function of the irradiance of the light sources. Thus, in one or more examples, a plurality of light sources can be collectively configured such that the light sources illuminate the biological fluid in the treatment chamber with less than 25% (e.g., less than 20%, less than 15%, less than 10%) variance in irradiance across a surface of the biological fluid (e.g., fluid container, fluid container intercept plane) facing the light sources. In one or more examples, the light sources are configured such that the light sources illuminate any 5 $cm^2$ area on the biological fluid (e.g., container with biological fluid) in the treatment chamber with less than 25% variance from the integrated irradiance (averaged over surface area) of the entire biological fluid (e.g., container with biological fluid) intercept plane.

In one or more examples, a surface of the biological fluid may be defined by, for example, a surface of a biological fluid container holding the fluid or a plane intersecting any portion of the biological fluid. In one example, the light sources may be configured (e.g., positioned in the array) such that the light sources illuminate a biological fluid with less than 25% (e.g., less than 20%, less than 15%, less than 10%) variance in irradiance across a surface of biological fluid facing the array of light sources. In other words, the light intensity at any one portion of the surface of biological fluid facing an array of light sources may differ from the light intensity at any other portion of the surface of the biological fluid facing the array of light sources by less than 25% (e.g., less than 20%, less than 15%, less than 10%).

In one or more examples, the modular light device 1100 can include 216 LEDs 1102 within an LED array chamber 1008. In one or more examples, the LED array chamber 1008 can include more or less LEDs. In addition to the illumination volume and the requirements of the treatment process, the number of LEDs can also be influenced by the size of the LED array chamber (e.g., distance of the array of LEDs from the window) 1008, the power specifications of the modular light device 1000, as well as a desired treatment time for the biological fluid being treated. For instance, in an example where the desired UV treatment dose for the biological fluid is 6.3 $J/cm^2$ from a desired combination of treatment time and intensity, 216 LEDs can provide the required light dose. However, in one or more examples, using less LEDs and/or lower intensity in a modular light device can reduce power needs but may require more time for the biological fluid to be treated. Conversely, using more LEDs and/or higher intensity in a chamber can decrease the amount of time needed for treatment, but can drive up the cost of power and temperature associated with an increased amount of LEDs and/or higher intensity. In one or more examples of the disclosure, the modular light device 1000 can include 5 or more, 10 or more, 25 or more, 50 or more, 100 or more, 150 or more, 200 or more, 250 or more, 300 or more, or 400 or more light sources (e.g., LEDs) within a light source array chamber 1008. In one or more examples of the disclosure, the modular light device 1000 can include 500 or less, 400 or less, 300 or less, 250 or less, 200 or less, 150 or less or 100 or less light sources (e.g., LEDs), such as for example 50 to 400, 100 to 300 or 150 to 250 light sources, within a light source array chamber 1008.

In one or more examples of the disclosure, and as illustrated in FIG. 11, the light source array chamber (e.g., LED array chamber) can include one or more light sensors (e.g., photodiodes) 1104 disposed on the printed circuit board(s) on which the LEDs themselves are disposed. The photodiodes 1104 can be included in addition to the photodiodes disposed on the flex circuit(s) 1006 described above (the photodiodes 1104 disposed on the flex circuit(s) 1006 are visible in the view provided by FIG. 12). In contrast to the photodiodes disposed on the flex circuit(s) 1006, the photodiodes 1104 can be oriented to capture light being transmitted by a second modular light device which is disposed on the opposite side of the treatment chamber (e.g., platform, treatment bag) from the modular light device 1000 and can thus configured to measure the light being transmitted by the second modular light device. As described above, the photodiodes on flex circuit(s) 1006 can be oriented and configured to capture light that is being directly transmitted by the modular light device itself towards the treatment chamber (e.g., platform, treatment bag).

In one or more examples, the modular light device 1100 can include a total of eighteen photodiodes, nine photodiodes 1104 which are disposed on the printed circuit board(s) (e.g., 3 per circuit board) of the light array chamber 1008, and the other nine disposed on the flex circuit(s) (e.g., 3 per flex circuit) 1006 described above. The number of photodiodes included in any given modular light device can be determined, for example, by the required measurement accuracy, configuration of the light source array(s), and space constraints posed by the modular light devices. Thus, in one or more examples, the modular light device may include more photodiodes that provide increased measurement accuracy but at the cost of for example, tighter spacing of the components or increased volume of the light engine. Conversely, the modular light device 1000 may include less photodiodes, which may, for example, reduce the footprint of the overall light device but at the cost of measurement accuracy. In one or more examples of the disclosure, the modular light device 1000 can include 2 or more, 4 or more, 6 or more, 8 or more, 10 or more, 15 or more, 20 or more, 25 or more or 30 or more photodiodes (e.g., disposed on either or both of the printed circuit board(s) and the flex circuit(s) described above). In one or more examples, the photodiodes can be connected to control electronics (described in further detail below) such that if it is determined that the modular light device is not producing the proper amount of light (or if the modular light device on the other side of the treatment chamber is not producing the proper amount of light) remedial actions can be taken by the device (for instance by alerting an operator to the condition, adjusting the intensity of light sources, adjusting electrical current to the light sources, terminating a treatment process). Alternatively, or in addition, in one or more example, the photodiodes can be connected to control electronics (described in further detail below) such that the presence or absence of a biological fluid in the treatment chamber can be determined based on the amount of light transmitted by the modular light device on the other side of the treatment chamber.

In one or more examples, the light array chamber 1008 of the modular light device 1000 can include one or more temperature sensors 1106. The temperature sensors 1106 can be configured to measure a temperature of the modular light device 1000. During operation of the modular light device, the light sources (e.g., LEDs), in addition to transmitting light energy, can also generate a significant amount of thermal energy. The temperature sensors 1106 can be configured to measure the heat given off by the LED light sources to ensure that they are operating with their specifications and/or the specifications for a biological treatment profile. In one or more examples, the temperature sensors can be connected to control electronics (described in further detail below) such that if it is determined that the modular light device is operating at a temperature beyond its specification, then the light device can be shut down or other remedial measures can be taken. In some embodiments, the LED light sources can be modulated, such as for example, cycling between on and off (e.g., pulse modulation), in response to a temperature measurement by the sensor(s). Temperature sensors (e.g., each temperature sensor) 1106 can be mounted, for example, to an LED junction (i.e., the junction between the LED and the PCB on which the LED is disposed upon) as portions of the LED are responsible for the majority of the heat generated by the light device. Alternatively, or in addition, temperature sensors (e.g., each temperature sensor) 1106 can be mounted, for example, to the printed circuit board of the light array chamber 1008. In one or more examples, the temperature sensors can be implemented using thermistors (or any other component configure to measure changes in temperature) that can change resistance in proportion to the temperature of the light array chamber 1008. Additionally, the one or more temperature sensors can be implemented using a variety of sensor types including: thermocouples, infrared sensors, bimetallic devices, thermometers, change-of-state sensors, and silicon diodes. In one or more examples, the modular light device 1000 can include a total of six temperature sensors. Similar to the photodiodes 1104, the light array chamber 1008 can include more or less temperature sensors (e.g., 1 or more, 2 or more, 3 or more, 4 or more, 5 or more, 8 or more or 10 or more). While more temperature sensors can mean higher measurement accuracy, it may come at, for example, the cost of space. Conversely, while less temperature sensors may, for example, take less space, it may come at the cost of measurement accuracy.

Figure 12:
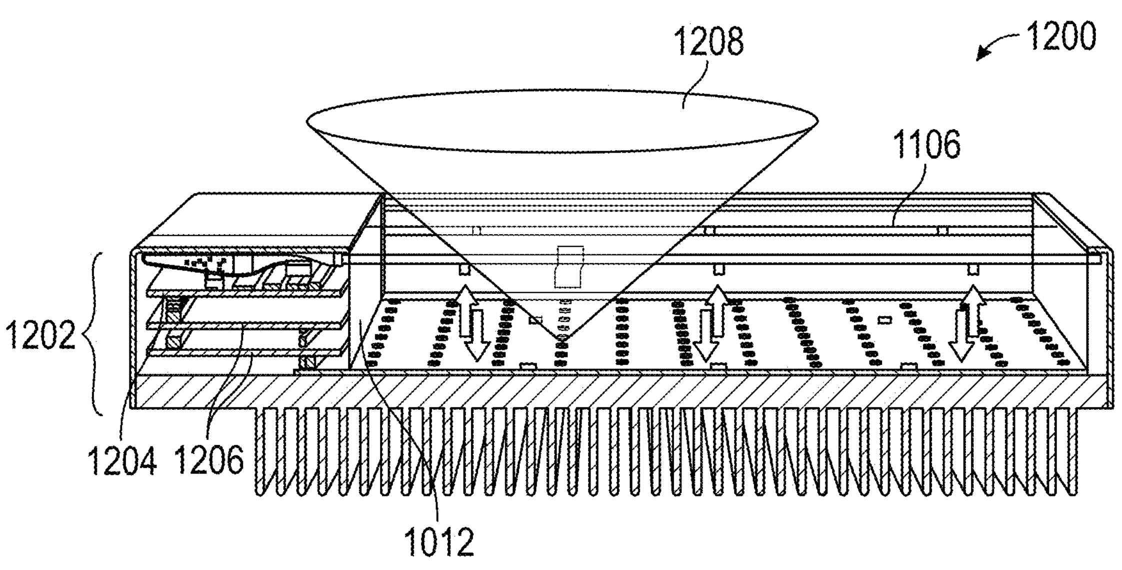
FIG. 12 illustrates a side view of an exemplary modular light device for use in a system for treating a biological fluid system according to examples of the disclosure.

FIG. 12 illustrates a side view (e.g., cut-away) of an exemplary modular light device for use in a system for treating a biological fluid (e.g., electronic treatment device) according to examples of the disclosure. The side view 1200 of light device 1000 provided in FIG. 12 can better illustrate some additional features of the light device according to one or more examples of the disclosure. For instance, as shown in side view 1200, the light device 1000 includes control circuitry 1202 contained within the housing of the light device 1002 (for purposed of illustration, the housing 1002 at the control circuitry has been removed to reveal the control circuitry). Control circuitry 1202, can include both a Controller PCB 1204 and one or more light source (e.g., LED) Driver PCBs 1206. In one or more examples of the disclosure, the Controller PCB 1204 can be configured to act as the "brains" of the light device. In one or more examples of the disclosure, the Controller PCB 1204 can facilitate communication between the broader treatment device and the light device 1000 itself and can be configured to operate the one or more LED PCBs 1206. In one or more examples of the disclosure, the Controller PCB 1204 can include one or more microprocessors, a memory, and a communications interface.

In one or more examples of the disclosure, the LED Driver PCBs 1206 can be configured to regulate the current and power of each LED 1102 disposed on a light source array of a light array chamber 1008. In one or more examples, the modular light device 1000 can include two LED Driver PCBs 1206, each driver including 18 driver chips configured to collectively regulate the current and power of the 216 LEDs 1102 disposed in the light array chamber 1008. In one or more examples, the LED Driver PCBs 1206 can be configured to ensure that the light device 1000 is compliant to the IEC 61010 standard. For instance, each driver of the LED Driver PCB 1206 can include its own temperature sensor. The number of LED Driver PCBs, as well as the total number of driver chips can be more or less and can be largely a function of the number of LEDs 1102 disposed in the light array chamber 1008. In one or more examples of the disclosure, each driver chip of the LED Driver PCB 1206 can include a dedicated temperature sensor configure to monitor the temperature of the modular light device. In another exemplary embodiment of the light device 1000, the control circuitry including Controller PCB 1204 and LED Driver PCB 1206 can be integrated onto the system-wide CSB controller described above. However, integrating these control units within the light device 1000 itself can make the design more modular in that replacing (e.g., upgrading) the light device can be a simple matter of swapping out the entire unit, rather than also having to access the system-wide CSB controller to upgrade the control electronics associated with the light device 1000.

The side view 1200 of FIG. 12 can also help to illustrate the beam angle 1208 of each individual light source (e.g., LED) disposed on the LED PCB 1206. In one or more examples, the beam angle of an LED can represent the angle at which the light generated by an LED is distributed or emitted. As discussed above, the LED arrangement can largely be influenced by the desired illumination surface area or volume of the treatment bag. Thus, in one or more examples, an LED with an appropriate beam angle 1208 can be selected so as to satisfy the illumination specification. In one or more examples of the disclosure the selected beam angle can be about 120° but the angle could be more or less (e.g., about 100° to about 140°, about 110° to about 130°, about 115° to about 125°, about 100°, about 110°, about 115°, about 125°, about 130°, about 140°. In one or more examples of the disclosure, each LED can achieve the desired beam angle by including a lens and/or packaging on each LED that can focus the light to the desired beam angle. Additionally, the side view 1200 can help to illustrate light sensors 1212 (e.g., photodiodes) of the flex circuit(s) 1006 disposed on the window 1004, and which are positioned facing the light sources on light source array(s) of the modular light device, to detect light emitted therefrom.

Figure 13:
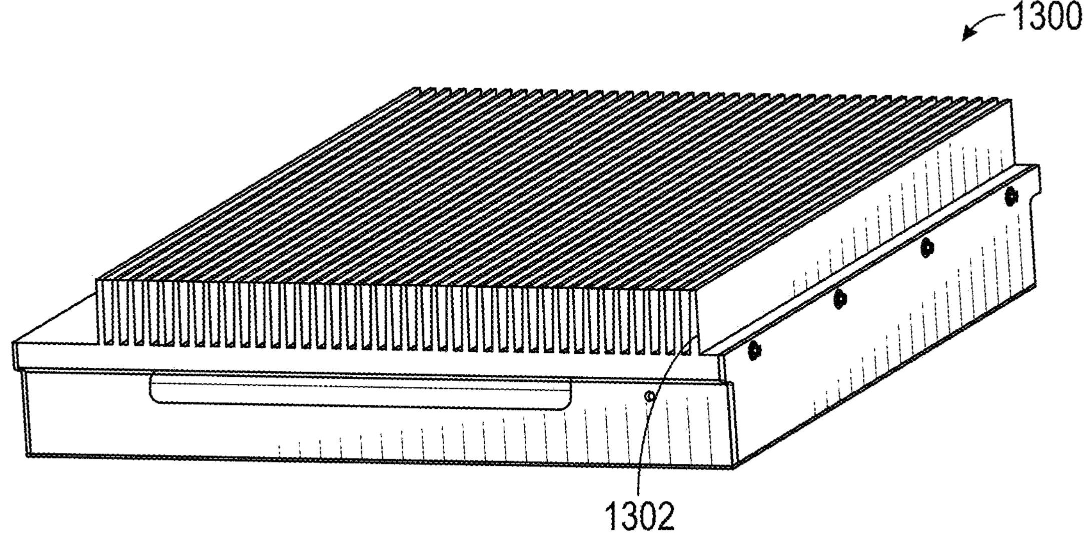
FIG. 13 illustrates a bottom view of an exemplary modular light device for use in a system for treating a biological fluid system according to examples of the disclosure.

FIG. 13 illustrates a bottom view of an exemplary modular light device for use in a system for treating a biological fluid (e.g., electronic treatment device) according to examples of the disclosure. The bottom view 1300 of light device 1000 provided in FIG. 13 can better illustrate the heat exchanger 1302 that can be configured to remove heat generated by the light device during operation. In one or more examples of the disclosure, the heat exchangers 1302 can be shaped so as to maximize the surface area of the device exposed to air being drawn or blown past the heat exchangers from one or more fans (e.g., external fans) located on the electronic treatment device. In one or more examples, the heat exchangers 1302 can be configured such that the air moving (e.g., blowing) past them from or to the fan(s) can be transferred from the light device 1000 to the passing air, therefore creating a cooling effect that lowers the overall temperature of the light source array and/or modular light device.

As shown in the example of FIG. 13, in one or more examples, the heat exchangers 1302 can be shaped as fins of a specific height and width While a large height and a large width can be selected so as to maximize the surface area exposed to air blowing past the heat exchanger, the larger height and width may increase the size footprint of the overall light device, and thus the height and width of the heat exchangers 1302 can be constrained by any size requirements imposed upon the light device. The shape of the heat exchangers 1302 can be configured to allow air being drawn or blown past the exchanger to circulate above and between the individual fins of the heat exchangers 1302. In this way, the amount of surface area exposed to the airflow is maximized.

In one or more examples, rather than using air to transfer heat away from the modular light device 1000, in one or more examples, the light device 1000 can include other forms of active cooling, such as for example, active cooling that circulates a liquid coolant (e.g., around the heat exchangers 1302) to cool the light device 1000. In one or more examples, the light device 1000 can also employ passive cooling to cool the light device, wherein the one or more heat exchangers 1302 are configured to utilize natural conduction, convection, and radiation to cool the light device 1000.

As indicated above, in one or more examples of the disclosure, the modular light device 1000 can include a plurality of heat sinks which are configured to exchange heat with air passing over them provided by one or more fans that are external to the light device (i.e., located on the treatment device). However, as discussed below, in one or more examples the light device 1000 can include its own fan or fans that is housed internally within the light device, and that can be part of the modular structure.

Figure 14:
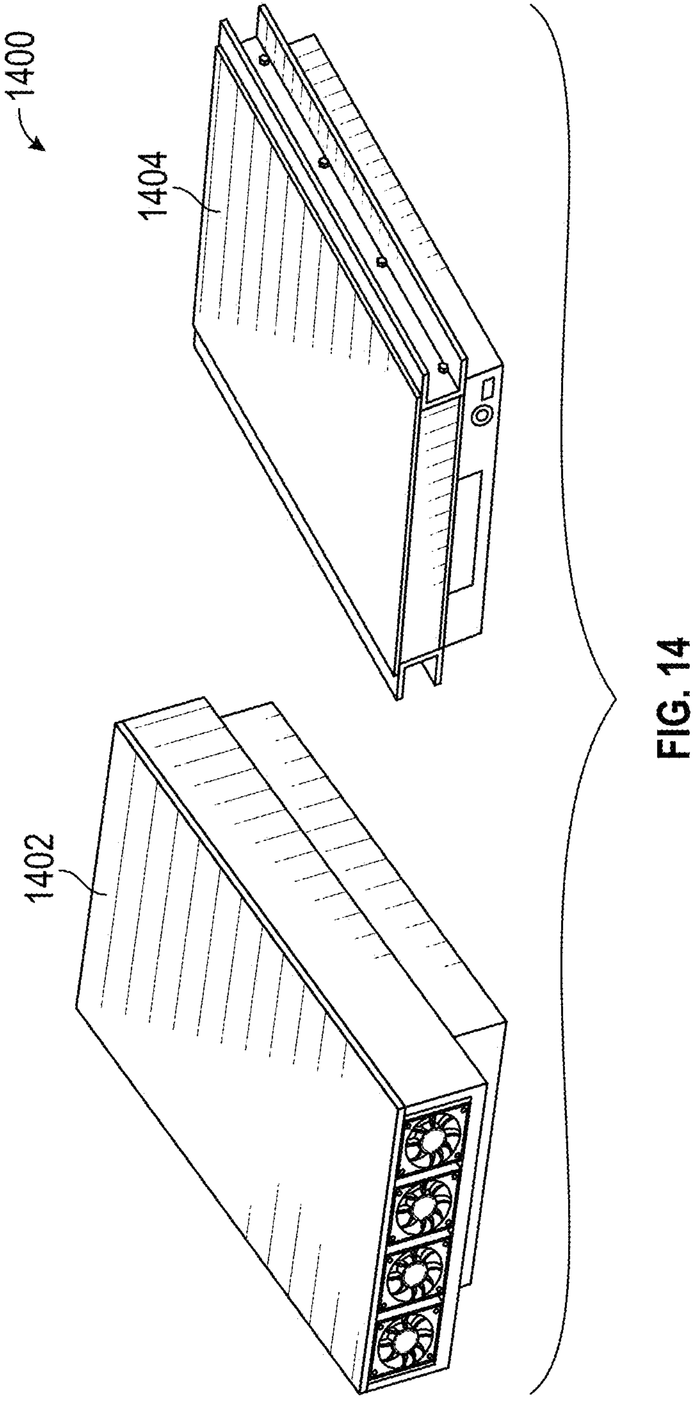
FIG. 14 illustrates exemplary thermal management architectures for implementing a modular light device for use in a system for treating a biological fluid system according to examples of the disclosure.

FIG. 14 illustrates exemplary fan architectures for implementing a light device for use in a system for treating a biological fluid according to examples of the disclosure. In one more examples, and as shown in FIG. 14, a modular light device 1402 can include one or more fans 1404 as part of the light device. In the example of light device 1402, the one or more fans 1404 can be configured to blow or draw air past the light source array chamber, such as for example, past a plurality of internal heat sinks or heat exchangers that are configured to exchange heat from the LEDs in the light device. Including the fans as part of the light device can lead to a more modular design, in that additional components that operate the light device 1402 are co-located in one light device. This can lead to more efficient modularity, as the light device itself can more directly control its own cooling mechanisms.

However, in one or more examples, including one or more fans as part of the modular light device 1402 can also add to the overall weight and size of the light device. For instance, and as illustrated in FIG. 14, a light device 1406 that does not include one or more fans as part of the light device can have a smaller size foot print than the light device 1402 that includes the fans as part of the light device. As an example, the light device 1402, which includes internal fans 1404 can have a larger height and weight than the light device 1406, which does not include internal fans. Thus, using a "fan-less" design, in which the light device relies on external fans (e.g., fans which are components of the electronic treatment device) or passive cooling can lead to a smaller and lighter light device that can make the design of the light device more modular (i.e., easier to replace). In one or more examples, a modular light device that does not include internal fans (e.g., "fan-less") may have a height of 6 inches or less, 5 inches or less, 4 inches or less, or 3 inches or less.

In order to support a modular design of a light device (i.e., allowing for the light device to be easily removed and replaced, for example, should it malfunction or otherwise not function according to desired operation, or be upgraded), the electronic treatment device itself can be configured to support the modularity of the light device. In other words, the treatment device can be configured to mechanically support the modular light device and facilitate its easy removal or addition. Configuring the treatment device to facilitate the efficient removal and replacement of a light device can make replacing a light device more efficient because it allows for a user servicing the device to simply "slide out" a modular light device (e.g., from the side, from the front, from the back) and "slide in" a replacement while only having to make a minimum number of electrical connections (e.g., power, ethernet, interlocks as described above).

Figures 15A, 15B:
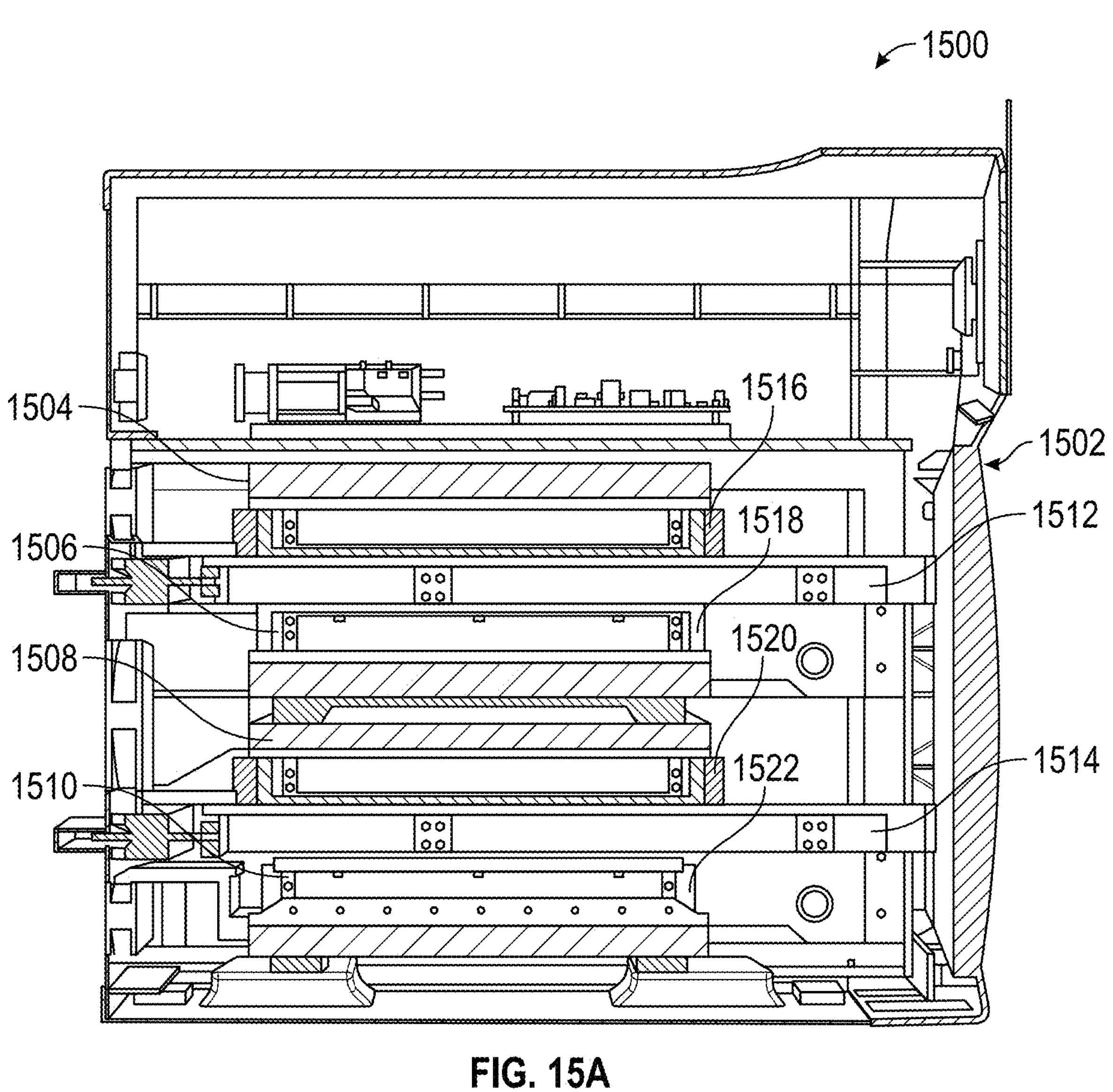
FIG. 15A illustrates another view of an exemplary internal hardware layout for a system for treating a biological fluid system according to examples of the disclosure.
FIG. 15B illustrates another view of an exemplary modular light device for use in a system for treating a biological fluid system according to examples of the disclosure.

FIG. 15A illustrates another view of an exemplary internal hardware layout for a system for treating a biological fluid (e.g., electronic treatment device) according to examples of the disclosure. The view 1500 of FIG. 15A represents a side view (e.g., cut-away) of the treatment device. In one or more examples, if a modular light device is to be replaced, then in one or more examples, a side panel of the treatment device can be removed as shown in FIG. 15A to provide access to the one or more modular light devices residing within the device. As illustrated in the side view 1500 of FIG. 15A, the treatment device 1502 can include four separate modular light devices 1504, 1506, 1508, and 1510. Similar to the examples described above, light devices 1504 and 1506 can be configured and disposed so as to provide substantially uniform light (e.g., UV light) to a treatment platform 1512 (e.g., and associated tray) and biological fluid positioned on the platform. Light devices 1508 and 1510 can be configured and disposed so as to provide substantially uniform light (e.g., UV light) to a treatment platform 1514 (e.g., and biological fluid positioned thereon).

In one or more examples, the electronic treatment device 1502 can include four separate sets (e.g., pairs) of mechanical rails 1516, 1518, 1520, and 1522 oriented in the direction of one side to the other side of the electronic device and that are configured to allow for each light device to slide into them so that the light devices are mechanically supported by the treatment device. In one or more examples, each set of rails 1516, 1518, 1520, and 1522 can include two rails disposed on opposite sides of the electronic device. FIG. 15 illustrates a single rail for each set of rails 1516, 1518, 1520, and 1522. The second rail for each set is disposed on the opposite side of the electronic device and is not visible in the figure. Thus, in one or more examples, the tracks provided on the housing of modular light device 1504 can be slid into the rails 1516 of the treatment device 1502 (e.g., from the side of the treatment device 1502) to mechanically support the light device 1504. The tracks provided on the housing of light device 1506 can be slid into the rails 1518 of the treatment device 1502 to mechanically support the light device 1506. The tracks provided on the housing of light device 1508 can be slid into the rails 1520 of the treatment device 1502 to mechanically support the light device 1508. Finally, the tracks provided on the housing of light device 1510 can be slid into the rails 1522 of the treatment device 1502 to mechanically support the light device 1510. By having a set of tracks on each modular light device that are complimentary to a set of rails on the treatment device, such that the light device can be slid into the treatment device during replacement, replacing a modular light device can be an efficient and easy process to execute.

FIG. 15B illustrates another exemplary view of a modular light device according to examples of the disclosure. The view 1524 of FIG. 15B can help to illustrate the tracks 1526 of the light device (discussed above with respect to FIG. 15A) that are, in one or more examples, configured to be slid on any one of the rails 1516, 1518, 1520 and 1522 of the treatment device 1502 so as to mechanically support the light device 1508. As shown in the view 1524 provided by FIG. 15B, the track 1526 can be shaped so that when slid on the rails 1516, 1518, 1520 and 1522, they can interlock with the rails so as to prevent slipping or lateral movement of the light device once the track 1526 has been placed on the rail 1516, 1518, 1520 and 1522.

In one or more of examples of the disclosure, the modular light devices can be subjected to a test process (e.g., health check process) to ensure that each of the modular light devices in an electronic treatment device are operating according to their requirements, that there is no light path obstruction or other occlusion (e.g., dust, scratch, contamination) on the window of the light device, and/or that there is no light path obstruction (e.g., dust, scratch, contamination) on the platform (e.g., associated tray) of the treatment device. In one or more examples, the test process (e.g., health check process) can be performed when a light device or light devices are first installed/replaced into a treatment device and/or can be performed intermittently throughout the operating lifetime of the device (e.g., before each treatment process). In one or more examples, the test process can be performed to determine the presence or absence of a biological fluid (e.g., container with biological fluid) to be treated (e.g., in a treatment chamber, on a platform, of the electronic treatment device).

Figure 16:
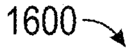
FIG. 16 illustrates an exemplary modular light device test process according to examples of the disclosure.
Figure 16:
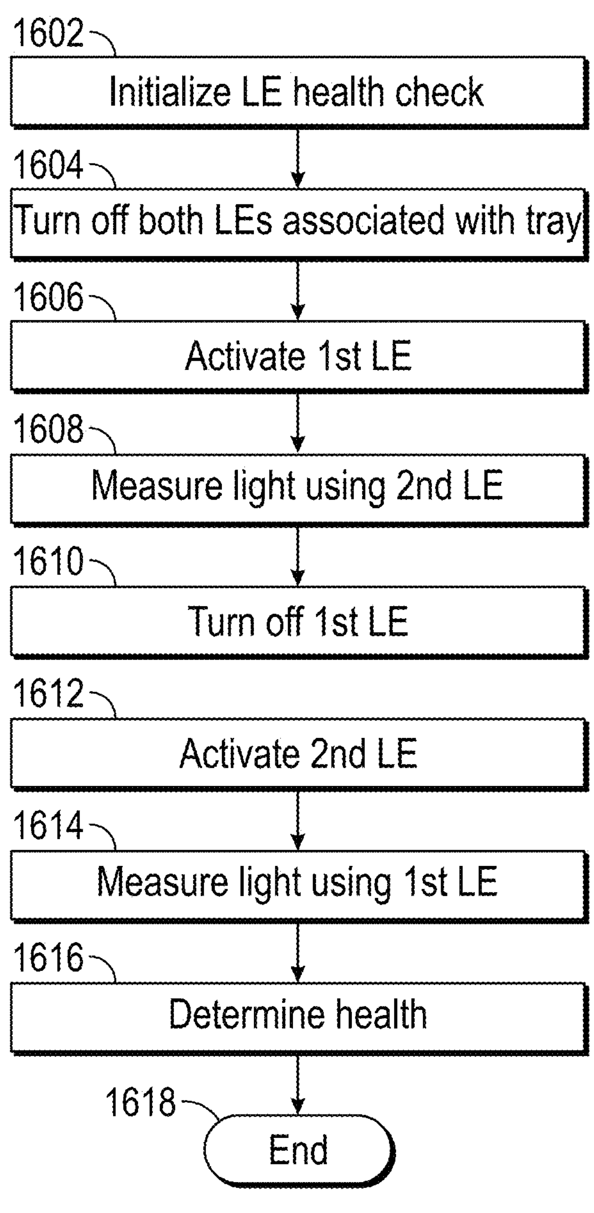

FIG. 16 illustrates an exemplary modular light device test process (e.g., to determine if there is any window and/or platform obstruction or other occlusion (e.g., contamination) such that the light is not fully and/or uniformly illuminating the treatment sample) according to examples of the disclosure. In one or more examples of the disclosure, the process 1600 depicted in FIG. 16 can begin at step 1602 wherein one or more processors either associated with the light device itself or associated with the treatment device generally can initiate a light device and/or treatment device check process. In one or more examples, the light device and/or electronic treatment device test process (e.g., health check process) may be initiated when there is no biological fluid being treated in the device and there is no biological fluid loaded on a platform (e.g., into an associated tray). In this way, the light device health check process will not interfere with the overall treatment process as it is executed at time when no treatment is occurring, nor will the presence of a biological fluid positioned on the platform interfere with the health check process.

Once the process has been initiated at step 1602, the process 1600 can move to step 1604, wherein both of the light devices associated with a single platform (e.g., associated tray) (see discussion above) are both switched off (e.g., if currently on), such that neither light device is transmitting light. Once both light devices associated with a platform are off or have been shut off at step 1604, the process 1600 can move to step 1606 wherein a first light device of the two light devices is activated. As will be evident from the discussion below, by turning on only one light device at a time to perform the health check, the precise source of the light being measured during the health check can be known. In contrast, if both light devices are simultaneously activated during a health check, it may be difficult to ascertain or precisely measure where the measured light is coming from.

Once the first light device is activated at step 1606, the process 1600 can move 1608 wherein the light coming from the first light device (e.g., passing through the platform of the treatment chamber) can be measured using the photodiodes on the second light device. As discussed above, the one or more photodiodes disposed directly on the light arrays (e.g., LED PCB's) are oriented to specifically capture light being transmitted from another light device on the opposite of the platform (e.g., and associated tray). In contrast, the one or more photodiodes located on the flexible circuits (described above) can be oriented to measure the light being transmitted by the light device itself. In one or more examples of the disclosure, the photodiodes on the flexible circuits of the first light device can also measure light coming from the same (e.g., first) light device.

Once the light being transmitted by the first light device is measured by the second light device at step 1608, the process can move to step 1610 wherein the light sources (e.g., LEDs) of the first light device can be shut off. Once shut off, the process can move directly to the step 1616 (described below) or to step 1612 wherein the light sources (e.g., LEDS) of the second light device are activated (e.g., to check the health of the second light device and/or electronic device). Once the second light device is turned on at step at step 1612, the process 1600 can move to step 1614, wherein the light transmitted by the second light device (e.g., passing through the platform of the treatment chamber) can be measured by the one or more photodiodes of the first light device in a manner substantially similar to the process described above with steps 1606-1610. In one or more examples of the disclosure, the photodiodes on the flexible circuits of the second light device can also measure light coming from the same (e.g., second) light device.

Once the light from the from the second light device is measured by the first light device at step 1614, the process 1600 can move to step 1616 wherein a determination is made on the health of the light device(s) and/or electronic device (e.g., platform), based on the measurements acquired at steps 1608 and 1614. In one or more examples, if it is determined that one or more of the light devices, or the electronic device, fails to pass the health test, the treatment device can send the user an alert in the form of a graphical user interface (GUI) shown on a display of the treatment device. After the health of the light device(s) is determined at step 1616, the process 1600 can move to step 1618 wherein it is terminated.

While the process described above with respect to FIG. 16 can determine whether the health of each modular light device, as well as if the light from each light device is being transmitted to (e.g., through) the platform (e.g., and associated tray) that would carry a treatment container, in one or more examples, the health check described above may not be adequate to determine if the desired dose of light (e.g., illumination volume) is being achieved. For instance, the process described above with respect to FIG. 16 may not be able to measure (e.g., adequately measure) the total dose of light delivered (e.g., to the surface of a biological fluid, to an illumination volume) as the process above is configured to determine if the light sources (e.g., LEDs) of each light device are transmitting light, and that there are no occlusions that are blocking the light being transmitted. Thus, in one or more examples, a calibration procedure can be performed intermittently throughout the operating lifecycle of a light device, to determine if the individual and/or combined light devices are providing a desired dose of light (e.g., producing the proper illumination volume, producing the proper irradiance). Based on such a calibration procedure, adjustments can be made, such as for example, increasing the intensity of one or more light sources (e.g., LEDs) to compensate for decreased efficiency of the light over time. In one embodiment, such an increase in intensity allows for the device to maintain (e.g., operator to experience) a substantially unchanged treatment processing time throughout the life cycle of the light sources.

Figure 17A:
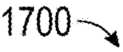
FIG. 17A illustrates an exemplary calibration process according to examples of the disclosure.
Figure 17A:
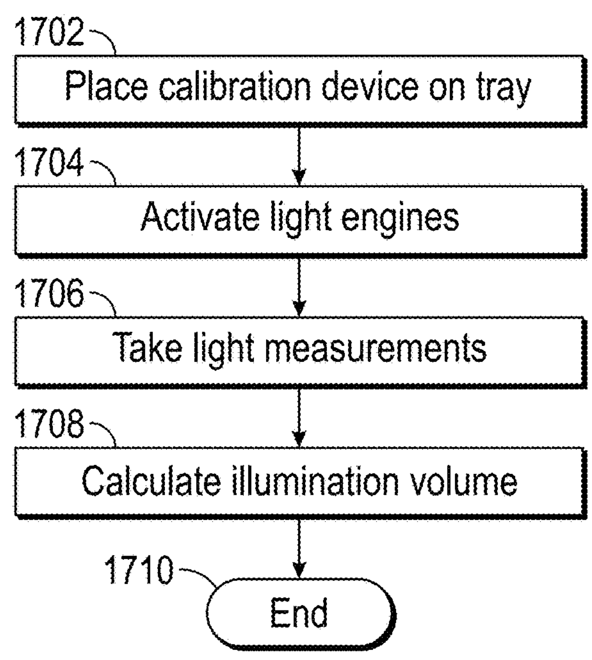

FIG. 17A illustrates an exemplary light device calibration process according to examples of the disclosure. The process 1700 can utilize a calibration device that can be implemented as a component (e.g., independent from the modular light device, independent from the electronic device) that is configured to be placed on a platform (e.g., and associated tray) of the device and is configured with a plurality of photodiodes or other light sensors that can measure the amount of light received from one or both modular light devices and calculate various factors including total dose of illumination delivered (e.g., illumination volume). In one or more examples, the process 1700 for calibrating the light devices can begin at step 1702 wherein the calibration device is placed on the platform (e.g., associated tray) of the treatment device (that normally holds the biological fluid/treatment container during operation of the treatment device).

In one or more examples, once the calibration device has been placed in position on the platform at step 1702, the process 1700 can move to step 1704 wherein one or more light devices configured to illuminate the platform are activated (i.e., the LEDs of light device(s) are turned on and transmit light to the calibration device). After one or more light devices have been activated at step 1704, the process 1700 can move to step 1706 wherein the one or more light measurement devices of the calibration device (i.e., photodiodes) can record measurements regarding the light received from the one or more light devices. In one or more examples, once the measurements have been taken at step 1706, the process 1700 can move to step 1708 wherein the calibration device (or a processor connected to the calibration device) can calculate the amount of illumination (e.g., light dose, illumination volume). In one or more examples, at step 1708, the calibration device can transmit an indication to the user of the device as to whether the device received a proper amount of light during the test, or whether the test failed. Once the illumination is calculated at step 1708, the process 1700 can move to step 1710 wherein it is terminated.

Figure 17B:
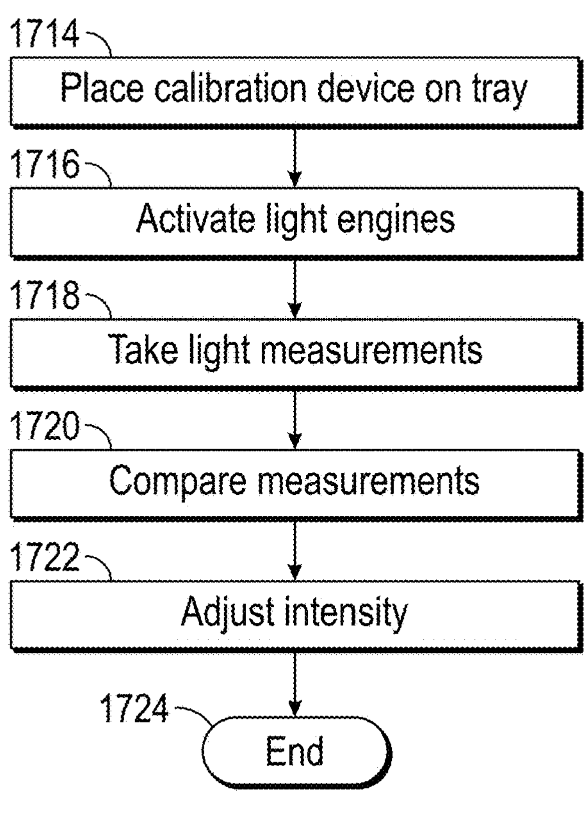
FIG. 17B illustrates another exemplary calibration process according to examples of the disclosure.

FIG. 17B illustrates another exemplary calibration process according to examples of the disclosure. In one or more examples, the process 1712 of FIG. 17B can be substantially similar to the process of FIG. 17A. For instance, steps 1714, 1716, and 1718 can be substantially similar to steps 1702, 1704, and 1706 of FIG. 17A. Thus, the discussion of steps 1702, 1704, and 1706 above can be referenced to understand the details of steps 1714, 1716, and 1718 respectively. In one or more examples, once the light measurements are taken at step 1718, the process 1714 can move to steps 1720 wherein the measurements obtained at step 1718 can be compared against a pre-determined threshold (e.g., a pre-determined about of light). In one or more examples, the pre-determined threshold can represent a value, which if a measurement taken at step 1718 falls below, would indicate that the current treatment time that the device requires for pathogen inactivation would not be adequate (e.g., insufficient illumination, insufficient light dose). In one or more examples, the pre-determined threshold can be empirically determined. In one or more examples, the calibration device can obtain the measurements and transmit the measurements to the treatment device or modular light device (e.g., by way of the electronic device) to perform the comparison of step 1720. Additionally or alternatively, the calibration device itself can perform the comparison of step 1720.

In one or more examples, in response to a calibration test in which the measurement taken at 1718 differs from an expected or desired amount (e.g., the pre-determined threshold at step 1720, an adjustment can be made to the light emitted by one or more light sources of the light device, such as for example, based on communication between the electronic device and the light device. In one or more examples, in response to a calibration test in which the measurement taken at 1718 falls below the pre-determined threshold at step 1720, the device can extend the treatment time to compensate for the lower amount of light received at the biological fluid during a treatment process. However, in one or more examples, extending the treatment time may not be desired, since it could lower the overall efficiency and productivity of the treatment device. Thus in one or more examples, if the measurement taken at step 1718 falls below a pre-determined threshold at step 1720, then in one or more examples, the process 1714 can move to step 1722 wherein the intensity of the light sources used during the calibration process 1714 (e.g., light sources of the light device) can be adjusted (i.e. increased) to account for (e.g., compensate for) the lower amount of light. In this way, rather than having to increase the treatment time to account for low light output from the light sources, the intensity of the light sources can be increased thereby leaving the treatment time substantially constant throughout the life of the light device. In the example, wherein the calibration device performs the comparison described about with respect to step 1720, then in one or more examples, the calibration device can transmit an indication to the electronic device to adjust the intensity as discussed above with respect to step 1722.

The modular light device can be considered a safety-critical component insofar as failure or malicious operation of the light device can lead to a failed (e.g., not meeting specified criteria) or unsafe treatment process. In one or more examples, if a modular light device fails or a malicious user gets access to the light device such that they can directly control it, then the biological fluid being treated can be compromised or rendered unsafe for use. Thus, as described in detail below, the modular light device described above can be configured to operate in a broader electronic treatment device, and can be configured to be compatible with one or more features of the treatment device (such as safety features, modular component aspects, and/or a domain-specific communications protocol) described below.

Figure 18:
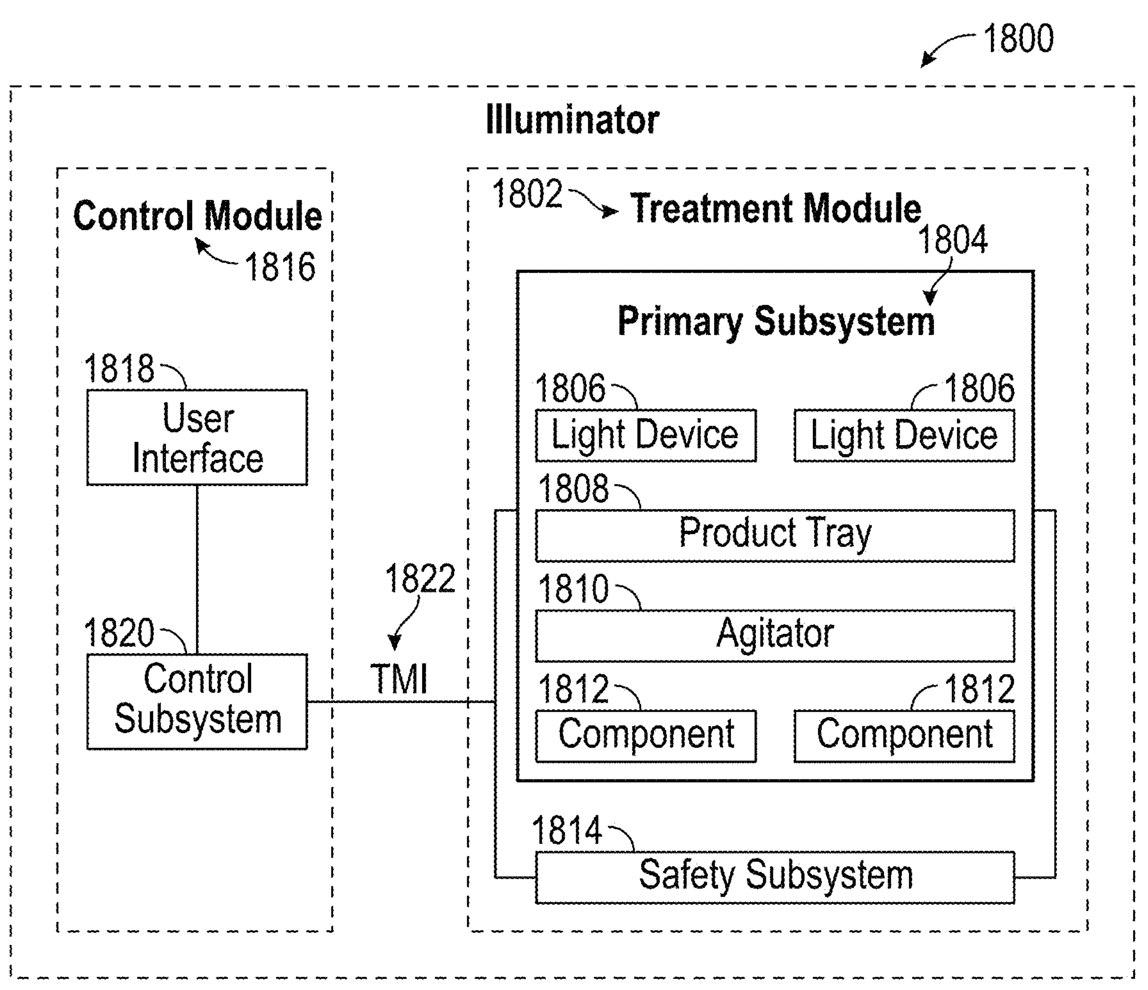
FIG. 18 illustrates an exemplary system diagram of an illuminator system for treating biological fluids according to examples of the disclosure.

FIG. 18 illustrates an exemplary system diagram of an illuminator system (e.g., electronic treatment device) for treating biological fluids according to examples of the disclosure. In or more examples, the biological fluids treated by the system 1800 can include one or more of platelets, plasma, blood, and a blood product. As described above with respect to FIGS. 1-3 the device can treat a biological fluid by exposing the fluid to illumination with light (e.g., ultraviolet light), such as in or more examples having wavelengths in the ultraviolet-A (UV-A), UV-B, and/or UV-C spectrum. In order to treat the fluids using light, the device can be configured to deliver light (e.g., ultraviolet light, UVA light) to the biological fluid at specified intensities for a determined time period (e.g., to achieve a desired light dose) for the purpose of pathogen inactivation. In one or more examples, the device can treat with light (e.g., UV light) a biological fluid admixed with a pathogen inactivation compound (e.g., photoactive compound).

In one more examples of the disclosure, the system 1800 can include a control module 1816 and a treatment module 1802. In one more examples of the disclosure, the treatment module 1802 can include two subsystems: (1) a primary subsystem 1804 and a safety subsystem 1814. In one more examples of the disclosure, the primary subsystem 1804 can include the components and systems that carry out the light treatments (e.g., UVA light treatments), while the safety subsystem (described in detail below) can include components and systems that are configured to monitor the activities performed by the primary subsystem 1804.

In one more examples, the primary subsystem 1804 may contain one or more modular light devices 1806 that include the light source(s) (e.g., light source array(s)) for treating the biological fluid. Each modular light device 1806 may include one or more light sources that can be configured to emit variable intensity of light (e.g., UVA light) and are positioned within the device so that when the light source is emitting, the biological fluid within the device is exposed to the light (e.g., light waves) emanating from the light source. In some examples of the disclosure, the biological fluid may be contained within a container (e.g., bag), and can be positioned within the device, such as for example on a platform (e.g., and associated tray), so that it can be exposed to the light (e.g., light waves) emanating from the light source.

The primary subsystem 1804 may also include one or more chambers (not shown) to receive treatment containers (e.g., bags) containing the biological fluid to be treated. The treatment container may be placed on a platform (e.g., associated product tray) 1808 within a treatment chamber. Each treatment chamber may have one or more modular light devices associated with it. For example, each chamber may receive light (e.g., UVA light) from one or multiple light devices 1806 to treat the biological fluid in the treatment container within the treatment chamber. In one more examples, treatment may be simultaneously performed on multiple treatment containers (e.g., bags) in multiple treatment chambers.

In some examples, the primary subsystem may include an agitator 1810. The agitator 1810 may be used to agitate the contents of the treatment container to distribute (e.g., evenly distribute) the biological fluid and/or a pathogen inactivation compound in (e.g., in admixture with) the biological fluid. The primary system may further contain miscellaneous components 1812 to perform various other functions that aid the treatment process. These functions may include, but are not limited to, one or more sensors (e.g., to detect light, light intensity, light dosage), detection of placement of the treatment container and marking mechanisms to demonstrate treatment has occurred on a particular treatment container.

In some examples of the disclosure, the safety subsystem 1814 within the treatment module 1802 may be used to monitor the treatment activities occurring in the primary subsystem 1804. The safety subsystem 1814 functionalities may include, but are not limited to, interlocks, lockouts, hardware and software watchdogs and the like.

In some examples, illuminator treatment system 1800 may contain a control module 1816 which may enable a user to make a treatment request and interact with the illuminator system 1800. In some examples, the control module 1816 may be physically separate from the illuminator system 1800. When physically separate, the control module 1816 may be connected to illuminator system 1800 through wires or wirelessly using a pre-determined wireless communication standard such as, for example, Bluetooth or WiFi. In some examples, one control module 1816 may be associated with multiple systems like illuminator system 1800.

In one or more examples of the disclosure, the control module 1816 may include a user interface 1818. The user interface 1818 may be a display that enables the user to interact with the illuminator system 1800. In one or more examples, the user interface 1818 can be implemented as an LCD display with a touch screen interface that utilizes user selectable buttons, icons, and text so as to facilitate user interaction with the device. The user interface may include input-output devices like a touch pad, a keyboard, a mouse, a camera to read bar codes etc.

In one more examples of the disclosure, the system 1800 can include a common interface 1822. In some examples, the system 1800 is an electronic device for treating a biological fluid and the common interface 1822 is a treatment interface of the electronic device.

In some embodiments, the common interface 1822 is communicatively coupled to the control module 1816 (e.g., control subsystem 1820 of the control module 1816), the primary subsystem 1804, and the safety subsystem 1814. The common interface 1822 can be configured to provide a communication pathway between the control module 1816 and the primary subsystem 1804 or the safety subsystem 1814. In some embodiments, communications between the control module and a subsystem is caused by an input to the user interface 1818. In some embodiments, communication between the control module and a subsystem is caused by an introduction of a subsystem or a component into the illuminator system (e.g., a modular light device is installed into the system).

The modules and components and systems above can each include various components associated with their functionality. These components can be arranged in a system architecture that can allow for those components to be coordinated with one another so as to facilitate effective and efficient treatment of the one or more biological fluids.

Figure 19:
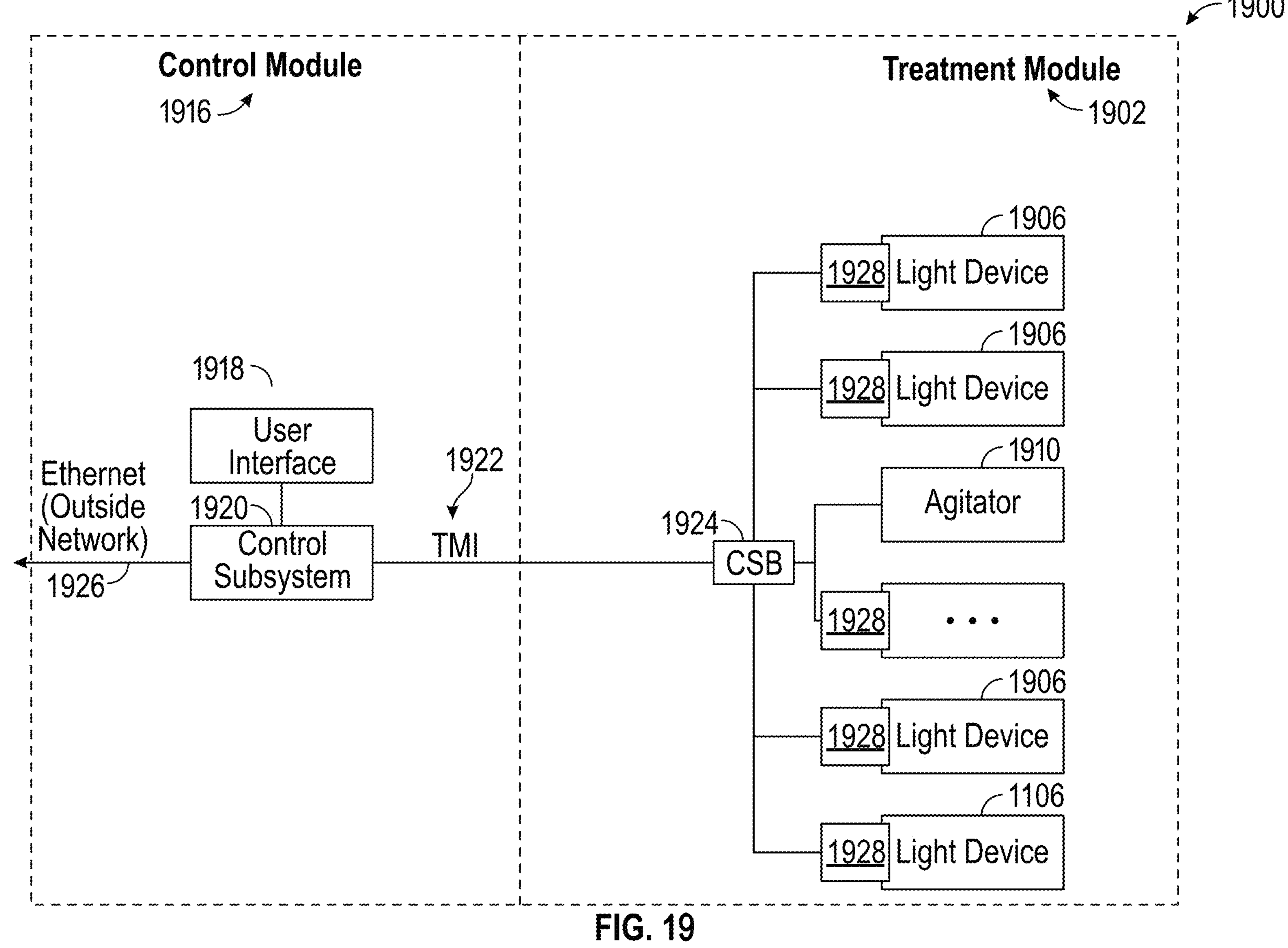
FIG. 19 illustrates another exemplary system diagram of an illuminator system for treating biological fluids according to examples of the disclosure.

FIG. 19 illustrates another exemplary system diagram of an illuminator system for treating biological fluids according to examples of the disclosure. In some examples of the disclosure the system architecture 1900 can include a control module 1916 and a treatment module 1902. The control module 1916 may include a control subsystem 1920, which may perform various functions. For example, the control subsystem 1920 may manage the graphic icons, screen transitions, button presses and other user interactions at the user interface 1918. It may print records of treatments that have occurred. It may act as a communications manager by interacting with a network external to the illuminator system 1900, such as for example, through Ethernet. In one or more examples, the control subsystem 1920 may also act as a data manager by maintaining a database of treatments that have occurred. In one or more examples, the control subsystem 1920 can also act as an event log manager by recording different events that occur (e.g., inside and/or outside) the illuminator system 1900. These events may include, but are not limited to, normal and abnormal environmental conditions, alarms, malfunctions and the like. In one or more examples, the controller may be a CPU or a microprocessor, and may include volatile and non-volatile memories.

In one or more examples, the control subsystem 1920 may enable communication between the control module 1916 and the outside network through a port (e.g., Ethernet port) 1926. For example, any devices external to the illuminator system 1900 can be connected to the control subsystem 1920 through port 1926. These devices may include, but are not limited to, an external personal computer, an external blood management system to transmit data in and out of illuminator system 1900 and the like. For example, a blood management system may gather reports from the illuminator system 1900. It may also transmit software and data into illuminator system 200 to perform different control functions. These functions may include, but are not limited to, programming illuminator system 1900 with different treatment profiles and user information, performing maintenance and health checks (e.g., diagnostics) of illuminator system 1900, and the like.

In one or more examples, the control module 1916 can be isolated from the treatment module 1902 with the help of a common interface 1922 (described in further detail below). For example, such isolation may help physically separate the critical functionality in the treatment module 1902 from the non-critical functionality in the control module 1916. In one or more examples of the disclosure the isolation between critical and not critical components may enable putting safety critical software and hardware that requires more stringent testing in treatment module 1902, and non-safety critical software and hardware that requires less stringent testing in control module 1916. In this way, the impact engendered by a replacement or modification to non-critical components to critical components of the device can be minimized.

In some embodiments, the common interface enables communication between the control module 1916 and the treatment module 1902 through the use of a predefined domain specific communication protocol. For example, the control subsystem 1920 (which can, in one or more examples be implemented as a controller) in the control module 1916 may communicate with a separate controller 1924 in the treatment module 1902.

In one or more examples, the control subsystem 1920 can be communicatively coupled to one or more non-safety critical components located in the control module 1916 and can also be communicatively coupled to the treatment module 1902 via controller 1924. Controller 1924 in the treatment module 1902 can be communicatively coupled to one or more safety critical components such as the light device 1928 and agitator 1910 and can also be communicatively coupled to the control subsystem 1920 of the control module 1916.

In one or more examples, the control subsystem's 1920 only interface with the components of the treatment module 1902 can be through the controller 1924, while the controller 1924's only interface with the components in the control module 1916 can be through the control subsystem 1920. In this way, isolation between the non-safety critical component in the control module 1916 and the safety-critical components in the treatment module 1902 can be maintained. By maintaining this isolation through the use of two separate controllers, the impact caused by future changes to the components (i.e., change to or expansion of components) within the control module 1916 to the treatment module 502 can be minimized. Thus, changes in the control module 1916 may not require having to engage in burdensome retesting of components in the treatment module 1902 that have to pass regulatory scrutiny. Furthermore, by using a predefined domain-specific communications protocol 1922 to facilitate communications between the control subsystem 1920 and the controller 1924, further isolation between the non-safety critical components in control module 1916 and treatment module 1902 can be further maintained. The domain-specific interface protocol 522 used to communicate between control subsystem 1920 and controller 1924 can mean the way that the two modules 1916 and 1920 will remain consistent despite any changes in the components that make up control module 1916 and treatment module 1902.

In one or more examples, the controller 1924 may perform the safety related functions in the treatment module 1902. For example, the controller 1924 may monitor that the illuminator system 1900 is handled in a safe and proper manner and may implement an interlock or lock out mechanism when unsafe or improper conditions are detected. The controller 1924 may also implement alarms programmed to indicate errors that occur during the treatment process and indicate alarm information to the user through the user interface 1918. In some embodiments, the controller 1924 may also perform treatment tasks by managing the different components in the illuminator system 1900 according to a particular treatment profile. For example, the controller 1924 may control how much light energy (e.g., UVA energy) the biological fluid (e.g., treatment bag containing the biological fluid) is exposed to by controlling the on-off times of the modular light devices 1906 and the intensity of the light. In some examples, the controller 1924 may also control the wavelength of light emitted by the light devices and/or the speed of the agitator 1910. In some embodiments, the controller 1924 may be a single board computer or a custom Printed Circuit Board with a processor. The controller 1924 may include volatile and non-volatile memories.

In one or more examples of the disclosure, the illuminator system 1900 may include one or more smart components 1928. These smart components 1928 can include components like the modular light devices 1906, controller 1924, user interface 1918, control subsystem 1920, but with inbuilt computing hardware that is independent to each component. Each smart component's computing hardware may be programmed to perform functions that are unique to that component. For example, the computing hardware in controller 1924 may execute algorithms to manage interactions between all the components to carry out the treatment process. In some embodiments, the light device 1906 smart component may have an algorithm for monitoring the light (e.g., UV) energy delivered and adjusting treatment times and dose rates. Additionally, the light device 1906 may be able to take directions and commands from the controller 1924. In some embodiments, the computing hardware in smart components 1928 may be implemented using a custom Printed Circuit board, an FPGA, an ASIC and may include volatile and non-volatile memories.

In one or more examples of the disclosure, the illuminator system 1900 may include one or more sensors (not shown). For example, the modular light device 1906 may include a light sensor (e.g., photodiode) to detect the amount (e.g., total dose) of light (e.g., light energy) emitted by the light source(s) (e.g., exiting the LEDs) in the light device 1906 and/or the amount of light (e.g., light energy) delivered to a biological fluid, e.g., in a treatment container. Other examples of sensors may include, but are not limited to proximity sensors, weight sensors, air sensors, temperature sensors and the like.

In some examples, the system 1900 is an electronic device for treating a biological fluid and the common interface 1922 is a treatment interface of the electronic device. In some examples, a control module (e.g., control module 1016, control module 1916) of the system includes a first controller and a second controller. The first controller can be communicatively coupled to a plurality of non-safety critical components, such as the ones described herein, and the second controller can be communicatively coupled to a plurality of safety critical components, such as the ones described herein, through the treatment interface.

In some embodiments, in response to communicatively coupling the plurality of non-safety critical components to the treatment interface and communicatively coupling the plurality of safety-critical component to the treatment interface, the system detects, with the control module, presences of the plurality of non-safety critical component and the plurality of safety-critical component in the electronic device.

In some examples, the system can transmit first messages associated with the non-safety critical components between the first controller and the non-safety critical component through the treatment interface, and the system can transmit second messages between the second controller and the safety-critical component through the treatment interface. In some embodiments, the first and second messages are based on a domain-specific interface language. For example, the domain-specific interface language is TCP/IP. In some embodiments, in response to receiving a message, the controller module or the component may send a response (e.g., message accepted, message rejected, message missing information, receiver is busy) to the sender to acknowledge receipt of the respective message.

In some examples, the system determines states of the non-safety critical components based on the first messages and states of the safety critical components based on the second messages. For example, the states can be one or more of "uninitialized," "initializing," "ready," "running," "calibrating," "shutting down," "servicing," and "fault." It is understood that the states are not limited to the ones described herein.

In some examples, the message may include a message header and message data. The message header can include information associated with: one or more commands, a transaction number, message type, and message size. The message data can include information associated with one or more of states described herein.

In some embodiments, the message can include information about the system. For example, the information about the system can include a treatment dosage associate with a biological fluid being treated, a maximum treatment time of the biological fluid, a maximum hold time after the treatment completes, a data update interface (e.g., how often the system is being informed about treatment progress), speed of a component (e.g., agitator current speed in Hz). It is understood that the listed information are exemplary and are not limiting. In some embodiments, the information in the message are parameters defined by a user (e.g., information derived from user defined treatment parameters).

In some examples, the message can include information about a treatment. For examples, the information about a treatment can include treatment elapsed time, dosage applied, chamber temperature, biological fluid temperature, and speed of a component (e.g., agitator current speed in Hz). It is understood that the listed information are exemplary and are not limiting.

In some examples, the message can include information to cause the system to cancel a run (e.g., stop treatment). In some examples, the message can include information to notify the system that a run has completed (e.g., treatment has finished) and data (e.g., statistics) associated with the completed treatment.

In some embodiments, the message can be associated with servicing of the system. In some examples, the message can be a request to begin service on the system. In some examples, the message includes information about a current service (e.g., maintenance) being performed on the system. In some examples, the message includes information about a completed service (e.g., a notification, service log).

In some embodiments, the message can be associated with system shutdown (e.g., a request to shut down the system, a request to shut down the system at a specific time). In some embodiments, the message can be associated with a system fault (e.g., identification of a faulty component, instruction for fault recovery, log associated with the fault). In some embodiments, the message can be associated with system calibration (e.g., transfer of a calibration file, transfer of a configuration file). In some embodiments, the message can be associated with a version of a subsystem or a component (e.g., interface version, firmware version, OS version, BIOS version, hardware version, component version, subsystem serial number). For example, messages associated with subsystem or component versions can ensure the system's safety, reliability, or compatibility requirements are up-to-date.

In some examples, the non-safety critical components or the safety critical components can change states. For example, a non-safety critical component or a safety critical component is in a first state. The system can change the state (e.g., in response to user input) of the non-safety critical component or the safety-critical component from the first state to a second state. In some examples, in response to the changing the state, the system sends, from of the non-safety critical component or the safety-critical component to the control module through the common interface, a second message (e.g., different from the first message). In some embodiments, the system receives, at the first controller or the second controller, the second message, and in response to receiving the second message, the system determines a second state of the treatment component.

In some examples, power is provided to the system and the presences of the plurality of non-safety critical component and the plurality of safety-critical component are detected in response to the providing of power to the system. For example, during power on and system initialization, the presences of these components are detected.

In some examples, in response to power being provided to the system, the system assigns local network addresses (e.g., IP addresses, MAC addresses) and ports (e.g., TCP ports) to the plurality of non-safety critical components and the plurality of safety-critical components. In some embodiments, the local network addresses and the ports are based on a domain-specific interface language. For example, the local addresses can be IP addresses or MAC addresses, and the local ports can be TCP ports.

Figure 20:
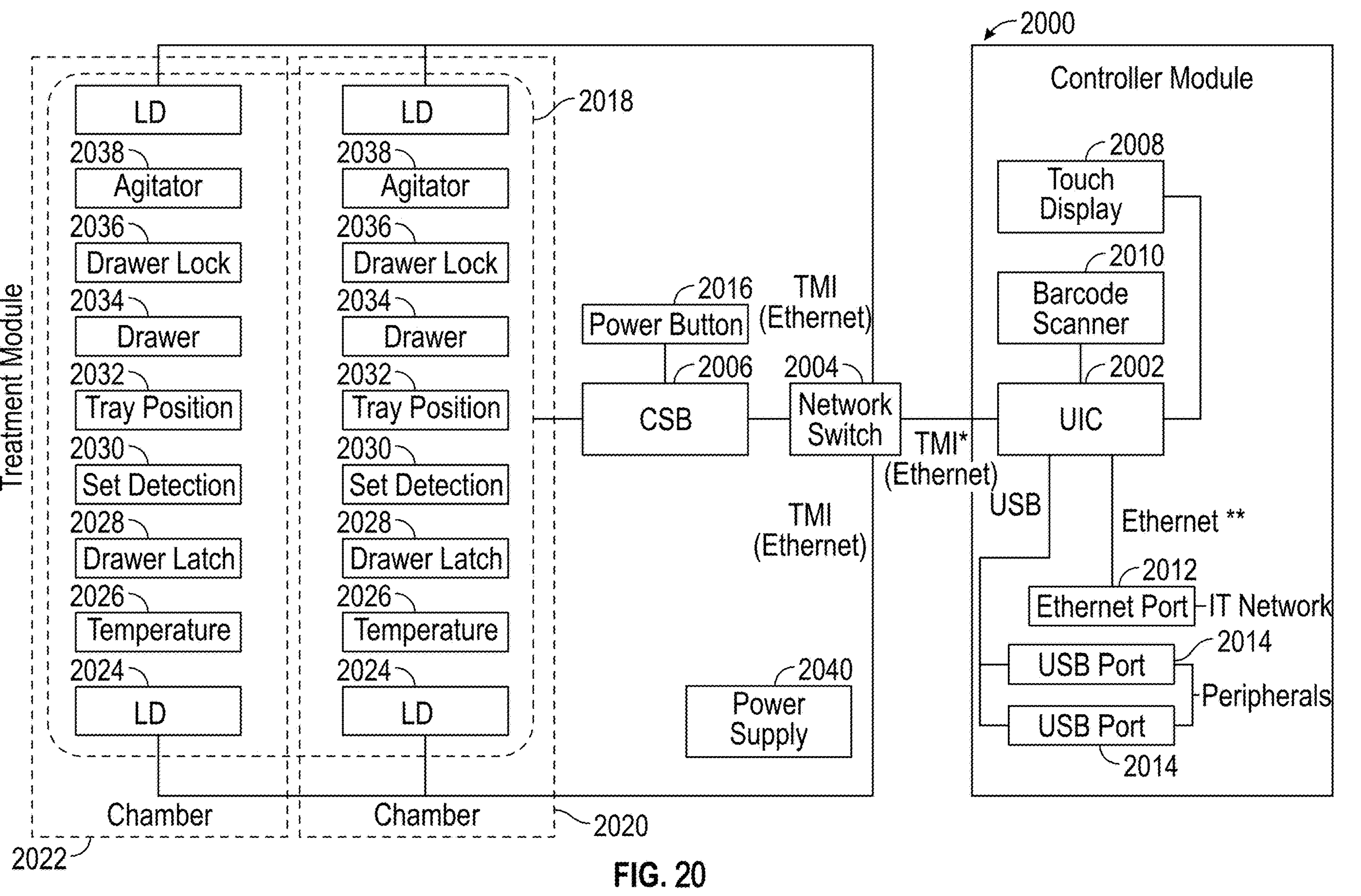
FIG. 20 illustrates another exemplary system diagram of a system for treating biological fluids according to examples of the disclosure.

FIG. 20 illustrates an exemplary system diagram of a system for treating biological fluids according to examples of the disclosure. The example system 2000 of FIG. 20 can serve as an additional example system diagram with respect the example provided above with respect to FIG. 19. In one or more examples, the system 2000 can include a user interface controller 2002 that can interface with one or more non-safety critical components of the device. In one or more examples the non-safety critical components can include a display (e.g., touch display) 2008, a scanner (e.g., barcode scanner) 2010, an Ethernet port 2012 and one or more USB ports 2014. The non-safety critical components can refer to components within the system 2000 that do not directly interact with the one or more biological fluids being treated by the device, and whose operation does not have a substantial effect on the safety and efficacy of the treatment process.

In one or more examples, the UIC 2002 can control and interact with one or more components of the system that are accessible by an external user of the device. For instance, in one or more examples, the UIC 2002 can interact with a touch display 2008 that can be configured to display one or more graphical user interfaces and is configured to receive one or more touch inputs from a user. In one or more examples, the UIC 2002 can control and interact with one or more barcode scanners 2010 that can be configured to scan one or more barcodes associated with a biological fluid (e.g., on a container associated with the biological fluid) and that can contain identifying information about the biological fluid. In one or more examples, the UIC 2002 can interact with an Ethernet port 2012 that can be configured to allow for the device to be connected to an external computing network (such as the internet or an enterprise computing system) so that the device can be controlled or accessed externally by a computer connected to the device via the Ethernet port 2012. In one or more examples the UIC 2002 can be configured to control and interact with one or more Universal Serial Bus (USB) ports 2014. The USB ports 2014 can allow for external devices such as a mouse or keyboard to be connected to the system 2000.

In one or more examples, the UIC 2002 can interact with one or more externally facing components (i.e., components that can be controlled by a user or device that is not part of the system) while not allowing the user or device to directly control one or more safety-critical components 2018 of the device. As will be described in detail below, the UIC 2002 can communicate with a control system board (CSB) 2006 that can be configured to receive commands from the UIC 2002 and convert those commands into one or more operations that are performed by one or more safety-critical components 2018.

In one or more examples of the disclosure, the system 2000 can include a network switch 2004 that can route transmissions between components of the system by using packet switching to receive and forward data to a particular component in the system. In one or more examples, the network switch 2004 can be configured to receive one or more packets (containing commands or information) from the UIC 2002 to the CSB 2006. For instance, the UIC 2002 can receive one or more inputs from an external user via the touch display 2008 and then can send those commands to the CSB 2006 via the network switch 2004 so that the CSB 2004 can control the safety-critical components of the device based on the user's inputs. In one or more examples, the network switch 2004 can also receive one or more packets from the CSB 2004 and can route the one or more packets to one or more safety-critical components 2018 (associated with a treatment module which can include both treatment chambers 2020 and 2022 so as to operate the safety-critical components for treatment of the biological fluids within the treatment chambers 2020 and 2022.

As briefly described above, each of the treatment chambers 2020 and 2022 can include one or more safety-critical components 2018. The safety-critical components 2018 can refer to the sensors and hardware used by the device to treat the one or more biological fluids. In one or more examples, the safety-critical components contained within each treatment chamber can include a modular light device module 2024, a temperature sensor 2026, a platform (e.g., drawer) latch sensor 2028, a set detection sensor 2030, a tray position sensor 2032, a platform (e.g., drawer) 2034, a platform (e.g., drawer) lock 2036, and an agitator 2038.

In one or more examples, the modular light device module 2024 can include one or more light sources (e.g., UV light sources) and light sensors and is configured to deliver light (e.g., UV light) to a biological fluid as well as monitor the amount of the light being delivered to and/or received by the biological fluid. In one or more examples of the disclosure, the safety-critical components 2018 can include an agitator that can be configured to agitate the contents of the treatment container to distribute (e.g., evenly distribute) the biological fluid and/or a pathogen inactivation compound in (e.g., in admixture with) the biological fluid. In one or more examples, agitator 2038 can include a mechanical agitator (e.g., motor, servo) configured to agitate a biological fluid or photoactive pathogen inactivation compound in (e.g., in admixture with) a biological fluid. In one or more examples, the safety critical components can include a platform (e.g., drawer) lock 2036 that is configured to lock or unlock the platform (e.g., drawer) of the treatment chamber (i.e., prevent the platform (e.g., drawer) from being opened) based on a command from the CSB 2006.

The safety-critical components 2018 can further include a plurality of sensors that are configured to provide the CSB 2006 with information regarding the operation of the device. In one or more examples, the temperature sensor 2026 can be configured to monitor the temperature of the system and/or the biological fluid and can be configured to transmit updates to the CSB 2006 indicating the temperature of the biological fluid and/or device. In one or more examples of the disclosure, the platform (e.g., drawer) latch sensor 2028 can be configured to detect whether a latch (e.g., lock) on the platform (e.g., drawer) of the device (described in detail above) is in an open or closed position, and can be configured to transmit a signal to the CSB 2006 indicating the position of the latch. In one or more examples, the set (e.g., processing set, fluid processing set) detector sensor 2030 can be configured to detect the presence of a container (e.g., bag) containing a biological fluid on or in a platform (e.g., drawer, associated tray) and/or within the treatment chamber and can be configured to transmit a signal to the CSB 2006 indicating the presence or lack thereof of the container (e.g., bag). In one or more examples of the disclosure, the tray position sensor 2032 can be configured to determine the presence of a tray and/or a position of a tray of the device (described in detail above), such as for example the presence of a tray and/or position (e.g., movement) of a tray within a platform (e.g., drawer), and can be configured to transmit a signal to CSB 2006 indicating the position of the platform/tray/drawer. In one or more examples, the platform (e.g., drawer) and/or associated sensor 2034 can be configured to determine a position of the platform (e.g., drawer) of the treatment chamber (e.g., determine if the platform (e.g., drawer) is in a closed position inside the treatment chamber) and can be configured to transmit a signal to CSB 2006 indicating the position of the drawer. In one or more examples, a "tray" can refer to a removable portion or component of a platform that houses the biological fluid during treatment, and which may be transparent (e.g., fully or partially transparent, so as to allow light to pass through it) on one or more surfaces, such as for example the floor (e.g., bottom) of the tray. In one or more examples, the term "drawer" can refer to the platform and associated frame that holds the tray, and that can secure an agitator motor. In one or more examples, the drawer can be configured to present the tray to the operator. In one or more examples, the tray can be agitated during treatment, such as for example by movement back and forth in a linear path within the platform (e.g., drawer).

In one or more examples of the disclosure, the CSB 2006 can be configured to communicate directly with a power button of the device so as to turn the device on or off, and subsequently issue commands to each of the safety-critical components 2018 to cease operation or begin operation. The system 2000 can also include a power supply 2040 that can be used to provide an electrical signal to each of the components in the system 2000 to power their operation.

As illustrated in FIG. 20, the system 2000 can include two separate controllers, UIC 2002 and CSB 2006, to control non-safety critical components and the safety critical components 2018 respectively. By including two separate controllers, the system 2000 can ensure that fraudulent or faulty operation of the device from external users or devices can minimally impact the operation of the safety-critical components 2018. To further isolate the safety-critical components, for the non-safety critical components, the UIC 2002 can be configured to communicated with the non-safety critical components in a first communications protocol, and the CSB 2006 can communicate with the safety critical components in a second communications protocol that is distinct from the first. In one or more examples, the system 2000 can further utilize a domain-specific communications protocol that is specific to the system to communicate with and command the safety-critical components 2018. In the example of FIG. 20, the domain-specific communications protocol can be referred to as a Treatment Module Interface (TMI) protocol.

In one or more examples, the TMI protocol can be configured such that the safety-critical components will only respond to commands sent from the CSB 2006. In this way, the UIC 2002 which is configured to control all of the externally facing components (i.e., components that can be accessed by an external user or device) cannot be used to directly control the safety-critical components 2018, thereby providing an added layer of security for the treatment process. Thus, in one or more examples, when a user enters an input into one of the non-safety critical components such as touch display 2008, and if the command requires action from one of the safety-critical components 2018, the command can be transmitted from the UIC 2002 to the CSB 2006 via the network switch 2004. In one or more examples, the network switch 2004 may be optional and not required. Once the CSB 2006 receives the desired action from the UIC 2002, it can generate one or more commands for the safety-critical component 2018 using the TMI protocol to operate those components according to the desired action registered by the UIC 2002.

In order to facilitate the above described interactions the TMI protocol, in one or more examples, can be configured to identify the sender/originator of any packets such that the receiver of a packet can determine whether the command issued from the CSB 2006. In one or more examples of the disclosure, the TMI protocol can be configured to only allow for commands originating from the CSB 2006 to act upon any the safety-critical components 2018. Thus, any component deemed safety-critical can be configured to only accept TMI packets from the CSB 2006 only.

In one or more examples, the TMI protocol can be configured as a custom communications interface that can serves as a message and command transport between the CSB 2006 and the components of the treatment module. The TMI can be configured to support safety and cyber-security (as described above) by separating non-safety and safety-critical functionality. In addition to supporting safety, the TMI protocol can further be configured to enable modularity of and scalability of the device, and also improve the reliability and testability of the device. In one or more examples, the TMI protocol can utilize a Ethernet, UDP/IP transport medium to relay communications that are written in the protocol.

Figure 21:
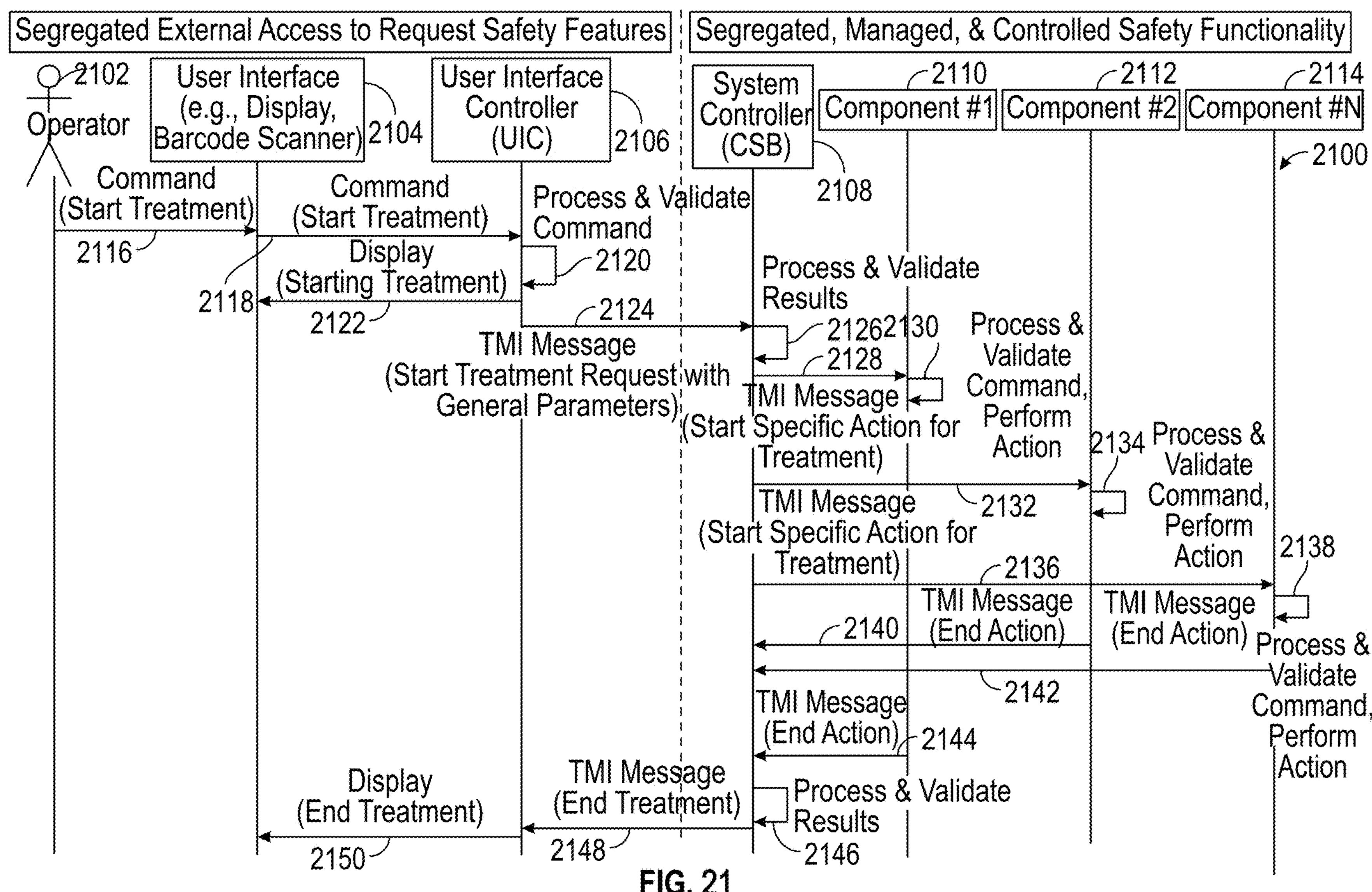
FIG. 21 illustrates an exemplary implementation of a domain-specific communications protocol according to examples of the disclosure.

FIG. 21 illustrates an exemplary implementation of a domain-specific communications protocol according to examples of the disclosure. The example diagram 2100 of FIG. 21 illustrates the process by which a command issued by an external user is translated to one or more commands that are used to operate the individual components of an electronic device for treating a biological fluid.

In one or more examples, the process shown in diagram 2100 can begin with a user 2102 who issues a command to the device to start treatment of a biological fluid. In one or more examples, the user 2102 can issue the command 2116 via a user interface 2104. The user interface 2104 can include a display (e.g., touch screen display), a voice recognition component, a motion detection component, keyboard, or any other device that can be configured to allow for the user to input its desired actions to the electronic device so that the device may act on those commands.

In one or more examples, once the user interface 2104 receives the command 2116 from the user 2102, the user interface 2104 can convert the user's command into a command 2118 that is specifically formatted to be compatible with a user interface controller (UIC) 2106 (described in detail above). The UIC 2106, upon receiving the command 2118, can process and validate the command as shown at 2120. If the command 2118 received by the UIC is successfully validated (i.e., the command is proper and in one or more examples is authenticated), then the UIC 2106 can transmit a signal 2122 to the user interface 2104, so that the user interface 2104 can provide a display to the user 2102 via the interface 2104 that the treatment was successfully initiated.

In one or more examples, after processing and validating the received command 2118, the UIC 2106 can generate and transmit a command 2124 formatted using the domain-specific TMI communications protocol that is configured to alert the system controller 2108 (described above with respect to FIG. 20) to the user's desired operation of the electronic device. In one or more examples, the command 2124 formatted in the TMI protocol can include information regarding the sender of the command 2124 (in this case the UIC 2106), and the system controller can be configured to accept only commands to initiate treatment sent by UIC 2106. When the system controller 2108 receives the TMI formatted message 2124 from the UIC 2106, the system controller 2108 can process and validate the command as indicated at 2126.

In one or more examples, once the system controller 2108 process and validates the TMI formatted message 2124 from the UIC 2106 at 2126, the system controller can generate and transmit one or more commands to each of the components 2110, 2112, and 2114 to initiate the treatment process on a biological fluid. In one or more examples, components 2110, 2112, and 2114 can represent the safety-critical components located in the treatment chambers of a device, which in one or more examples can include the light device components, agitators, platform/tray/drawer locks, and sensors discussed in detail above with respect to FIG. 12. In one or more examples, the system controller can generate separate commands 2128, 2132, and 2136 to each of the components 2110, 2112, and 2114 that may be involved in the treatment of the biological fluid. In one or more examples, the commands 2128, 2132, and 2136 can be formatted using the domain-specific TMI communications protocol that is only known to the components within the electronic device. Furthermore, the commands 2128, 2132, and 2136 generated using the TMI communications protocol can include information regarding the origination of the command (in this case the system controller 2108), and each of the components 2110, 2112, and 2114 can be configured to only respond to the commands that are determined to originate from the system controller 2108.

In one or more examples, the system controller 2108 can generate a TMI message 2128 to a first component of the treatment chamber 2110 indicating the action that the component is to take and identifying the origination of the message. Once the first component 2110 receives the command 2128, it can process and validate the command at 2130 to ensure that not only is the command proper, but also that it originated from the system controller 2108. In the event that the component 2110 determines that the command 2128 is improper or that it is unable to determine that the command 2128 originated from the system controller 2108, the component can transmit a message to the system controller 2108 alerting it to the error (not shown). However, if the command is properly validated and authenticated, then in one or more examples, the component 2110 can perform the action indicated by the message 2128. Once the component 2110 performs the action, it can then generate a message 2144 that is also formatted using the TMI protocol that lets the system controller 2108 that the requested action has been performed.

In one or more examples, the system controller 2108 can generate a TMI message 2132 to a second component of the treatment chamber 2112 indicating the action that the component is to take and identifying the origination of the message. Once the second component 2112 receives the command 2132, it can process and validate the command at 2134 to ensure that not only is the command proper, but also that it originated from the system controller 2108. In the event that the component 2112 determines that the command 2132 is improper or that it unable to determine that the command 2132 originated from the system controller 2108, the component 2112 can transmit a message to the system controller 2108 alerting it to the error (not shown). However, if the command is properly validated and authenticated, then in one or more examples the component 2112 can perform the action indicated by the message 2132. Once the component 2112 performs the action, it can then generate a message 2140 that is also formatted using the TMI protocol that lets the system controller 2108 that the requested action has been performed.

In one or more examples, the system controller 2108 can generate a TMI message 2136 to a third component 2114 of the treatment chamber indicating the action that the component is to take and identifying the origination of the message. Once the third component 2114 receives the command 2136, it can process and validate the command at 2138 to ensure that not only is the command proper, but also that it originated from the system controller 2108. In the event that the component 2114 determines that the command 2136 is improper or that it unable to determine that the command 2136 originated from the system controller 2108, the component 2114 can transmit a message to the system controller 2108 alerting it to the error (not shown). However, if the command is properly validated and authenticated, then in one or more examples the component 2114 can perform the action indicated by the message 2136. Once the component 2114 performs the action, it can then generate a message 2142 that is also formatted using the TMI protocol that lets the system controller 2108 that the requested action has been performed.

While the examples of FIG. 21 illustrates a communications process for a device that includes three components 2110, 2112, 2114, the example can be readily applied to a device with any number of components without deviating from the methods and process described above with respect to FIG. 21. Thus, the components 2110, 2112, and 2114 are meant for illustrative purposes and should not be seen as limiting.

In one or more examples, once the system controller 2108 has received messages 2140, 2142, and 2144, from components 2110, 2112, and 2114, the system controller 2108 can process and validate the received messages at 2146, and can then generate and transmit a TMI formatted message 2148 to the UIC 2106 indicating that the treatment has ended (e.g., treatment has been completed). In one or more examples, upon receiving the message 2148 from the system controller 2108 indicating that the treatment has ended, the UIC can transmit a message 2150 (either in the TMI format or in another format understood by the display) to the user interface 2104, instructing the user interface to display one or more graphical user interface that indicate to the user that the treatment process has finished.

As demonstrated above with respect to the example of FIG. 21, the device can be configured to provide isolation between the components controlled by UIC 2106 and the components controlled system controller 2108 using the domain-specific TMI communications protocol. By configuring the TMI protocol such that the safety-critical components used to treat a biological fluid can only accept commands generated in the TMI protocol (which is only known internally by the device) and only accept commands generated by the system controller 2108, the chance that a malicious user or other external actor commanding the device without authorization is minimized. In one or more examples, the TMI communications protocol can further be configured to facilitate the introduction of new or replacement components in the treatment chambers, with minimal disruption to the device, as the system controller can be configured to detect new components and ensure that only it can issue commands to operate them.

In one or more examples, the TMI communications protocol can serve as a message and command transport between the controller 2108 and the components located within each treatment chamber. The TMI communications protocol can support safety and cyber security needs of the device by separating and isolating the safety-critical components from the non-safety critical components, enable modularity and scalability, and improve reliability and testability. In one or more examples, the TMI communications protocol can be configured using a state-based design that can reduce design complexity, reduce change for misuse, isolate errors amongst components, and report events in an efficient manner to the device. In one or more examples, the TMI communications protocol can utilize a commercial off the shelf transport protocol such and Ethernet or UDP/IP to transport the messages back and forth between the various components of the device.

Figure 22:
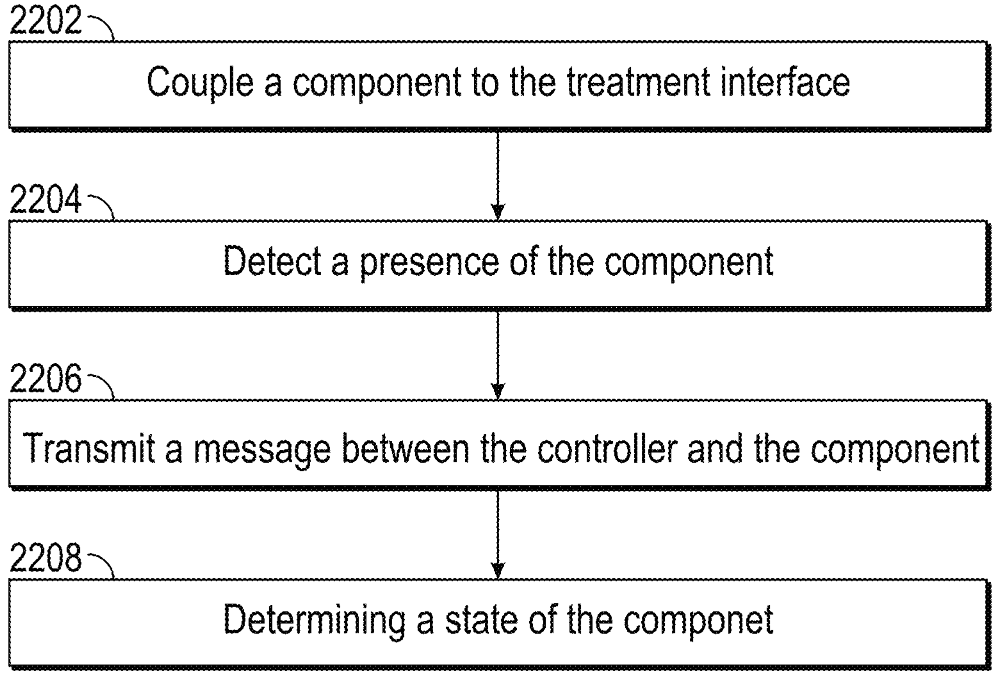
FIG. 22 illustrates an exemplary method of operating an exemplary system for treating biological fluids according to examples of the disclosure.

FIG. 22 illustrates an exemplary method 2200 of operating an exemplary system for treating biological fluids according to examples of the disclosure. In some examples, the method 2200 can be performed with the devices or systems disclosed herein.

The method 2200 includes coupling (step 2202) a non-safety critical component or a safety-critical component to the treatment interface. For example, with references to FIGS. 18 and 19, one of a non-safety critical component or a safety critical component is communicatively coupled to the common interface 1822 or 1822.

The method includes: in response to the coupling of the non-safety critical component or the safety-critical component to the treatment interface, detecting (step 2204), with the controller, a presence of the non-safety critical component or the safety-critical component in the electronic device. For example, with references to FIGS. 18 and 19, the presence of the non-safety critical component or safety critical component is a detected in response to the coupling performed in step 2202.

The method includes transmitting (step 2206) a message between the controller and the non-safety critical component or the safety-critical component through the treatment interface, the message based on a domain-specific interface language. For example, with references to FIGS. 18 and 19, a message, as disclosed herein, between the coupled component and the controller module is being transmitted.

The method includes determining (step 2208) a state of the non-safety critical component or the safety-critical component based on the message. For example, with references to FIGS. 18 and 19, a state, as disclosed herein, of the coupled component is determined based on the transmitted message in step 2206.

Although the common interface is described with respect to a system that includes a plurality of non-safety critical components and safety critical components, it is understood that the above description is also applicable to individual non-safety critical component or an individual safety critical component. For example, the system includes a control module, a non-safety critical component, a safety critical component, and a common interface (e.g., a treatment interface of an electronic device for treating a biological fluid). The interaction between the control module and the non-safety critical component or the safety critical component using the common interface can be substantially similar to the common interface interactions between the control module, the non-safety critical components, and the safety critical components described herein. For the sake of brevity, the interactions between the control module and the non-safety critical component or the safety critical component are not described. It is understood that these interactions are also include within the scope of the disclosure.

Figure 23:
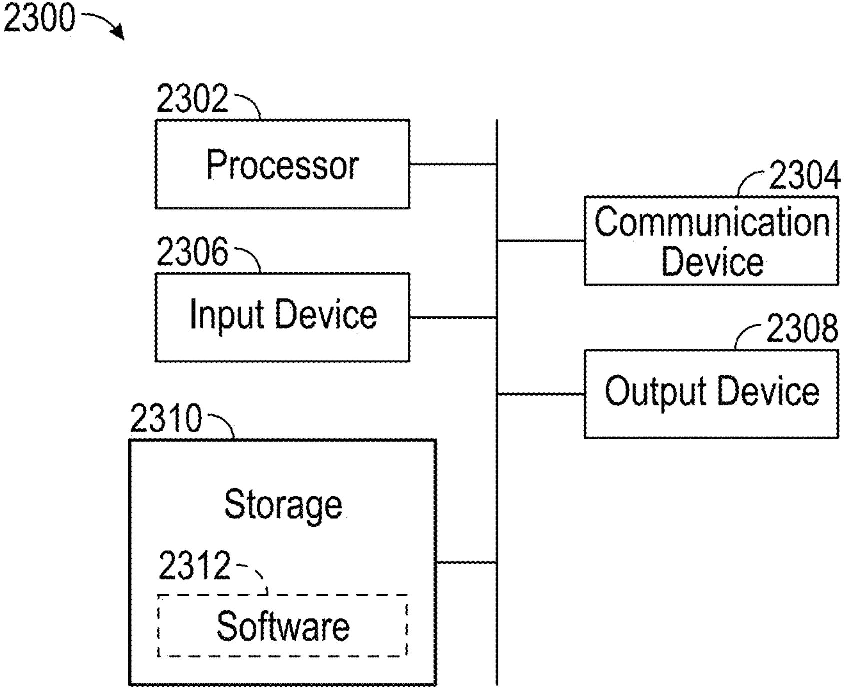
FIG. 23 illustrates an example of a computing device according to examples of the disclosure.

FIG. 23 illustrates an example of a computing device in accordance with one embodiment. Device 2300 can be a host computer connected to a network. Device 2300 can be a client computer or a server. As shown in FIG. 23, device 2300 can be any suitable type of microprocessor-based device, such as a personal computer, work station, server, or handheld computing device (portable electronic device) such as a phone or tablet. The device can include, for example, one or more of processors 2302, input device 2306, output device 2308, storage 2310, and communication device 2304. Input device 2306 and output device 2308 can generally correspond to those described above and can either be connectable or integrated with the computer.

Input device 2306 can be any suitable device that provides input, such as a touchscreen, keyboard or keypad, mouse, or voice-recognition device. Output device 2308 can be any suitable device that provides output, such as a touchscreen, haptics device, or speaker.

Storage 2310 can be any suitable device that provides storage, such as an electrical, magnetic, or optical memory including a RAM, cache, hard drive, or removable storage disk. Communication device 2304 can include any suitable device capable of transmitting and receiving signals over a network, such as a network interface chip or device. The components of the computer can be connected in any suitable manner, such as via a physical bus, or wirelessly.

Software 2312, which can be stored in storage 2310 and executed by processor 2310, can include, for example, the programming that embodies the functionality of the present disclosure (e.g., as embodied in the devices described above).

Software 2312 can also be stored and/or transported within any non-transitory, computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 2310, that can contain or store programming for use by or in connection with an instruction-execution system, apparatus, or device.

Software 2312 can also be propagated within any transport medium for use by or in connection with an instruction-execution system, apparatus, or device, such as those described above, that can fetch instructions associated with the software from the instruction-execution system, apparatus, or device and execute the instructions. In the context of this disclosure, a transport medium can be any medium that can communicate, propagate, or transport programming for use by or in connection with an instruction-execution system, apparatus, or device. The transport readable medium can include, but is not limited to, an electronic, magnetic, optical, electromagnetic, or infrared wired or wireless propagation medium.

Device 2300 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 2300 can implement any operating system suitable for operating on the network. Software 2312 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

In one aspect, an electronic device for treating a biological fluid, includes: a plurality of non-safety critical components; a first controller communicatively coupled to the plurality of non-safety critical components and configured to operate the plurality of non-safety critical components; a plurality of safety critical components, wherein the safety critical components comprise: one or more platforms, wherein each platform of the one or more platforms is configured to carry one or more biological fluids; one or more modular light devices, wherein each light device is configured to illuminate the biological fluid; and one or more safety components; wherein the one or more safety components are configured to monitor the operation of the safety critical components; and a second controller communicatively coupled to the plurality of safety critical components and communicatively coupled to the first controller, wherein the second controller is configured to coordinate one or more operations involving the plurality of safety critical components; wherein the first controller and the second controller communicate with one another using a domain-specific interface language configured to isolate the plurality of non-safety critical components from the plurality of safety-critical components.

While specific components, configurations, features, and functions are provided above, it will be appreciated by one of ordinary skill in the art that other variations may be used. Additionally, although a feature may appear to be described in connection with a particular embodiment, one skilled in the art would recognize that various features of the described embodiments may be combined. Moreover, aspects described in connection with an embodiment may stand alone.

In some embodiments, any of the above described treatment systems and devices may be used to inactivate pathogen(s) in one or more biological fluids, including for example, biological fluids admixed with one or more pathogen inactivation compounds (e.g., photoactive pathogen inactivation compound, psoralen). In particular, any of the above described treatment systems and devices may illuminate a mixture of one or more pathogen inactivation compounds and a biological fluid, such as for example blood or a blood product (e.g., platelet compositions, plasma compositions and their derivatives), with light of certain wavelengths (e.g., ultraviolet light) to cause a photochemical reaction and inactivate pathogen(s), such as viruses, bacteria, parasites and other contaminants, such as for example, cell contaminants (e.g., leukocytes) that may be present in the biological fluid. In some embodiments, the pathogen inactivation compound targets nucleic acids to photochemically form adducts and/or cross-links. For example, a device of the present disclosure may be used in a method of treating a biological fluid comprising: providing a biological fluid in admixture with a photoactive pathogen inactivation compound (e.g., psoralen, amotosalen), and illuminating the biological fluid with ultraviolet light, such as for example, ultraviolet light with a first peak wavelength of from about 315 nm to about 350 nm (e.g., about 315 nm to about 335 nm, about 330 nm to about 350 nm, about 340 nm to about 350 nm, about 340 nm, about 345 nm) emitted by a set of one or more first light sources, wherein illuminating the biological fluid occurs for a duration and at an intensity sufficient to inactivate a pathogen in the biological fluid. In some examples, a device of the present disclosure may be used in a method of treating a biological fluid comprising: illuminating the biological fluid with ultraviolet light (e.g., UV-A, UV-B, UV-C) emitted by a set of one or more first light sources, wherein illuminating the biological fluid occurs for a duration and at an intensity sufficient to inactivate a pathogen in the biological fluid. In some embodiments, each of the one or more first light sources emits light having a full-width half-maximum (FWHM) spectral bandwidth of less than 20 nanometers. In some embodiments, each of the one or more first light sources is a light-emitting diode (LED).

The term "pathogen inactivation compound" means any suitable compound, such as a small organic compound, that can be used to inactivate a pathogen that may be present in a biological fluid, such as for example, blood or a blood product. A pathogen inactivation compound that is a "photoactive" or "photoactivated" or "photochemical" or "photosensitizer" compound is a suitable compound that requires some level of light in order to sufficiently inactivate a pathogen. Such compounds are preferred in the inactivation of pathogens in biological products as they provide control over the inactivation process. In some embodiments, the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540. In some embodiments, the pathogen inactivation compound is a psoralen. In some embodiments, the pathogen inactivation compound is amotosalen (e.g., S-59). Such photoactivated or photochemical pathogen inactivation compounds as described herein may include, but are not limited to, psoralens, isoalloxazines, alloxazines, phthalocyanines, phenothiazines, and porphyrins, where these terms are understood to encompass a general class of compounds, i.e. the core compound and suitable derivatives thereof. For example psoralens or a psoralen generally describes the psoralen core compound and any derivative thereof (e.g. amotosalen), isoalloxazines or an isoalloxazine generally describes the isoalloxazine core and any derivative thereof (e.g. riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 4'-(4-amino-2-oxa)butyl-4,5',8-trimethyl psoralen. Where the methods of the present disclosure include adding amotosalen HCl (the HCl salt of amotosalen), the removal of this compound from the biological fluid, such as for example a blood product (e.g., platelet composition, unit of platelets, plasma composition, whole blood composition, plasma composition) is not limited to the removal of amotosalen HCl, as the amotosalen can be present in solution as other salts or as the free base. As used in the methods described herein, removal of amotosalen means removal of the compound in any form, e.g. as the free base or as any salt, as measured by the assays described herein.

In some embodiments, the pathogen inactivation compound is a 4-primaryamino-substituted psoralen, which is a psoralen compound having an $NH_2$ group linked to the 4'-position of the psoralen by a hydrocarbon chain having a total length of 2 to 20 carbons, where 0 to 6 of those carbons are independently replaced by NH or O, and each point of replacement is separated from each other point of replacement by at least two carbons, and is separated from the psoralen by at least one carbon. 4'-primaryamino-substituted psoralens may have additional substitutions on the 4, 5', and 8 positions of the psoralen, said substitutions include, but are not limited to, the following groups: H and $(CH_2)_nCH_3$, where n=0-6. In some embodiments, the 4'-primaryamino-substituted psoralen comprises: a) a substituent $R_1$ on the 4' carbon atom, selected from the group comprising: $—(CH_2)_u—NH_2$, $—(CH_2)_w—R_2—(CH_2)_z—NH_2$, $—(CH_2)_w—R_2—(CH_2)_x—R_3—(CH_2)_z—NH_2$, and $—(CH_2)_w—R_2—(CH_2)_x—R_3—(CH_2)_y—R_4—(CH_2)_z—NH_2$; wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4, 5', and 8 carbon atoms respectively, independently selected from the group comprising H and $(CH_2)_vCH_3$, where v is a whole number from 0 to 5; or a salt thereof.

In some embodiments, the pathogen inactivation compound is a 5-primaryamino-substituted psoralen, which is a psoralen compound having an $NH_2$ group linked to the 5'-position of the psoralen by a hydrocarbon chain having a total length of 1 to 20 carbons, where 0 to 6 of those carbons are independently replaced by NH or O, and each point of replacement is separated from each other point of replacement by at least two carbons, and is separated from the psoralen by at least one carbon. 5'-primaryamino-substituted psoralens may have additional substitutions on the 4, 4', and 8 positions of the psoralen, said substitutions include, but are not limited to, the following groups: H and $(CH_2)_nCH_3$, where n=0-6. In some embodiments, the 5'-primaryamino-substituted psoralen comprises: a) a substituent $R_1$ on the 5' carbon atom, selected from the group comprising: $—(CH_2)_u—NH_2$, $—(CH_2)_w—R_2—(CH_2)_z—NH_2$, $—(CH_2)_w—R_2—(CH_2)_x—R_3—(CH_2)_z—NH_2$, and $—(CH_2)_w—R_2—(CH_2)_x—R_3—(CH_2)_y—R_4—(CH_2)_z—NH_2$; wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5, where when $R_1$ is selected from the group comprising $—(CH_2)_u—NH_2$, $R_7$ is $(CH_2)_vCH_3$, and where when $R_5$, $R_6$, and $R_7$ are $(CH^2)_vCH_3$, u is a whole number from 3 to 10; or a salt thereof. Exemplary psoralen compounds are described, e.g., in U.S. Pat. No. 5,593,823.

In some embodiments, the biological fluid is in admixture with a pathogen inactivation compound (PIC) in a platelet additive solution (PAS). In some embodiments, the PIC is admixed with the PAS prior to admixing with the biological fluid. Platelet additive solutions are known in the art, for example, as described by Alhumaidan et al. and Ringwald et al. (Alhumaidan, H. and Sweeney, J., *J Clin Apheresis,* 27: 93-98 (2012); Ringwald et al., *Transfusion Medicine Reviews,* 20: 158-64 (2006)), which are hereby incorporated by reference in their entirety. In some embodiments, the platelet additive solution (PAS) comprises one or more of chloride, acetate, citrate, potassium, magnesium, phosphate, gluconate, glucose, and bicarbonate. In some embodiments, the platelet additive solution (PAS) is a PAS approved by a regulatory agency or accrediting organization generally accepted in the field.

In some embodiments, the methods further comprise agitating the biological fluid. In some embodiments of any of the methods of the disclosure, a total dose of ultraviolet light illuminating the biological fluid (e.g., emitted by the one or more light sources, emitted by a set of one or more light sources, emitted by an array of light sources) is about 0.5 J/cm$^2$ to about 50 J/cm$^2$, such as any of about 0.5 J/cm$^2$ to about 10 J/cm$^2$, about 0.5 J/cm$^2$ to about 15 J/cm$^2$, about 0.5 J/cm$^2$ to about 25 J/cm$^2$, about 1 J/cm$^2$ to about 10 J/cm$^2$, about 1 J/cm$^2$ to about 15 J/cm$^2$, about 1 J/cm$^2$ to about 25 J/cm$^2$, about 3 J/cm$^2$ to about 10 J/cm$^2$, about 3 J/cm$^2$ to about 15 J/cm$^2$, about 3 J/cm$^2$ to about 25 J/cm$^2$, about 5 J/cm$^2$ to about 10 J/cm$^2$, about 5 J/cm$^2$ to about 15 J/cm$^2$, about 5 J/cm$^2$ to about 25 J/cm$^2$, about 10 J/cm$^2$ to about 30 J/cm$^2$, about 10 J/cm$^2$ to about 20 J/cm$^2$, about 15 J/cm$^2$ to about 50 J/cm$^2$, about 15 J/cm$^2$ to about 35 J/cm$^2$, about 20 J/cm$^2$ to about 30 J/cm$^2$, about 25 J/cm$^2$ to about 50 J/cm$^2$, about 30 J/cm$^2$ to about 40 J/cm$^2$, or about 40 J/cm$^2$ to about 50 J/cm$^2$. In some embodiments, the total dose of ultraviolet light illuminating the biological fluid is about 0.5 J/cm$^2$ or more, such as about any of 1 J/cm$^2$ or more, 2 J/cm$^2$ or more, 3 J/cm$^2$ or more, 4 J/cm$^2$ or more, 5 J/cm$^2$ or more, 6 J/cm$^2$ or more, 7 J/cm$^2$ or more, 8 J/cm$^2$ or more, 9 J/cm$^2$ or more, 10 J/cm$^2$ or more, 15 J/cm$^2$ or more, 20 J/cm$^2$ or more, 25 J/cm$^2$ or more, 30 J/cm$^2$ or more, 35 J/cm$^2$ or more, 40 J/cm$^2$ or more, 45 J/cm$^2$ or more, or 50 J/cm$^2$ or more. In some embodiments, the total dose of ultraviolet light illuminating the biological fluid is less than about 50 J/cm$^2$, less than about 40 J/cm$^2$, less than about 30 J/cm$^2$, less than about 25 J/cm$^2$, less than about 20 J/cm$^2$, less than about 15 J/cm$^2$, or less than about 10 J/cm$^2$. In some embodiments, illuminating the biological fluid occurs for a duration and at an intensity sufficient to inactivate a pathogen in the biological fluid (e.g., if present in the biological fluid). For example, in some embodiments, illuminating the biological fluid occurs for a duration and at an intensity sufficient to provide a total dose (e.g., desired total dose, pre-determined total dose, aforementioned total dose) of ultraviolet light illuminating the biological fluid (e.g., any suitable combination of duration and intensity sufficient to provide the total dose of ultraviolet light). In some embodiments, the intensity is between 1 and 1000 mW/cm$^2$ (e.g., between 1 and 100 mW/cm$^2$). In some embodiments, the duration is between 1 second and 2 hours (e.g., between 1 minute and 60 minutes).

It should be understood that treatment of a biological fluid to inactivate pathogen(s) that may be present does not necessarily inactivate completely all pathogens that may be present, but substantially reduces the amount of pathogens to significantly reduce the risk arising from the presence of a pathogen (e.g., infection associated with administration of a biological fluid contaminated with a pathogen, transfusion associated disease from a blood product, transfusion transmitted infection from a blood product). The inactivation of a pathogen may be assayed by measuring the number of infective pathogens (e.g., viral particles, bacteria) in a certain volume, and the level of inactivation is typically represented in the log reduction in the infectivity of the pathogen, or log reduction in titer. Methods of assaying log reduction in titer, and measurements thereof to assess levels of pathogen inactivation are well known in the art. In some embodiments, the systems, devices and/or methods for treating are sufficient to inactivate at least 1 log (e.g., at least 2 logs, at least 3 logs, at least 4 logs, or more) of a pathogen in the biological fluid when present. In some embodiments, the biological fluid after illuminating is suitable for infusion into a subject without further processing to remove residual pathogen inactivation compound or photoproduct(s) thereof. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 10 μM or less of a pathogen inactivation compound after illuminating the biological fluid. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 7.5 μM or less of the pathogen inactivation compound after illuminating. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 5 μM or less (e.g., 4 μM or less, 3 μM or less, 2 μM or less, 1 μM or less, 0.5 μM or less) of the pathogen inactivation compound after illuminating. In some embodiments, a concentration of the pathogen inactivation compound in admixture with the biological fluid prior to illuminating is at least about 10 μM (e.g., at least about 30 μM, at least about 60 μM, at least at least about 90 μM, at least about 110 μM). In some embodiments, a concentration of the pathogen inactivation compound in admixture with the biological fluid prior to illuminating is about 15 μM to about 150 μM (e.g., about 30 μM to about 110 μM, about 60 μM to about 90 μM, about 75 μM). In some embodiments, a concentration of the pathogen inactivation compound in admixture with the biological fluid after illuminating is at least 3-fold less than the concentration of pathogen inactivation compound in admixture with the biological fluid prior to illuminating. In some embodiments, the biological fluid after illuminating maintains sufficient biological activity so that the biological fluid is suitable for infusion into a subject. In any of the aforementioned embodiments, the biological fluid may be a blood product (e.g., platelets, plasma).

In some aspects of the above device, the first controller includes an output port, and wherein the first controller is configured to communicate with an external computing device using the output port.

In some aspects of the above devices, isolating the plurality of non-safety critical components from the plurality of safety-critical components includes configuring the domain-specific interface language so as to minimize an impact to the plurality of safety critical components from one or more modifications to the non-safety critical components.

In some aspects of the above devices, the device further includes one or more treatment chambers configured to receive the biological fluid, and wherein each platform of the one or more platforms are configured to be positioned in a treatment chamber of the one of the one or more treatment chambers.

In some aspects of the above devices, the safety critical components further comprise one or more agitators, wherein each agitator is configured to agitate at least one of the one or more platforms.

In some aspects of the above devices, the safety critical components further comprise one or more sensors configured to detect light energy from the one or more light devices.

In some aspects of the above devices, the one or more modular light devices includes one or more arrays of light sources positioned to illuminate the biological fluid and wherein the one or more arrays of light sources are configured to emit light in an ultraviolet light spectrum.

In some aspects of the above devices, the one or more arrays of light sources comprise a plurality of light sources, wherein each light source of the plurality of light sources emits light having a full-width half-maximum (FWHM) spectral bandwidth of less than 20 nanometers.

In some aspects of the above devices, the one or more arrays of light sources comprise a plurality of light sources, wherein each light source of the plurality of light sources is a light-emitting diode (LED).

In some aspects of the above devices, the one or more arrays of light sources each comprises a respective first light source channel configured to emit ultraviolet light with a first peak wavelength of the array.

In some aspects of the above devices, the one or more arrays of light sources each comprise a first light source channel configured to emit ultraviolet light with a first peak wavelength from about 315 nm to about 350 nm.

In some aspects of the above devices, the first light source channel comprises one or more light sources each of which emits light having a full-width half-maximum (FWHM) spectral bandwidth of less than 20 nanometers.

In some aspects of the above devices, the first light source channel comprises one or more light sources, and wherein the one or more light sources are light emitting diodes (LEDs).

In some aspects of the above devices, the one or more light devices further comprise one or more sensors configured to detect light energy from the one or more arrays of light sources.

In some aspects of the above devices, the one or more safety critical components includes computing hardware configured to perform one or more algorithms and configured to store information regarding the operation of the electronic device.

In some aspects of the above devices, the second controller is configured to turn one or more of the safety critical components on or off based on one or more operating conditions of the device.

In some aspects of the above devices, the one or more safety components are collectively configured to implement a hardware watchdog.

In some aspects of the above devices, the one or more safety components are collectively configured to implement a software watchdog.

In some aspects of the above devices, the one or more non-safety critical components includes a display configured to provide information to a user of the device and/or receive an input from the user of the device.

In some aspects of the above devices, for use in a method of treating a biological fluid including: providing a biological fluid in admixture with a photoactive pathogen inactivation compound, and illuminating the biological fluid with ultraviolet light with a first peak wavelength of from about 315 nm to about 350 nm emitted by a set of one or more first light sources, wherein: 1) each of the one or more first light sources emits light having a full-width half-maximum (FWHM) spectral bandwidth of less than 20 nanometers, or 2) each of the one or more first light sources is a light-emitting diode (LED), and wherein illuminating the biological fluid occurs for a duration and at an intensity sufficient to inactivate a pathogen in the biological fluid.

In some aspects of the above devices, the device further includes: a treatment interface, wherein the first controller is communicatively coupled to the plurality of non-safety critical components and the second controller is communicatively coupled to the plurality of safety critical components through the treatment interface; one or more processors; memory; and one or more programs, wherein the one or more programs are stored in the memory and configured to be executed by the one or more processors, the one or more programs including instructions for: in response to communicatively coupling the plurality of non-safety critical components to the treatment interface and communicatively coupling the plurality of safety-critical component to the treatment interface, detecting, with the controller, presences of the plurality of non-safety critical component and the plurality of safety-critical component in the electronic device; transmitting first messages between the first controller and the non-safety critical component through the treatment interface; transmitting second messages between the second controller and the safety-critical component through the treatment interface, wherein the first and second messages are based on the domain-specific interface language; determining states of the non-safety critical components based on the first messages; and determining states of the safety critical components based on the second messages.

In some aspects of the above devices, a non-safety critical component or a safety-critical component is in a first state, and the one or more programs further includes instructions for: changing the state of the non-safety critical component or the safety-critical component from the first state to a second state; in response to the changing the state, sending, from of the non-safety critical component or the safety-critical component to the first controller or the second controller through the treatment interface, a second message; receiving, at the first controller or the second controller, the second message; and in response to receiving the second message, determining a second state of the treatment component.

In some aspects of the above devices, the one or more programs further includes instructions for providing power to the electronic device; and the presences of the plurality of non-safety critical component and the plurality of safety-critical component are detected further in response to the providing of power to the electronic device.

In some aspects of the above devices, the one or more programs further includes instructions for: in response to the providing of power to the electronic device, assigning local network addresses and ports to the plurality of non-safety critical components and the plurality of safety-critical components, wherein the local network addresses or ports are based on the domain-specific device interface language.

In some aspects of the above devices, the one or more messages written in the domain-specific interface language can be transmitted using TCP/IP.

In another aspect, a method of treating a biological fluid includes: providing a biological fluid in admixture with a photoactive pathogen inactivation compound, and illuminating the biological fluid with any of the above devices, for a duration and at an intensity sufficient to inactivate a pathogen in the biological fluid.

In another aspect, a method of operating an electronic device for treating a biological fluid, the electronic device including a controller, a non-safety critical component, a safety-critical component, and a treatment interface, the method includes: coupling the non-safety critical component or the safety-critical component to the treatment interface; in response to the coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component through the treatment interface, the message based on a domain-specific interface language; and determining a state of the non-safety critical component or the safety-critical component based on the message.

In some aspects of the above method, the electronic device further comprises a second controller coupled to the treatment interface and the safety-critical component is coupled to the treatment interface, the method further includes: coupling the non-safety critical component to the treatment interface; and isolating the non-safety critical component from the safety-critical component, wherein the isolation comprises configuring the domain-specific interface language so as to minimize an impact to the safety-critical component from one or more modifications to the non-safety critical component.

In some aspects of the above methods, the non-safety critical component or the safety-critical component is in a first state, the method further includes: changing the state of the non-safety critical component or the safety-critical component from the first state to a second state; in response to the changing the state, sending, from of the non-safety critical component or the safety-critical component to the controller through the treatment interface, a second message; receiving, at the controller, the second message; and in response to receiving the second message, determining a second state of the treatment component.

In some aspects of the above methods, the safety-critical component is one of a platform, light device, agitator, and a safety component, wherein the one or more safety components are configured to monitor the operation of the safety-critical components.

In some aspects of the above methods, the method further includes isolating the treatment interface from an external network using the domain-specific interface language.

In some aspects of the above methods, the method further includes providing power to the electronic device; the presence of the treatment component is detected further in response to the providing of power to the electronic device.

In some aspects of the above methods, the method further includes in response to the providing of power to the electronic device, assigning a local network address or a port to the non-safety critical component or the safety-critical component, wherein the local network address or port is based on the domain-specific interface language.

In some aspects of the above methods, one or more messages written in the domain-specific interface language can be transmitted using TCP/IP.

In another aspect, an electronic device for treating a biological fluid includes: a controller, a non-safety critical component, a safety-critical component, a treatment interface, one or more processors; memory; and one or more programs, wherein the one or more programs are stored in the memory and configured to be executed by the one or more processors, the one or more programs including instructions for: in response to a coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component to the treatment interface through the treatment interface, the message based on a domain-specific interface language; and determining a state of the non-safety critical component or the safety-critical component based on the message.

In another aspect, a non-transitory computer readable storage medium storing one or more programs, the one or more programs comprising instructions, which when executed by an electronic device with one or more processors and memory, cause the device to: couple the non-safety critical component or the safety-critical component to the treatment interface; in response to the coupling of the non-safety critical component or the safety-critical component to the treatment interface, detect, with the controller, a presence of the non-safety critical component or the safety-critical component in the electronic device; transmit a message between the controller and the non-safety critical component or the safety-critical component to the treatment interface through the treatment interface, the message based on a domain-specific interface language; and determine a state of the non-safety critical component or the safety-critical component based on the message.

In some embodiments, the electronic device includes a plurality of non-safety critical components, a first controller communicatively coupled to the plurality of non-safety critical components, a plurality of safety critical components, and a second controller communicatively coupled to the plurality of safety critical components. In some embodiments, the electronic device includes a treatment interface.

In some embodiments, an electronic device for treating a biological fluid, includes: a plurality of non-safety critical components; a first controller communicatively coupled to the plurality of non-safety critical components and configured to operate the plurality of non-safety critical components; a plurality of safety critical components, wherein the safety critical components comprise: one or more platforms, wherein each platform of the one or more platforms is configured to carry one or more biological fluids; one or more light devices, wherein each light device is configured to illuminate the biological fluid; and one or more safety components; wherein the one or more safety components are configured to monitor the operation of the safety critical components; and a second controller communicatively coupled to the plurality of safety critical components and communicatively coupled to the first controller, wherein the second controller is configured to coordinate one or more operations involving the plurality of safety critical components; wherein the first controller and the second controller communicate with one another using a domain-specific interface language configured to isolate the plurality of non-safety critical components from the plurality of safety-critical components.

In some embodiments, the first controller includes an output port, and wherein the first controller is configured to communicate with an external computing device using the output port.

In some embodiments, isolating the plurality of non-safety critical components from the plurality of safety-critical components includes configuring the domain-specific interface language so as to minimize an impact to the plurality of safety critical components from one or more modifications to the non-safety critical components.

In some embodiments, the device further includes one or more treatment chambers configured to receive the biological fluid, and wherein each platform of the one or more platforms are configured to be positioned in a treatment chamber of the one of the one or more treatment chambers.

In some embodiments, the safety critical components further comprise one or more agitators, wherein each agitator is configured to agitate at least one of the one or more platforms.

In some embodiments, the safety critical components further comprise one or more sensors configured to detect light energy from the one or more modular light devices.

In some embodiments, the one or more modular light devices includes one or more arrays of light sources positioned to illuminate the biological fluid and wherein the one or more arrays of light sources are configured to emit light in an ultraviolet light spectrum.

In some embodiments, the one or more arrays of light sources each comprise a first light source channel configured to emit ultraviolet light with a first peak wavelength from about 315 nm to about 350 nm.

In some embodiments, the first light source channel comprises one or more light sources each of which emits light having a full-width half-maximum (FWHM) spectral bandwidth of less than 20 nanometers.

In some embodiments, the first light source channel comprises one or more light sources, and wherein the one or more light sources are light emitting diodes (LEDs).

In some embodiments, the one or more light devices further comprise one or more sensors configured to detect light energy from the one or more arrays of light sources.

In some embodiments, the one or more safety critical components includes computing hardware configured to perform one or more algorithms and configured to store information regarding the operation of the electronic device.

In some embodiments, the second controller is configured to turn one or more of the safety critical components on or off based on one or more operating conditions of the device.

In some embodiments, the one or more safety components are collectively configured to implement a hardware watchdog.

In some embodiments, the one or more safety components are collectively configured to implement a software watchdog.

In some embodiments, the one or more non-safety critical components includes a display configured to provide information to a user of the device and/or receive an input from the user of the device.

In some embodiments, for use in a method of treating a biological fluid including: providing a biological fluid in admixture with a photoactive pathogen inactivation compound, and illuminating the biological fluid with ultraviolet light with a first peak wavelength of from about 315 nm to about 350 nm emitted by a set of one or more first light sources, wherein: 1) each of the one or more first light sources emits light having a full-width half-maximum (FWHM) spectral bandwidth of less than 20 nanometers, or 2) each of the one or more first light sources is a light-emitting diode (LED), and wherein illuminating the biological fluid occurs for a duration and at an intensity sufficient to inactivate a pathogen in the biological fluid.

In some embodiments, the device further includes: a treatment interface, wherein the first controller is communicatively coupled to the plurality of non-safety critical components and the second controller is communicatively coupled to the plurality of safety critical components through the treatment interface; one or more processors; memory; and one or more programs, wherein the one or more programs are stored in the memory and configured to be executed by the one or more processors, the one or more programs including instructions for: in response to communicatively coupling the plurality of non-safety critical components to the treatment interface and communicatively coupling the plurality of safety-critical component to the treatment interface, detecting, with the controller, presences of the plurality of non-safety critical component and the plurality of safety-critical component in the electronic device; transmitting first messages between the first controller and the non-safety critical component through the treatment interface; transmitting second messages between the second controller and the safety-critical component through the treatment interface, wherein the first and second messages are based on the domain-specific interface language; determining states of the non-safety critical components based on the first messages; and determining states of the safety critical components based on the second messages.

In some embodiments, a non-safety critical component or a safety-critical component is in a first state, and the one or more programs further includes instructions for: changing the state of the non-safety critical component or the safety-critical component from the first state to a second state; in response to the changing the state, sending, from of the non-safety critical component or the safety-critical component to the first controller or the second controller through the treatment interface, a second message; receiving, at the first controller or the second controller, the second message; and in response to receiving the second message, determining a second state of the treatment component.

In some embodiments, the one or more programs further includes instructions for providing power to the electronic device; and the presences of the plurality of non-safety critical component and the plurality of safety-critical component are detected further in response to the providing of power to the electronic device.

In some embodiments, the one or more programs further includes instructions for: in response to the providing of power to the electronic device, assigning local network addresses and ports to the plurality of non-safety critical components and the plurality of safety-critical components, wherein the local network addresses or ports are based on the domain-specific interface language.

In some embodiments, the one or more messages written in the domain-specific interface language can be transmitted using TCP/IP.

In some embodiments, a method of treating a biological fluid includes: providing a biological fluid in admixture with a photoactive pathogen inactivation compound, and illuminating the biological fluid with any of the above devices, for a duration and at an intensity sufficient to inactivate a pathogen in the biological fluid.

In some embodiments, a method of operating an electronic device for treating a biological fluid, the electronic device including a controller, a non-safety critical component, a safety-critical component, and a treatment interface, the method includes: coupling the non-safety critical component or the safety-critical component to the treatment interface; in response to the coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component through the treatment interface, the message based on a domain-specific interface language; and determining a state of the non-safety critical component or the safety-critical component based on the message.

In some embodiments, the electronic device further comprises a second controller coupled to the treatment interface and the safety-critical component is coupled to the treatment interface, the method further includes: coupling the non-safety critical component to the treatment interface; and isolating the non-safety critical component from the safety-critical component, wherein the isolation comprises configuring the domain-specific interface language so as to minimize an impact to the safety-critical component from one or more modifications to the non-safety critical component.

In some embodiments, the non-safety critical component or the safety-critical component is in a first state, the method further includes: changing the state of the non-safety critical component or the safety-critical component from the first state to a second state; in response to the changing the state, sending, from of the non-safety critical component or the safety-critical component to the controller through the treatment interface, a second message; receiving, at the controller, the second message; and in response to receiving the second message, determining a second state of the treatment component.

In some embodiments, the safety-critical component is one of a platform, modular light device, agitator, and a safety component, wherein the one or more safety components are configured to monitor the operation of the safety-critical components.

In some embodiments, the method further includes isolating the treatment interface from an external network using the domain-specific interface language.

In some embodiments, the method further includes providing power to the electronic device; the presence of the treatment component is detected further in response to the providing of power to the electronic device.

In some embodiments, the method further includes in response to the providing of power to the electronic device, assigning a local network address or a port to the non-safety critical component or the safety-critical component, wherein the local network address or port is based on the domain-specific interface language.

In some embodiments, one or more messages written in the domain-specific interface language can be transmitted using TCP/IP.

In some embodiments, an electronic device for treating a biological fluid includes: a controller, a non-safety critical component, a safety-critical component, a treatment interface, one or more processors; memory; and one or more programs, wherein the one or more programs are stored in the memory and configured to be executed by the one or more processors, the one or more programs including instructions for: in response to a coupling of the non-safety critical component or the safety-critical component to the treatment interface, detecting, with the controller, a presence of the non-safety critical component or the safety-critical component in the electronic device; transmitting a message between the controller and the non-safety critical component or the safety-critical component to the treatment interface through the treatment interface, the message based on a domain-specific interface language; and determining a state of the non-safety critical component or the safety-critical component based on the message.

In some embodiments, a non-transitory computer readable storage medium storing one or more programs, the one or more programs comprising instructions, which when executed by an electronic device with one or more processors and memory, cause the device to: couple the non-safety critical component or the safety-critical component to the treatment interface; in response to the coupling of the non-safety critical component or the safety-critical component to the treatment interface, detect, with the controller, a presence of the non-safety critical component or the safety-critical component in the electronic device; transmit a message between the controller and the non-safety critical component or the safety-critical component to the treatment interface through the treatment interface, the message based on a domain-specific interface language; and determine a state of the non-safety critical component or the safety-critical component based on the message.

Variations of the embodiments provided herein may become apparent to those working in the art upon reading the foregoing description. It is expected that skilled artisans will be able to employ such variations as appropriate, and the practice of the compositions, methods, and kits described herein otherwise than as specifically described herein. Accordingly, the systems and methods described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context. The following is a list of particular embodiments of the present disclosure. The list is exemplary is it not intended to be limiting of the disclosure provided herein.

Embodiment 1: A modular light device for use in conjunction with an electronic device for treating a biological fluid, wherein the modular light device includes a plurality of components collectively configured to transmit light to one or more biological fluids for treatment, the modular light device comprising:
- a housing configured to house one or more components of the modular light device;
- a light source array chamber configured to transmit light, wherein the light source array chamber comprises:
  - one or more light source arrays, each comprising a plurality of light sources configured to generate UV light; and
  - one or more light sensors configured to detect light;
- a window portion configured to pass UV light generated by the plurality of light sources to the one or more biological fluids for treatment; and
- a driver communicatively coupled to one or more components of the modular light device and configured to operate the one or more components.

Embodiment 2: The modular light device of embodiment 1, wherein the light source array chamber comprises one or more temperature sensors configured to measure a temperature.

Embodiment 3: The modular light device of embodiment 1 or embodiment 2, wherein each light source of the plurality of light sources emits light having a full-width half-maximum (FWHM) spectral bandwidth of less than 20 nanometers.

Embodiment 4: The modular light device of any one of embodiments 1-3, wherein each light source of the plurality of light sources is a light-emitting diode (LED).

Embodiment 5: The modular light device of any one of embodiments 1-4, wherein the one or more light source arrays each comprises a respective first light source channel configured to emit ultraviolet light with a first peak wavelength of the array.

Embodiment 6: The modular light device of any one of embodiments 1-5, wherein the electronic device comprises a treatment chamber configured to receive at least one of the one or more biological fluids.

Embodiment 7: The modular light device of any one of embodiments 1-6, wherein the modular light device is configured to be positioned within the electronic device to transmit light to one or more biological fluids in a treatment chamber of the electronic device.

Embodiment 8: The modular light device of any one of embodiments 1-7, wherein the housing comprises one or more tracks configured to mechanically interface with one or more rails of the electronic device so as to mechanically secure the modular light device when placed into the electronic device.

Embodiment 9: The modular light device of embodiment 8, wherein the one or more tracks are configured to allow the modular light device to be slideably moveable so to remove and insert the modular light device into the electronic device.

Embodiment 10: The modular light device of any one of embodiments 1-9, wherein the modular light device comprises one or more heat exchangers configured to transfer heat away from the light source array and/or the modular light device.

Embodiment 11: The modular light device of embodiment 10, wherein the one or more heat exchangers are configured to exchange heat with air that is passed across the one or more heat exchangers to transfer heat away from the light source array and/or the modular light device.

Embodiment 12: The modular light device of any one of embodiments 10-11, wherein the one or more heat exchangers are configured to exchange heat with air that is passed across the one or more heat exchangers from one or more fans of the electronic device.

Embodiment 13: The modular light device of any one of embodiments 1-12, wherein the window portion comprises a window material covering or enclosing an opening of the modular light device, and wherein the window material is made of glass.

Embodiment 14: The modular light device of any one of embodiments 1-12, wherein the window portion comprises a window material covering or enclosing an opening of the modular light device, and wherein the window material is made of a polymeric material.

Embodiment 15: The modular light device of any one of embodiments 1-14, wherein the window portion is at least 80% transmissive for UV light of a selected wavelength.

Embodiment 16: The modular device of any one of embodiments 1-15, wherein the modular light device comprises one or more light sensors disposed on the one or more of the light source arrays.

Embodiment 17: The modular light device of any one of embodiments 1-16, wherein the modular light device comprises one or more light sensors disposed at the window portion and configured to detect light generated by the modular light device.

Embodiment 18: The modular light device of any one of embodiments 1-17, wherein the modular light device comprises one or more circuits disposed at the window portion, and wherein the one or more circuits comprises one or more light sensors disposed on the circuits and configured to detect light generated by the modular light device.

Embodiment 19: The modular light device of any one of embodiments 1-18, wherein the light source array chamber includes a plurality of reflector panels disposed along one or more edges of the light source array chamber.

Embodiment 20: The modular light device of embodiment 19, wherein the plurality of reflector panels are disposed in the light source array chamber so as to minimize a loss of light energy at a perimeter of the light source array chamber.

Embodiment 21: The modular light device of any one of embodiments 1-20, wherein the one or more light sensors of the light source array chamber are oriented so as to detect light generated by a separate modular light device.

Embodiment 22: The modular light device of any one of embodiments 1-21, wherein the one or more light sensors are implemented using photodiodes.

Embodiment 23: The modular light device of any one of embodiments 1-22, wherein the one or more temperature sensors are implemented using thermistors.

Embodiment 24: The modular light device of any one of embodiments 1-23, wherein one or more of the one or more temperature sensors are configured to measure a temperature at a junction between a light source of the one or more light sources and a printed circuit board (PCB) on which the light source is disposed upon.

Embodiment 25: The modular light device of any one of embodiments 1-24, wherein the plurality of light sources are configured to generate UV-A light.

Embodiment 26: The modular light device of embodiment 25, wherein the plurality of light sources are configured to generate light with a first peak wavelength from about 315 nm to about 350 nm.

Embodiment 27: The modular light device of any one of embodiments 1-24, wherein the plurality of light sources are configured to generate UV-B or UV-C light.

Embodiment 28: The modular light device of any one of embodiments 5-27, wherein the one or more arrays of light sources each comprises a respective second light source channel configured to emit ultraviolet light with a second peak wavelength of the array, wherein the second peak wavelength differs from the first peak wavelength by at least 5 nanometers.

Embodiment 29: The modular light device of embodiment 28, wherein the one or more arrays of light sources each comprises a respective first light source channel configured to emit ultraviolet light with a first peak wavelength of the array in the UV-A spectrum, and a respective second light source channel configured to emit ultraviolet light with a second peak wavelength of the array in the UV-B or UV-C spectrum.

Embodiment 30: The modular light device of any one of embodiments 1-29, wherein the housing comprises one or more electronic interfaces configured to communicatively couple the modular light device to the electronic device.

Embodiment 31: The modular light device of embodiment 30, wherein the one or more electronic interfaces includes an interlock connection configured to allow the electronic device to turn off the modular light device.

Embodiment 32: The modular light device of embodiment 30, wherein the one or more electronic interfaces includes a communications port configured to allow the electronic device to transmit commands to the modular light device, and configured to allow for the modular light device to transmit data to the electronic device.

Embodiment 33: The modular light device of embodiment 30, wherein the one or more electronic interfaces includes a power port configured to transmit power from the electronic device to the modular light device.

Embodiment 34: The modular light device of any one of embodiments 1-33, wherein a number of light sources of the light source array chamber is configured to provide light for a pre-determined illumination volume to the one or more biological fluids.

Embodiment 35: The modular light device of any one of embodiments 1-34, wherein the one or more light sources of the light source array chamber collectively generate light such that an irradiance of the light is substantially uniform at a surface of the biological fluid.

Embodiment 36: The modular light device of embodiment 35 wherein a variance in the irradiance of the light across a surface of the biological fluid is less than 25%.

Embodiment 37: The modular light device of any one of embodiments 1-36, wherein the one or more light sources of the light source array chamber are LEDs configured to have a beam angle of about 110 to about 130 degrees.

Embodiment 38: The modular light device of any one of embodiments 1-37, wherein a dose of light delivered from the modular light device to a biological fluid during a treatment process is based on light detected by one or more of the one or more light sensors.

Embodiment 39: The modular light device of any one of embodiments 1-38, wherein an amount of time that the modular light device is activated during a treatment process is based on light detected by one or more of the one or more light sensors.

Embodiment 40: The modular light device of any one of embodiments 1-39, wherein an intensity of light generated by the modular light device during a treatment process is based on light detected by one or more of the one or more light sensors.

Embodiment 41: The modular light device of any one of embodiments 1-40, wherein the electronic device for treating a biological fluid comprises a first modular light device oriented to face a biological fluid to be treated, and wherein the first modular light device delivers light to the biological sample for treatment.

Embodiment 42: The modular light device of any one of embodiments 1-41, wherein the electronic device for treating a biological fluid comprises a first modular light device and a second modular light device, wherein the first and second modular light devices oriented to face one another, and wherein the first and second modular light devices collectively deliver light to a biological fluid for treatment.

Embodiment 43: The modular light device of embodiment 42, wherein the first and second light devices are configured to perform a test comprising:

transmitting light from the first modular light device;

detecting the light transmitted by the first device by one or more light sensors of the second modular light device; and determining the presence or absence of one or more occlusions to the light transmitted by the first modular light device, by comparing the detected light to a pre-determined amount of light.

Embodiment 44: The modular light device of embodiment 43, wherein the test further comprises:

transmitting light from the second modular light device;

detecting the light transmitted by the second modular light device by one or more light sensors of the first modular light device; and determining the presence or absence of one or more occlusions to the light transmitted by the second modular light device, by comparing the detected light to a pre-determined level of light.

Embodiment 45: The modular light device of embodiment 43 or 44, wherein the test further comprises: determining a baseline amount of light transmitted by the first modular light device to the second modular light device.

Embodiment 46: The modular light device of any one of embodiments 43-45, wherein the test is a test to determine the presence of obstructed light path in the electronic device.

Embodiment 47: The modular light device of any one of embodiments 43-45, wherein the test is a test to determine the presence of a biological fluid to be treated in the electronic device.

Embodiment 48: The modular light device of any one of embodiments 17-47, wherein the modular light device is configured to perform a test comprising:

transmitting light from one or more light source arrays of the light source array chamber of the modular light device;

detecting the light transmitted by the one or more light source arrays by one or more light sensors of the modular light device.

Embodiment 49: The modular light device of embodiment 48, wherein the one or more light sensors are light sensors disposed at the window portion of the modular light device.

Embodiment 50: The modular light device of embodiment 48 or embodiment 49, wherein the test further comprises: comparing the detected light to a pre-determined amount of light.

Embodiment 51: The modular light device of any one of embodiments 48-50, wherein the test further comprises one or both of:

a) determining the integrity of one or more of the one or more sensors; and b) determining the integrity of one or more light sources of the one or more light source arrays.

Embodiment 52: The modular light device of any one of embodiments 1-51, wherein the modular light device is configured to perform a calibration process comprising:

transmitting light from one or more light source arrays of the modular light device;

receiving data from a calibration device configured to detect the light transmitted by the light source array(s) of the modular light device by one or more light sensors of the calibration device, the calibration device positioned within the electronic device;

comparing the received data to a pre-determined amount of light; and adjusting the intensity of one or more light sources of the light source array(s) based on the comparison.

Embodiment 53: A method for treating a biological fluid comprising:

providing the biological fluid; and illuminating the biological fluid with one or more modular light devices of any one of embodiments 1-52, for a duration and at an intensity sufficient to inactivate a pathogen in the biological fluid.

Embodiment 54: A method for treating a biological fluid comprising:

providing the biological fluid in admixture with a pathogen inactivation compound; and illuminating the biological fluid with one or more modular light devices of any one of embodiments 1-52 for a duration and at an intensity sufficient to inactivate a pathogen in the biological fluid.

The foregoing description, for purpose of explanation, has made reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments, with various modifications, that are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

What is claimed is:

1. A modular light device configured to be positioned within an electronic device for treating a biological fluid, wherein the modular light device includes a plurality of components collectively configured to transmit light to one or more biological fluids for treatment, the modular light device comprising:

a housing configured to house one or more components of the modular light device;

a light source array chamber configured to transmit light, wherein the light source array chamber comprises:

one or more light source arrays, each comprising a plurality of light sources configured to generate UV light; and one or more light sensors configured to detect light, wherein at least one of the one or more light sensors is configured to detect light generated by the one or more light source arrays of the modular light device and is oriented facing the one or more light source arrays;

a window portion configured to pass UV light generated by the plurality of light sources from the one or more light source arrays of the light source array chamber to the one or more biological fluids for treatment, wherein the window portion comprises a window material covering or enclosing an opening of the housing of the modular light device;

a controller configured to control the light generated by the one or more light source arrays based at least in part on the light detected by the one or more light sensors; and a driver communicatively coupled to and configured to operate one or more components of the plurality of components of the modular light device, wherein the modular light device is a first modular light device configured to be positioned at a treatment chamber within the electronic device in an orientation to transmit light to one or more biological fluids positioned on a platform in the treatment chamber of the electronic device, and wherein the modular light device is configured to be positioned in an orientation facing a second modular light device that is positioned within the electronic device, and wherein at least one of the one or more light sensors of the first modular light device is configured to detect light transmitted by the second modular light device.

2. The modular light device of claim 1, wherein the light source array chamber comprises one or more temperature sensors configured to measure a temperature.

3. The modular light device of claim 2, wherein the one or more temperature sensors are implemented using thermistors.

4. The modular light device of claim 2, wherein one or more of the one or more temperature sensors are configured to measure a temperature at a junction between a light source of the plurality of light sources and a printed circuit board (PCB) on which the light source is disposed upon.

5. The modular light device of claim 1, wherein each light source of the plurality of light sources emits light having a full-width half-maximum (FWHM) spectral bandwidth of less than 20 nanometers.

6. The modular light device of claim 5, wherein the one or more arrays of light sources each comprises a respective second light source channel configured to emit ultraviolet light with a second peak wavelength of the array, wherein the second peak wavelength differs from the first peak wavelength by at least 5 nanometers.

7. The modular light device of claim 1, wherein the one or more arrays of light sources each comprises a respective first light source channel configured to emit ultraviolet light with a first peak wavelength of the array in the UV-A spectrum, and a respective second light source channel configured to emit ultraviolet light with a second peak wavelength of the array in the UV-B or UV-C spectrum.

8. The modular light device of claim 1, wherein each light source of the plurality of light sources is a light-emitting diode (LED).

9. The modular light device of claim 8, wherein the one or more light source arrays each comprises a respective first light source channel configured to emit ultraviolet light with a first peak wavelength of the array.

10. The modular light device of claim 1, wherein the electronic device comprises a treatment chamber configured to receive at least one of the one or more biological fluids.

11. The modular light device of claim 1, wherein the housing comprises one or more tracks configured to mechanically interface with one or more rails of the electronic device so as to mechanically secure the modular light device when placed into the electronic device.

12. The modular light device of claim 11, wherein the one or more tracks are configured to allow the modular light device to be slideably moveable so to remove and insert the modular light device into the electronic device.

13. The modular light device of claim 1, wherein the modular light device comprises one or more heat exchangers configured to transfer heat away from the light source array and/or the modular light device.

14. The modular light device of claim 13, wherein the one or more heat exchangers are configured to exchange heat with air that is passed across the one or more heat exchangers to transfer heat away from the light source array and/or the modular light device.

15. The modular light device of claim 13, wherein the one or more heat exchangers are configured to exchange heat with air that is passed across the one or more heat exchangers from one or more fans of the electronic device.

16. The modular light device of claim 1, wherein the window material is made of glass.

17. The modular light device of claim 1, wherein the window material is made of a polymeric material.

18. The modular light device of claim 1, wherein the window portion is at least 80% transmissive for UV light generated by the plurality of light sources.

19. The modular light device of claim 1, wherein the modular light device comprises one or more light sensors disposed on the one or more of the light source arrays.

20. The modular light device of claim 1, wherein the one or more light sensors configured to detect light generated by the one or more light source arrays of the modular light device and oriented facing the one or more light source arrays are disposed at the window portion.

21. The modular light device of claim 20, wherein the modular light device is configured to perform a test comprising:

transmitting light from one or more light source arrays of the light source array chamber of the modular light device; and detecting the light transmitted by the one or more light source arrays by one or more light sensors of the modular light device.

22. The modular light device of claim 1, wherein the modular light device comprises one or more circuits disposed at the window portion, and wherein the one or more circuits comprise one or more light sensors disposed on the circuits and configured to detect light generated by the modular light device.

23. The modular light device of claim 1, wherein the light source array chamber includes a plurality of reflector panels disposed along one or more edges of the light source array chamber.

24. The modular light device of claim 23, wherein the plurality of reflector panels are disposed in the light source array chamber so as to minimize a loss of light energy at a perimeter of the light source array chamber.

25. The modular light device of claim 24, wherein the one or more light sensors of the light source array chamber are oriented so as to detect light generated by a separate modular light device.

26. The modular light device of claim 1, wherein the one or more light sensors are implemented using photodiodes.

27. The modular light device of claim 1, wherein the plurality of light sources are configured to generate UV-A light.

28. The modular light device of claim 27, wherein the plurality of light sources are configured to generate light with a first peak wavelength from about 315 nm to about 350 nm.

29. The modular light device of claim 1, wherein the plurality of light sources are configured to generate UV-B or UV-C light.

30. The modular light device of claim 1, wherein the housing comprises one or more electronic interfaces configured to communicatively couple the modular light device to the electronic device.

31. The modular light device of claim 30, wherein the one or more electronic interfaces include an interlock connection configured to allow the electronic device to turn off the modular light device.

32. The modular light device of claim 30, wherein the one or more electronic interfaces include a communications port configured to allow the electronic device to transmit commands to the modular light device, and configured to allow for the modular light device to transmit data to the electronic device.

33. The modular light device of claim 30, wherein the one or more electronic interfaces include a power port configured to transmit power from the electronic device to the modular light device.

34. The modular light device of claim 1, wherein a number of light sources of the light source array chamber is configured to provide light for a pre-determined illumination volume to the one or more biological fluids.

35. The modular light device of claim 1, wherein the plurality of light sources of the light source array chamber collectively illuminates any 5 $cm^2$ area on the biological fluid with less than 25% variance from the integrated variance of an entire biological fluid intercept plane.

36. The modular light device of claim 1, wherein the plurality of light sources of the light source array chamber collectively generate light such that a variance in the irradiance of the light across a surface of the biological fluid is less than 25%.

37. The modular light device of claim 1, wherein the plurality of light sources of the light source array chamber are LEDs configured to have a beam angle of 110 to 130 degrees.

38. The modular light device of claim 1, wherein a dose of light delivered from the modular light device to a biological fluid during a treatment process is based on light detected by one or more of the one or more light sensors.

39. The modular light device of claim 1, wherein an amount of time that the modular light device is activated during a treatment process is based on light detected by one or more of the one or more light sensors.

40. The modular light device of claim 1, wherein an intensity of light generated by the modular light device during a treatment process is based on light detected by one or more of the one or more light sensors.

41. The modular light device of claim 1, wherein the first modular light device is configured to perform a test with a second modular light device when positioned in the electronic device in an orientation facing the second modular light device, comprising:

transmitting a pre-determined amount of light from the first modular light device, the transmitted light being detectable by one or more sensors of the second modular light device;

wherein detection of the pre-determined amount of transmitted light is indicative of an absence of one or more inclusions to the light transmitted from the first modular light device, and wherein detection of a decreased amount of transmitted light compared to the pre-determined amount of transmitted light is indicative of a presence of one or more occlusions to the light transmitted from the first modular light device.

42. The modular light device of claim 41, wherein the test further comprises:

detecting the light transmitted by the second modular light device by one or more light sensors of the first modular light device; and determining the presence or absence of one or more occlusions to the light transmitted by the second modular light device, by comparing the detected light to a pre-determined level of light.

43. The modular light device of claim 41, wherein the test further comprises determining a baseline amount of light transmitted by the first modular light device to the second modular light device.

44. The modular light device of claim 41, wherein the test is a test to determine a presence of an obstructed light path in the electronic device.

45. The modular light device of claim 41, wherein the test is a test to determine a presence of a biological fluid to be treated in the electronic device.

46. The modular light device of claim 41, wherein the one or more light sensors are light sensors disposed at the window portion of the modular light device.

47. The modular light device of claim 41, wherein the test further comprises comparing the detected light to a pre-determined amount of light.

48. The modular light device of claim 41, wherein the test further comprises one or both of:

a) determining the integrity of one or more of the one or more light sensors; and b) determining the integrity of one or more light sources of the one or more light source arrays.

49. The modular light device of claim 1, wherein the modular light device is configured to perform a calibration process comprising:

transmitting light from one or more light source arrays of the modular light device;

receiving data from a calibration device configured to detect the light transmitted by the light source array(s) of the modular light device by one or more light sensors of the calibration device, the calibration device positioned within the electronic device;

comparing the received data to a pre-determined amount of light; and adjusting the intensity of one or more light sources of the light source array(s) based on the comparison.

50. A method for treating a biological fluid comprising: illuminating the biological fluid with one or more modular light devices, wherein the one or more modular light devices comprises the modular light device of claim 1, for a duration and at an intensity sufficient to inactivate a pathogen in the biological fluid.

51. A method for treating a biological fluid comprising: providing the biological fluid in admixture with a pathogen inactivation compound; and illuminating the biological fluid with one or more modular light devices, wherein the one or more modular light devices comprises the modular light device of claim 1, for a duration and at an intensity sufficient to inactivate a pathogen in the biological fluid.

52. The modular light device of claim 1, wherein the modular light device comprises one or more fans.

53. The modular light device of claim 6, wherein the one or more arrays of light sources each comprises a respective first light source channel configured to emit ultraviolet light with a first peak wavelength of the array in the UV-A spectrum, and a respective second light source channel configured to emit ultraviolet light with a second peak wavelength of the array in the UV-A spectrum.

54. The modular light device of claim 22, wherein each of the one or more circuits has a width of 5 millimeters or less.

55. The modular light device of claim 41, wherein the test is a test to determine a presence of an obstructed light path on a platform or tray of the electronic device.

56. The modular light device of claim 41, wherein the test is a test to determine a presence of an obstructed light path in the window portion of the first modular light device.

57. The modular light device of claim 22, wherein each of the one or more circuits has a width of 4 millimeters or less.

58. The modular light device of claim 22, wherein each of the one or more circuits has a width of 3 millimeters or less.

59. The modular light device of claim 1, wherein the controller is communicatively coupled to the driver and configured to operate the driver.

60. The modular light device of claim 1, wherein the controller is configured to facilitate communication between the electronic device and the modular light device.

* * * * *